US011207282B2

(12) United States Patent
Kline et al.

(10) Patent No.: US 11,207,282 B2
(45) Date of Patent: *Dec. 28, 2021

(54) TUNEABLE DELIVERY OF NANOPARTICLE BOUND ACTIVE PLASMIN FOR THE TREATMENT OF THROMBOSIS

(71) Applicant: Indiana University Research and Technology Corporation, Indianapolis, IN (US)

(72) Inventors: Jeffrey A. Kline, Carmel, IN (US); Nathan J. Alves, Indianapolis, IN (US); Daren M. Beam, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/792,950

(22) Filed: Feb. 18, 2020

(65) Prior Publication Data

US 2020/0261386 A1 Aug. 20, 2020

Related U.S. Application Data

(63) Continuation of application No. 15/501,905, filed as application No. PCT/US2015/043592 on Aug. 4, 2015, now Pat. No. 10,583,104.
(Continued)

(51) Int. Cl.
*A61K 47/69* (2017.01)
*A61K 9/127* (2006.01)
(Continued)

(52) U.S. Cl.
CPC .......... *A61K 31/196* (2013.01); *A61K 38/482* (2013.01); *A61K 38/484* (2013.01);
(Continued)

(58) Field of Classification Search
CPC ................. A61K 31/196; B82Y 5/00
See application file for complete search history.

(56) References Cited

U.S. PATENT DOCUMENTS

| 4,866,040 A | 9/1989 | Stracher et al. |
| 5,990,079 A | 11/1999 | Wolf et al. |
(Continued)

FOREIGN PATENT DOCUMENTS

| EP | 0165612 A2 | 6/1985 |
| WO | 2014052311 A1 | 4/2014 |

OTHER PUBLICATIONS

Barnabe Chaize, Jacques-Philippe Colletier, Mathias Winterhalter, and Didier Fournier. "Encapsulation of Enzymes in Liposomes: High Encapsulation Efficiency and Control of Substrate Permeability." Artificial Cells, Blood Substitutes, and Biotechnology, vol. 32, No. 1, 2004, pp. 67-75. (Year: 2004).*
(Continued)

Primary Examiner — Isaac Shomer
(74) Attorney, Agent, or Firm — Stinson LLP

(57) ABSTRACT

Compositions and methods for therapeutic delivery are disclosed. More particularly, the present disclosure relates to nanoparticle compositions that sequester the activity of a target molecule while leaving other domains accessible to bind targeted tissues of interest. Methods for thrombus dissolution include administering a nanoparticle reversibly coupled to a target molecule that can dissolve a blood clot. Compositions and methods for inducing blood clotting are also disclosed. Methods for inducing blood clotting include administering a nanoparticle reversibly coupled to a target molecule that can induce the formation of a blood clot. Methods for sequestering a target molecule are also disclosed. The method includes reversibly coupling a target molecule to a nanoparticle having an affinity ligand that reversibly couples the target molecule, and thus, sequesters
(Continued)

the target molecule activity until the target molecule interacts with its substrate resulting in the release of the target molecule.

11 Claims, 30 Drawing Sheets

Specification includes a Sequence Listing.

Related U.S. Application Data

(60) Provisional application No. 62/033,898, filed on Aug. 6, 2014, provisional application No. 62/098,584, filed on Dec. 31, 2014, provisional application No. 62/181,580, filed on Jun. 18, 2015.

(51) Int. Cl.
| | |
|---|---|
| *B82Y 5/00* | (2011.01) |
| *A61K 31/196* | (2006.01) |
| *A61K 38/48* | (2006.01) |
| *A61K 38/49* | (2006.01) |
| *A61K 47/54* | (2017.01) |
| *A61K 45/06* | (2006.01) |

(52) U.S. Cl.
CPC ........ *A61K 38/486* (2013.01); *A61K 38/4833* (2013.01); *A61K 38/4846* (2013.01); *A61K 38/4853* (2013.01); *A61K 38/4866* (2013.01); *A61K 38/49* (2013.01); *A61K 45/06* (2013.01); *A61K 47/544* (2017.08); *A61K 47/6909* (2017.08); *A61K 47/6911* (2017.08); *A61K 47/6929* (2017.08); *C12Y 304/21* (2013.01); *C12Y 304/21001* (2013.01); *C12Y 304/21004* (2013.01); *C12Y 304/21005* (2013.01); *C12Y 304/21007* (2013.01); *C12Y 304/21008* (2013.01); *C12Y 304/21027* (2013.01); *C12Y 304/21034* (2013.01); *C12Y 304/21036* (2013.01); *C12Y 304/21069* (2013.01); *A61K 9/127* (2013.01); *B82Y 5/00* (2013.01); *Y10S 977/773* (2013.01); *Y10S 977/906* (2013.01); *Y10S 977/907* (2013.01)

(56) References Cited

U.S. PATENT DOCUMENTS

| | | | |
|---|---|---|---|
| 6,123,959 | A | 9/2000 | Jones et al. |
| 6,224,903 | B1 | 5/2001 | Martin et al. |
| 8,318,206 | B2 | 11/2012 | Stevens et al. |
| 10,583,104 | B2 * | 3/2020 | Kline ............... A61K 47/6909 |
| 2002/0041898 | A1 | 4/2002 | Unger et al. |
| 2003/0031664 | A1 | 2/2003 | Reed |
| 2005/0080075 | A1 | 4/2005 | Nichols et al. |
| 2005/0169980 | A1 | 8/2005 | Allen et al. |
| 2007/0092558 | A1 | 4/2007 | Heavner et al. |
| 2011/0044903 | A1 | 2/2011 | Borrelli |
| 2011/0223151 | A1 | 9/2011 | Behrens et al. |
| 2012/0189601 | A1 | 7/2012 | Esko et al. |
| 2013/0017239 | A1 | 1/2013 | Viladot Petit et al. |
| 2013/0064765 | A1 | 3/2013 | Myerson et al. |
| 2013/0195752 | A1 | 8/2013 | Panyam et al. |
| 2014/0287049 | A1 | 9/2014 | Bilgicer et al. |

OTHER PUBLICATIONS

Sang Youn Hwang,, Hak Kyung Kim, Jaebum Choo, Gi Hun Seong, Thai Bao Dieu Hien, E.K. Lee. "Effects of operating parameters on the efficiency of liposomal encapsulation of enzymes." Colloids and Surfaces B: Biointerfaces 94 (2012), pp. 296-303. (Year: 2012).*
Alejandra I. Pérez-Molina, et al. "Thermodynamics of laminarinase partitioning in soya lecithin liposomes and their storage stability." Journal of Molecular Catalysis B: Enzymatic 72 (2011), pp. 65-72. (Year: 2011).*
Christensen et al., Stopped-flow fluorescence kinetics of bovine α2-antiplasmin inhibition of bovine midiplasmin; Biochem. J., 1995, vol. 385, pp. 97-102.
Coats et al., Comparative Inhibition of Thrombin, Plasmin, Trypsin, and Complement by Benzamidines Using Substituent Constants and Regression Analysis; Journal of Medicinal Chemistry, 1973, vol. 16, No. 10, 5-pages.
Cosse K., Study Finds Plasmin-Delivered Through a Bubble-More Effective Than tPA in Busing Clots., http://healthnews.uc.edu/news/?/22587—accessed by Examiner on Jun. 5, 2018, originally published on May 15, 2013, 2-printed pages, 2013.
De La Rica et al., Plasmonic ELISA for the ultrasensitive detection of disease biomarkers with the naked eye; Nature Nanotechnology; 2012; 4-pages.
De Vocht et al., Assessment of stability, toxicity and immunogenicity of new polymeric nanoreactors for use in enzyme replacement therapy of MNGIE; Journal of Controlled Release; 2009, vol. 137, pp. 246-254.
Hartono et al., Functionalized Mesoporous Silica with Very Large Pores for Cellulase Immobilization; J. Phys. Chem. C; 2010, vol. 114, pp. 8353-8362.
Hirsch et al., Easily reversible desthiobiotin binding to streptavidin, avidin, and other biotin-binding proteins: uses for protein labeling, detection, and isolation; Analytical Biochemistry, 2002, vol. 308, pp. 343-357.
Ho et al.., Ximelagatran: direct thrombin inhibitor; Vascular Health and Risk Management, 2006, vol. 2, No. 1, pp. 49-58.
Johnson et al., Novel method for immobilization of enzymes to magnetic nanoparticles; J. Nanopart Res., 2008, vol. 10, pp. 1009-1025.
Markwardt et al., Comparative Studies on the Inhibition of Trypsin, Plasmin, and Thrombin by Derivatives of Benzylamine and Benzamidine; European J. Biochem.; 1968, vol. 6, pp. 502-506.
Mohlstein et al., Development of nanoparticle-bound arylsulfulfatase B for enzyme replacement therapy of mucopolysaccharidosis VI; Pharmazie, 2013, vol. 68, pp. 549-554.
Popat et al., Mesoporous silica nanoparticles for bioadsorption, enzyme immobilisation, and delivery carriers; 2011, vol. 3, 20-pages.
Reed et al., Inhibition of Clot-Bound a2-Antiplasmin Enhances In Vivo Thrombolysis; 5-pages.
Shi et al., Aminopropyl-functionalized silicas synthesized by W/O micromulsion for immobilization of penicillin G acylase; Catalysis Today, 2009, vol. 148, pp. 184-188.
Wang et al., Mesoporous Silica Spheres as Supports for Enzyme Immobilization and Encapsulation; Chem. Mater, 2005, vol. 17, pp. 953-961.
Colonna et al., Ex vivo evaluation of prolidase loaded chitosan nanoparticles for the enzyme replacement therapy; European Journal of Pharmaceutics and Biopharmaceutics; 2008; vol. 70, pp. 58-65.
Reynolds et al., Enzyme replacement using liposome carriers in feline Gmi gangliosidosis fibroblasts; Nature, vol. 275, 1978, 2-pages.

* cited by examiner

4CB-Lys-Lys-(Palmitic Acid)$_2$

TUNEABLE DELIVERY OF NANOPARTICLE BOUND ACTIVE PLASMIN FOR THE TREATMENT OF THROMBOSIS

CROSS-REFERENCE TO RELATED APPLICATION

This application claims priority to U.S. Application Publication No. 2017/0189363, filed on Feb. 6, 2017, which claims priority to International Application Number PCT/US2015/043592, filed on Aug. 4, 2015, which claims benefit of U.S. Provisional Patent Application Ser. No. 62/033,898, filed Aug. 6, 2014; U.S. Provisional Application Ser. No. 62/098,584, filed Dec. 31, 2014; and U.S. Provisional Application Ser. No. 62/181,580, filed Jun. 18, 2015, the disclosures of which are hereby expressly incorporated by reference in their entireties.

STATEMENT IN SUPPORT FOR FILING A SEQUENCE LISTING

A paper copy of the Sequence Listing and a computer readable form of the Sequence Listing containing the file named "IURTC_2014-053-06_ST25.txt", which is 10,327 bytes in size (as measured in MICROSOFT WINDOWS® EXPLORER), are provided herein and are herein incorporated by reference. This Sequence Listing consists of SEQ ID NOS: 1-2.

BACKGROUND

The present disclosure relates generally to compositions and methods for therapeutic delivery. More particularly, the present disclosure relates to nanoparticle compositions that sequester a target molecule, methods for targeted delivery of a target molecule, methods for thrombus (blood clot) dissolution and methods for inducing blood clotting.

During injury of a blood vessel, aggregated platelets and cross-linked fibrin form a blood clot (thrombus) to prevent blood loss. The coagulation process is useful in closing up and maintaining the platelet plug on larger wounds. Though blood clotting is necessary for wound healing, it has the ability to cause severe health problems if the thrombus becomes detached and travels through the circulatory system. Particularly, acute vascular thrombosis, including coronary, cerebrovascular, and pulmonary thrombosis, causes more deaths than any other disease process in Western society. Thrombosis is the formation of a blood clot inside a blood vessel, which obstructs blood flow through the circulatory system. An embolus can also become lodged within a blood vessel and obstruct blood flow. Death of tissue can result when blood flow is cut-off in a blood vessel that supplies the tissue. If the thrombus reaches the heart, brain or lungs, it could lead to heart attack, stroke, or pulmonary embolism.

Treatment and prevention of blood clots involve the inhibition of clot formation and growth. Heparin, for example, binds to and activates antithrombin to inhibit the formation and growth of clots. Warfarin, for example, inhibits vitamin K epoxide reductase, which is needed for the synthesis of clotting factors such as prothrombin and factor VII. Other treatments involve dissolving blood clots (thrombolysis). For example, streptokinase and urokinase are administered intravenously and can be used to dissolve blood clots. Tissue plasminogen activator converts plasminogen into plasmin Activated plasmin, in turn, cleaves cross-linked γ-chains in the D-domain of fibrin (Aα 148-160) to effectively digest the thrombus. Plasminogen is a 91 kDa zymogen containing 791 amino acids, produced in-vivo by the liver, and is heavily glycosylated (2% carbohydrate) in its circulating form (FIG. 1). When cleaved at Arg561-Val562, plasminogen produces plasmin, a serine protease with a trypsin-like active site. Plasmin binds to thrombi via electrostatic attraction between its five kringle (K) domains to the exposed lysine residues on fibrin with a $K_d$=0.5 µM for lys-plasmin and $K_d$=5 µM for glu-plasmin. In order, K4 has the least, K1-K3 have moderate, and K5 has the highest affinity fibrin binding. Plasmin's activity is rapidly neutralized in plasma by the circulating proteins $\alpha_2$-antiplasmin, C1-inhibitor, and macroglobulin. The serpin $\alpha_2$-antiplasmin provides the most rapid and avid inhibition, whereby an Arg-Met residue binds directly to the serine residue in plasmin's active site with a rate constant of $4 \times 10^7$ $M^{-1} Sec^{-1}$.

Lack of target specificity poses the largest threat to the clinical therapeutic index of the plasminogen activators. Even when rt-PA is infused directly via a catheter buried within the thrombus, some degree of systemic plasminogen activation occurs, resulting in fibrinogenolysis and increased bleeding risk.

Alternatively, the inability of blood to clot can lead to excessive bleeding. Bleeding disorders, such as hemophilia and Von Willebrand disease, are characterized by longer bleeding episodes. Longer bleeding episodes can result in longer wound healing time, deep internal bleeding, joint damage, intracranial haemorrhage and shorter life expectancy. Additionally, bleeding injuries can sometimes require administration of a hemostatic agent to induce blood clot formation to stop blood loss. Antihemorrhagic agents work by inhibiting fibrinolysis or promoting coagulation. Examples of antihemorrhagic agents include antifibrinolytics, blood coagulation factors, fibrinogen, collagen, vitamin K and chitosan. Topical hemostatic agents are also available for use in inducing blood clot formation.

While the compositions and methods described above are suitable for preventing and treating blood clots, prevention of clotting can lead to excessive bleeding and some drugs can be non-specific to fibrin and digest other proteins. Accordingly, there exists a need to develop compositions and methods for treating blood clots in instances where severe health problems arising from the blood clot can develop. While hemostatic agents and topical applications are available for promoting blood clot formation, they are systemically administered, and thus, may suffer from degradation prior to reaching the injury site or require direct access to the injury. Accordingly, there also exits a need for alternative compositions and methods to induce blood clot formation to avoid excessive bleeding in individuals with bleeding disorders or bleeding injuries.

BRIEF DESCRIPTION OF THE DISCLOSURE

The present disclosure is generally directed to compositions and methods for delivery of a target molecule. More particularly, the present disclosure relates to nanoparticle compositions for targeted delivery that sequester a target molecule by non-covalently binding to a site of the target molecule that blocks the activity of the target molecule while it is bound to the nanoparticle and leaving other domains accessible to a substrate. The nanoparticles can be used in methods for targeted delivery of a target molecule for thrombus dissolution and in methods for targeted delivery of a target molecule for inducing blood coagulation.

In one embodiment, delivery systems are provided for plasmin that shield plasmin from alpha 2 antiplasmin (α2- antiplasmin) between the point of injection and a blood clot. Particularly, the delivery system includes a recombinantly produced plasmin bound to a competitive inhibitor molecule and conjugated to a micelle.

In one aspect, the present disclosure is directed to a nanoparticle comprising a lipid molecule; an affinity ligand; and a target molecule; wherein the affinity ligand is covalently coupled to the lipid molecule and wherein the target molecule is reversibly coupled to the affinity ligand by a binding site in the target molecule.

In another aspect, the present disclosure is directed to a method for thrombus dissolution. The method comprises administering a nanoparticle to an individual in need, wherein the nanoparticle comprises a lipid molecule; an affinity ligand; and a target molecule; wherein the affinity ligand is covalently coupled to the lipid molecule and wherein the target molecule is reversibly coupled to the affinity ligand by a binding site in the target molecule.

In one particular aspect, the present disclosure is directed to a method for treating acute vascular thrombosis in an individual in need thereof. In some embodiments of this aspect, the affinity ligand is a benzamidine or derivative thereof.

In another aspect, the present disclosure is directed to a method for inducing blood coagulation. The method comprises administering a nanoparticle to an individual in need, wherein the nanoparticle comprises a lipid molecule; an affinity ligand; and a target molecule; wherein the affinity ligand is covalently coupled to the lipid molecule and wherein the target molecule is reversibly coupled to the affinity ligand by a binding site in the target molecule.

In yet another aspect, the present disclosure is directed to a method for sequestering a target molecule. The method comprises covalently coupling an affinity ligand that specifically binds a target molecule to a lipid molecule to form a lipid molecule-affinity ligand conjugate; preparing a nanoparticle comprising the lipid molecule-affinity ligand conjugate; and attaching the target molecule to the affinity ligand, wherein the target molecule is reversibly coupled to the affinity ligand by a binding site of the target molecule.

In accordance with the present disclosure, compositions and methods have been discovered that surprisingly allow for the treatment of blood clots. The methods of the present disclosure have a broad and significant impact, as they allow for sequestering the activity of a target molecule and delivery to the site of the blood clot where the target molecule is then released in its active form to dissolve the blood clot. In addition, compositions and methods have been discovered that surprisingly allow for inducing the formation of blood clots. The methods of the present disclosure have a broad and significant impact, as they allow for sequestering the activity of a target molecule and delivery to the site of an injury where the target molecule is then released in its active form to induce the formation of a blood clot.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

10A depicts absorbance and fluorescent profiles of p-aminobenzamidine with excitation (solid line) and emission (dashed line) maxima of 294 and 370 nm, respectively. FIG. 10B depicts $K_d$ determination via fluorescence titration of plasmin with increasing concentrations of p-aminobenzamidine. Binding curve was fit by a sigmoid demonstrating a $K_d$=53.5±4.42 μM. All data represents means (±SD) of triplicate experiments.

FIG. 19B raw data with baseline blood clot digestion subtracted), as described in Example 12.

Figure 1:
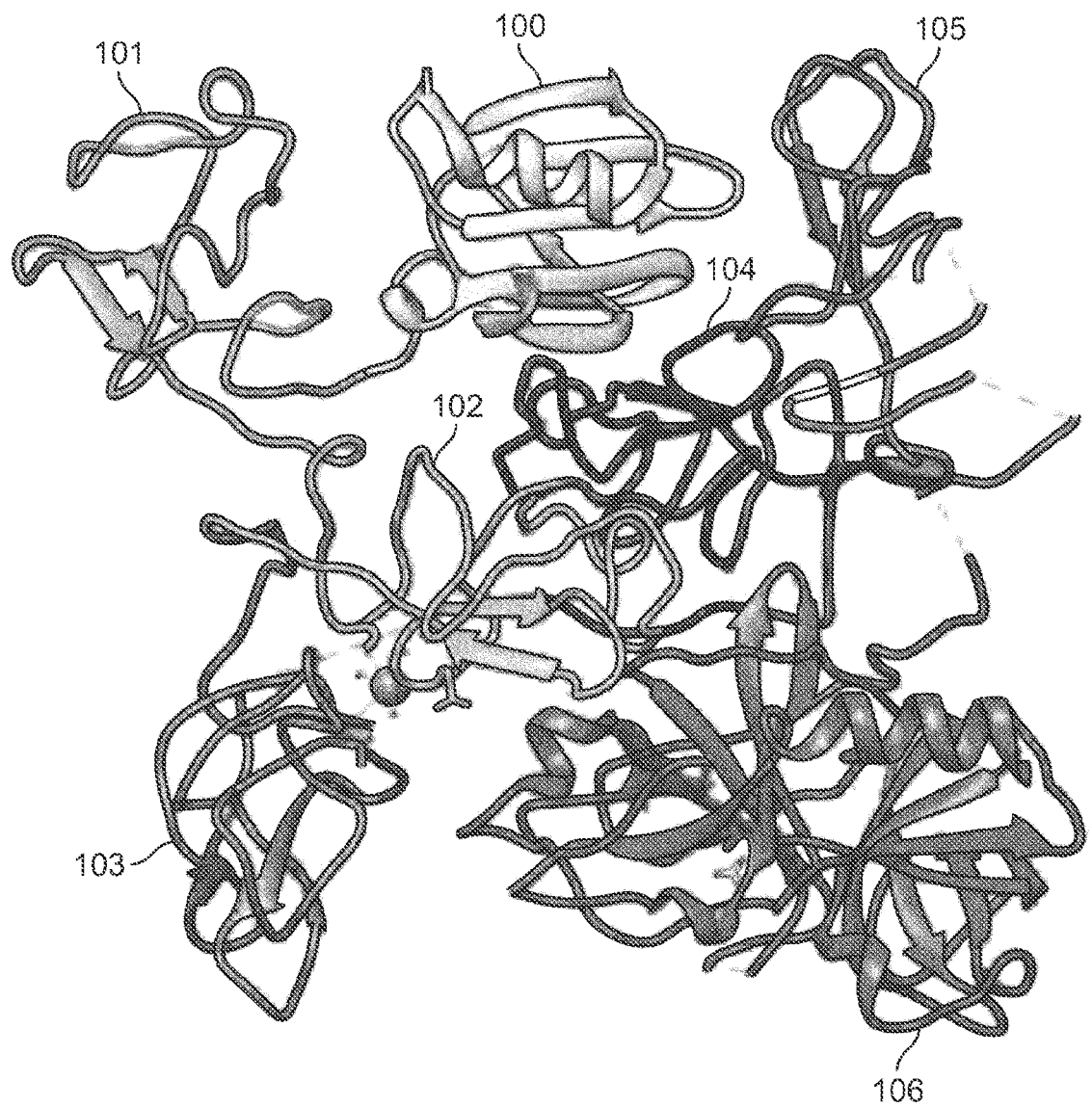
FIG. 1 depicts the crystal structure of full length type II human plasminogen (SEQ ID NO:1; active site serine protease domain is underlined (~residues 560-791) with the Arg561-Val562 activation cleavage site shown in bold.). Highlighted are the different domains including: the pan apple domain (100), Kringle 1-5 (101, 102, 103, 104, 105, respectively), and catalytic domain (106), PDB: 4 DUR. δ-Plasminogen (SEQ ID NO:2) being comprised only of Kringle 1 (101) and the catalytic domain (106).

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, compositions and methods have been discovered that surprisingly allow for the treatment of blood clots. Advantageously, the compositions and methods of the present disclosure allow for sequestering of the activity of a target molecule and targeted delivery of the target molecule to a blood clot where the target molecule is released in its active form to dissolve the blood clot. In addition, compositions and methods have been discovered that surprisingly allow for sequestering of the activity of a target molecule and targeted delivery of the target molecule to a blood vessel injury where the target molecule is released in its active form to induce the formation of blood clots. This delivery methodology differs greatly from other described nanoparticle driven delivery systems in that the target molecule is non-covalently associated to the nanoparticle surface allowing for the delivery of a fully active, unmodified target molecule to the target site that is not possible when using a delivery system that requires covalently conjugating a target molecule to the surface of the nanoparticle.

Nanoparticle Compositions

In one aspect, the present disclosure is directed to a nanoparticle for delivery of a target molecule comprising a lipid molecule; an affinity ligand; and a target molecule; wherein the affinity ligand is covalently coupled to the lipid molecule and wherein the target molecule is reversibly coupled to the affinity ligand by a binding site in the target molecule.

The nanoparticle can be, for example, a micelle, a liposome, a dendrimer, a biodegradable polymer scaffold, a non-biodegradable polymer scaffold, and an inorganic nanoparticle such as a metallic, magnetic, quantum dot or crystalline nanoparticle, or any combination thereof.

Figure 2:
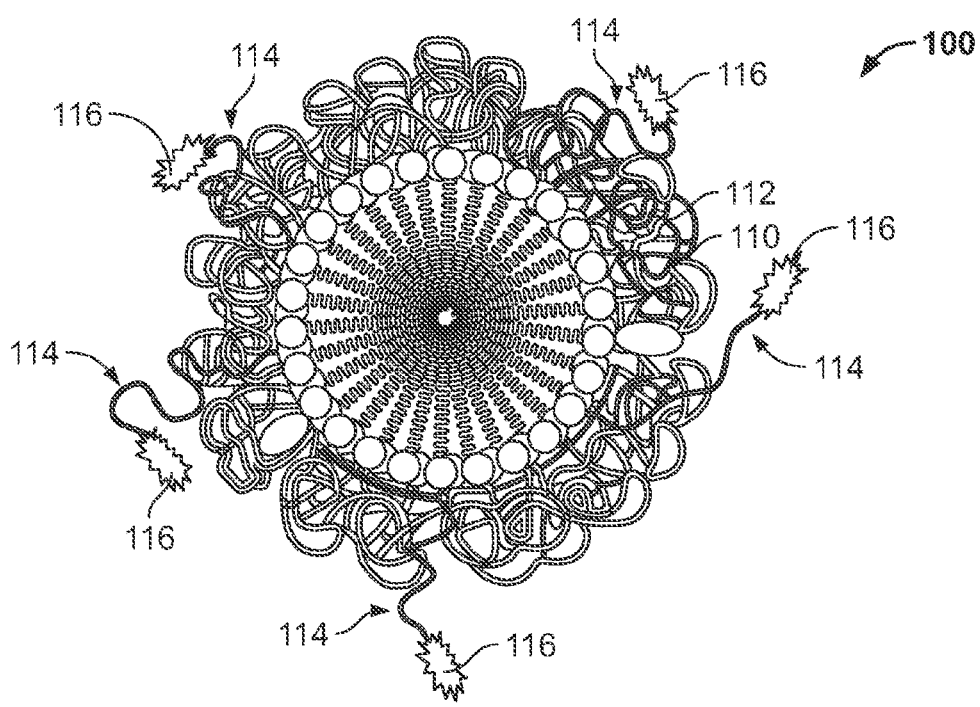
FIG. 2 is a schematic illustration of a micelle nanoparticle of the present disclosure.

FIG. 2 is a cross-section view of a micelle nanoparticle 100 embodiment. The lipid molecules 110 making up micelle nanoparticle 100 are PEGylated with poly(ethylene glycol) 112. FIG. 2 also shows five PEGylated lipid molecules 114 that are conjugated to an affinity ligand 116.

Figure 3:
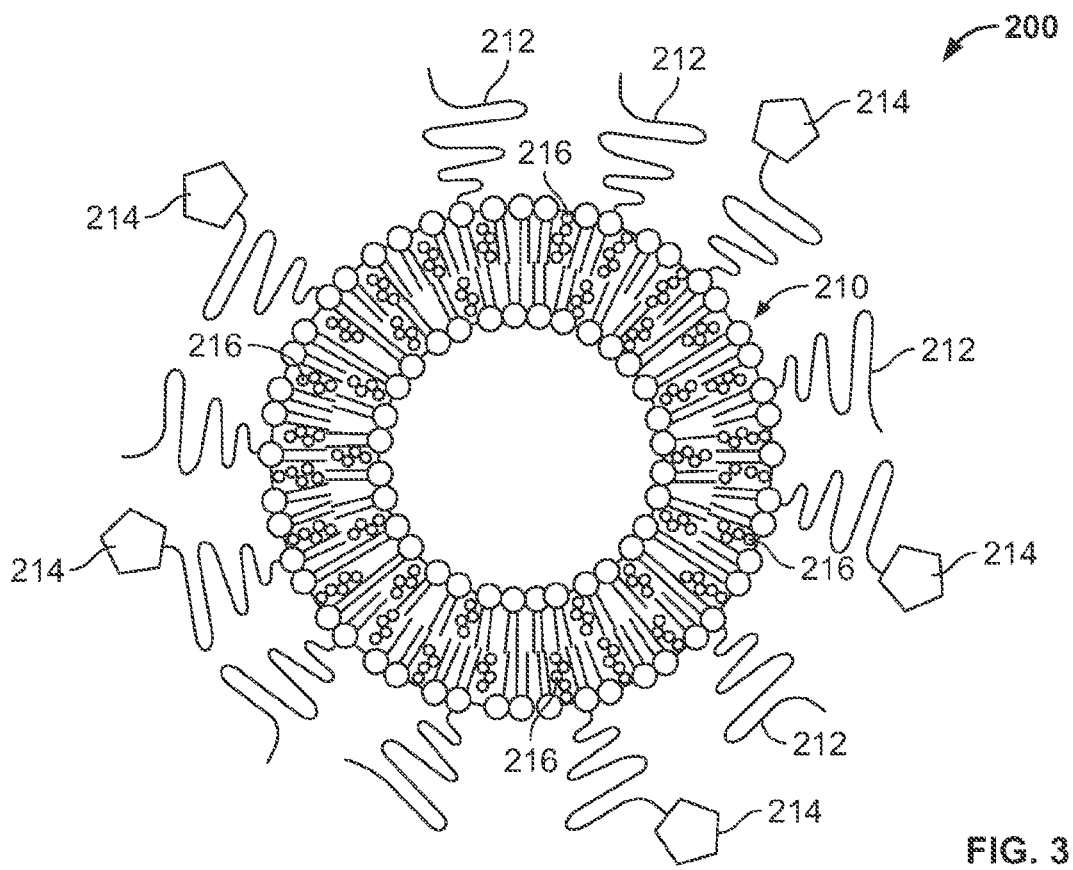
FIG. 3 is a schematic illustration of a liposome nanoparticle of the present disclosure.

FIG. 3 is a cross-section view of a liposome nanoparticle 200 embodiment. The lipid molecules 210 form the liposome nanoparticle 200. Some lipid particles are PEGylated with poly(ethylene glycol) 212. Some lipid particles are PEGylated and conjugated to an affinity ligand 214. Liposome nanoparticle 200 also includes cholesterol 216.

The lipid molecules are amphipathic lipid molecules having a hydrophilic polar group ("head group") and hydrophobic non-polar group ("tail group"). Some or all of the lipid molecules can be phospholipids. Suitable phospholipids are known by those skilled in the art and are commercially available (AVANTI® Polar Lipids, Inc., Alabaster, Ala.). Phospholipids can be, for example, phosphatidylcholine, phosphatidic acid, phosphatidylethanolamine, phosphatidylserine, phosphoinositides including phosphatidylinositol, phosphatidylinositol phosphate, phosphatidylinositol bisphosphate, and phosphatidylinositol triphosphate, and phosphingolipids including ceramide phosphorylcholine, ceramide phosphorylethanolamine, and ceramide phosphoryl lipid. Suitable phospholipids can also include synthetic lipids such as, for example, palmitic acid, organic/inorganic nanoparticles, and co-block polymer-based nanoparticles such as, for example, poly(lactic acid) (PLA), poly(glycolic acid) (PGA), poly(lactide-co-glycolide) (PLGA), poly(ethylene glycol) (PEG), dextran, poly (ε-caprolactone) (PCL), poly (β-benzyl L-aspartate) (PLBA), poly (γ-benzyl L-glutamate) (PLBG), poly (alkyl-cyanoacrylate), poly esters, poly (ortho-esters) (POE), poly-anhydrides (PA), polyamides, and silica. Particularly suitable phospholipids can be phospholipid derivatives such as, for example, natural phospholipid derivatives and synthetic phospholipid derivatives. Phospholipid derivatives can be, for example, 1,2-Didecanoyl-sn-glycero-3-phosphocholine (DDPC); 1,2-Dierucoyl-sn-glycero-3-phosphate (Sodium Salt) (DEPA-NA); 1,2-Dierucoyl-sn-glycero-3-phosphocholine (DEPC); 1,2-Dierucoyl-sn-glycero-3-phosphoethanolamine (DEPE); 1,2-Dierucoyl-sn-glycero-3[Phospho-rac-(1-glycerol) (Sodium Salt) (DEPG-NA); 1,2-Dilinoleoyl-sn-glycero-3-phosphocholine (DLOPC); 1,2-Dilauroyl-sn-glycero-3-phosphate (Sodium Salt) (DLPA-NA); 1,2-Dilauroyl-sn-glycero-3-phosphocholine (DLPC); 1,2-Dilauroyl-sn-glycero-3-phosphoethanolamine (DLPE); 1,2-Dilauroyl-sn-glycero-3[Phospho-rac-(1-glycerol) (Sodium Salt) (DLPG-NA); 1,2-Dilauroyl-sn-glycero-3[Phospho-rac-(1-glycerol) (Ammonium Salt) (DLPG-NH4); 1,2-Dilauroyl-sn-glycero-3-phosphoserine (Sodium Salt) (DLPS-NA); 1,2-Dimyristoyl-sn-glycero-3-phosphate (Sodium Salt) (DMPA-NA); 1,2-Dimyristoyl-sn-glycero-3-phosphocholine (DMPC); 1,2-Dimyristoyl-sn-glycero-3-phosphoethanolamine (DMPE); 1,2-Dimyristoyl-sn-glycero-3[Phospho-rac-(1-glycerol) (Sodium Salt) (DMPG-NA); 1,2-Dimyristoyl-sn-glycero-3[Phospho-rac-(1-glycerol) (Ammonium Salt) (DMPG-NH4); 1,2-Dimyristoyl-sn-glycero-3[Phospho-rac-(1-glycerol) (Sodium/Ammonium Salt) (DMPG-NH4/NA); 1,2-Dimyristoyl-sn-glycero-3-phosphoserine (Sodium Salt) (DMPS-NA); 1,2-Dioleoyl-sn-glycero-3-phosphate (Sodium Salt) (DOPA-NA); 1,2-Dioleoyl-sn-glycero-3-phosphocholine (DOPC); 1,2-Dioleoyl-sn-glycero-3-phosphoethanolamine (DOPE); 1,2-Dioleoyl-sn-glycero-3[Phospho-rac-(1-glycerol) (Sodium Salt) (DOPG-NA); 1,2-Dioleoyl-sn-glycero-3-phosphoserine (Sodium Salt) (DOPS-NA); 1,2-Dipalmitoyl-sn-glycero-3-phosphate (Sodium Salt) (DPPA-NA); 1,2-Dipalmitoyl-sn-glycero-3-phosphocholine (DPPC); 1,2-Dipalmitoyl-sn-glycero-3-phosphoethanolamine (DPPE); 1,2-dipalmitoyl-sn-glycero-3-phosphoethanolamine-N-(glutaryl) (sodium salt) (DPPG-GA); 1,2-Dipalmitoyl-sn-glycero-3[Phospho-rac-(1-glycerol) (Sodium Salt) (DPPG-NA); 1,2-Distearoyl-sn-glycero-3-phosphate (Sodium Salt) (DPPG-NH4); 1,2-Dipalmitoyl-sn-glycero-3-phosphoserine (Sodium Salt) (DPPS-NA); 1,2-Distearoyl-sn-glycero-3-phosphate (Sodium Salt) (DSPA-NA); 1,2-Distearoyl-sn-glycero-3-phosphocholine (DSPC); 1,2-Distearoyl-sn-glycero-3-phosphoethanolamine (DSPE); 1,2-Distearoyl-sn-glycero-3[Phospho-rac-(1-glycerol) (Sodium Salt) (DSPG-NA); 1,2-Distearoyl-sn-glycero-3[Phospho-rac-(1-glycerol) (Ammonium Salt) (DSPG-NH4); 1,2-Distearoyl-sn-glycero-3-phosphoserine (Sodium Salt) (DSPS-NA); Egg-PC (EPC); Hydrogenated Egg PC (HEPC); Hydrogenated Soy PC (HSPC); 1-Myristoyl-sn-glycero-3-phosphocholine (LYSOPC MYRISTIC); 1-Palmitoyl-sn-glycero-3-phosphocholine (LYSOPC PALMITIC); 1-Stearoyl-sn-glycero-3-phosphocholine (LYSOPC STEARIC); 1-Myristoyl-2-palmitoyl-sn-glycero 3-phosphocholine (Milk Sphingomyelin MPPC); 1-Myristoyl-2-stearoyl-sn-glycero-3-phosphocholine (MSPC); 1-Palmitoyl-2-myristoyl-sn-glycero-3-phosphocholine (PMPC); 1-Palmitoyl-2-oleoyl-sn-glycero-3-phosphocholine (POPC); 1-Palmitoyl-2-oleoyl-sn-glycero-3-phosphoethanolamine (POPE); 1-Palmitoyl-2-oleoyl-sn-glycero-3 [Phospho-rac-(1-glycerol)] (Sodium Salt) (POPG-NA);

1-Palmitoyl-2-stearoyl-sn-glycero-3-phosphocholine (PSPC); 1-Stearoyl-2-myristoyl-sn-glycero-3-phosphocholine (SMPC); 1-Stearoyl-2-oleoyl-sn-glycero-3-phosphocholine (SOPC); 1-Stearoyl-2-palmitoyl-sn-glycero-3-phosphocholine (SPPC); and combinations thereof. Particularly suitable phospholipids can also be modified with a water soluble polymer such as poly(ethylene glycol) to form PEGylated phospholipids such as, for example, DSPE-PEG (2000); DSPE-PEG(2000)-amine; and combinations thereof. Phospholipids can also be modified with polymeric sugars such as poly(lactic-co-glycolic acid) (PLGA).

In some embodiments, the lipid molecules of the nanoparticle can be the same chemical species. In other embodiments, the lipid molecules of the nanoparticle can be different chemical species.

In other embodiments, the nanoparticle can further comprise a second lipid molecule (referred to herein as a "bulk lipid"). The concentration of bulk lipid can be between 0 M and about 10 M. The bulk lipid can be a PEGylated lipid molecule. The density of the bulk lipid in the nanoparticle can be from about 100 molecules per square nanometer on the surface of the nanoparticle to about 1 molecule per 20000 square nanometers on the surface of the nanoparticle.

The affinity ligand is covalently coupled to the lipid molecule. The orientation, distribution and density of the affinity ligand (and/or linker when used) are configured to optimize offloading (release) kinetics of the target molecule. The term, "covalently coupled to" is used according to its ordinary meaning as understood by those skilled in the art to refer to the coupling of, connecting of, attaching of, joining of the affinity ligand (and/or linker when used) to the lipid molecule whereby a chemical bond forms between the lipid molecule and the affinity ligand (and/or linker molecule when used). The lipid molecule and the affinity ligand are chemically reacted to form a chemical bond (covalently linked) between the lipid molecule and the affinity ligand. The binding molecule and/or linker can be activated using any number of activating agents including carbodiimides such as, DCC (N,N'-dicyclohexylcarbodiimide), EDC (1-Ethyl-3-(3-dimethylaminopropyl)carbodiimide), HATU (1-[Bis(dimethylamino)methylene]-1H-1,2,3-triazolo[4,5-b]pyridinium 3-oxid hexafluorophosphate), HBTU (1H-Benzotriazol-1-yloxy)(dimethylamino)-N,N-dimethyl-methaniminium hexafluorophosphate), HOAt (1-hydroxy-7-aza-benzotriazole), ethyl 2-cyano-2-(hydroxyimino) acetate, HCTU (O-(1H-6-Chlorobenzo triazole-1-yl)-1,1,3,3-tetramethyluronium hexafluorophosphate), BOP ((Benzotriazol-1-yloxy)tris(dimethylamino)phosphonium hexafluorophosphate), PyBOP ((Benzotriazol-1-yloxy) tripyrrolidinophosphonium hexafluorophosphate), for example, into a better leaving group for attachment to the lipid molecule (see FIG. 15B, for example). In some embodiments, one binding molecule is covalently coupled to the lipid molecules making up the nanoparticle. In other embodiments more than one binding molecule is covalently coupled to the lipid molecules making up the nanoparticle. Similarly, one or more linkers can be covalently coupled to the lipid molecules making up the nanoparticle.

The affinity ligand can be selected from a small molecule (chemical) and a peptide that specifically binds to the target molecule. In particular, the affinity ligand is designed to specifically bind to a binding site of the target molecule. As used herein, "binding site" refers to a site in a target molecule where a binding molecule and/or a portion of a binding molecule can non-covalently and reversibly bind such that the activity of the target molecule is inhibited, modulated, interfered with and/or reduced while the target molecule is bound to the affinity ligand. The binding site of the target molecule can be an active site of the target molecule, a cofactor binding site of the target molecule, a coenzyme binding site of the target molecule, a substrate binding site of the target molecule, an autoinhibitory site of the target molecule, a regulatory site of the target molecule, and any other binding domain on the target molecule. Specific binding of the affinity ligand to the binding site of the target molecule can inhibit, modulate, interfere with and/or reduce the target molecule's activity in a competitive inhibitory manner, an uncompetitive inhibitory manner, a non-competitive inhibitory manner or a partially competitive manner Specific binding of the affinity ligand to the binding site of the target molecule advantageously sequesters the target molecule to inhibit its activity while bound to the nanoparticle. Specific binding of the affinity ligand to the binding site of the target molecule also advantageously orient other domains of the target molecule to be accessible for interacting with the target molecule's substrate. For target molecules having autolysis activities, specific binding of the affinity ligand to the binding site of the target molecule can inhibit, modulate, interfere with and/or reduce autolysis activities that lead to self-inactivation and clearance of the target molecule allowing for improved half-life of the target molecule.

Suitable small molecule affinity ligands can have a molecular weight of from about 50 Daltons to about 5,000 Daltons. Suitable small molecule affinity ligands can contain at least one aryl ring with an attached group containing at least two nitrogen atoms, wherein the nitrogen groups form a triangular structure such as an amidine and wherein one nitrogen atom has a double bond with a carbon atom that is attached to an aryl ring.

Suitable affinity ligands can be, for example, serine protease inhibitors. Particularly suitable affinity ligands can be, for example, serine protease inhibitors that specifically bind to the active site of the serine protease. The serine protease inhibitor can be selected from a small molecule inhibitor, a peptide inhibitor and combinations thereof. Particularly suitable small molecule inhibitors can be, for example, benzamidines. Suitable benzamidines can be, for example, benzamidine, 4-aminobenzamidine, 4-carboxybenzamidine, 4-aminomethyl benzamidine, pentamidine, and combinations thereof (see, Table 1). Other suitable small molecule inhibitors can be, for example, bivalirudin, argatroban ((2R,4R)-1-[(2S)-5-(diaminomethylideneamino)-2-[[(3R)-3-methyl-1,2,3,4-tetrahydroquinolin-8-yl]sulfonylamino]pentanoyl]-4-methyl-piperidine-2-carboxylic acid), melagatran (or its prodrug ximelagatran; ethyl 2-[[(1R)-1-cyclohexyl-2-[(2S)-2-[[4-(N'-hydroxycarbamimidoyl)phenyl]methyl-carbamoyl]azetidin-1-yl]-2-oxo-ethyl]amino]acetate), dabigatran (Ethyl 3-{[(2-[(4-{N-hexyloxycarbonyl carbamimidoyl}phenyl)amino]methyl}-1-methyl-1H-benzimidazol-5-yl)carbonyl] (pyridin-2-yl-amino)propanoate), and combinations thereof. Other suitable small molecule affinity ligand can be, for example, amprenavir ((3S)-oxolan-3-yl N-[(2S,3R)-3-hydroxy-4-[N-(2-methylpropyl) (4-aminobenzene)sulfonamido]-1-phenylbutan-2-yl]carbamate), atazanavir (methyl N-[(1S)-1-[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl] carbamate), darunavir ([(1R,5S,6R)-2,8-dioxabicyclo[3.3.0] oct-6-yl] N-[(2S,3R)-4-[(4-aminophenyl)sulfonyl-(2-methylpropyl)amino]-3-hydroxy-1-phenyl-butan-2-yl] carbamate), fosamprenavir ({[(2R,3S)-1-[N-(2-methylpropyl)(4-aminobenzene)sulfonamido]-3-({[(3S)-oxolan-3- yloxy]carbonyl}amino)-4-phenylbutan-2-yl]
oxy}phosphonic acid), indinavir ((2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-ylmethyl)piperazine-2-carboxamide), lopinavir/ritonavir combination ((2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide and 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate), nelfinavir ((3S,4aS,8aS)—N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide), ritonavir (1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate), saquinavir ((2S)—N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide), tipranavir (N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide), and combinations thereof. Suitable peptide inhibitors can be, for example, serpins, hirudin, bivalirudin, lepirudin, desirudin, and combinations thereof. Other new small molecule affinity ligands and, peptides and peptidomimetics inhibitors are continually being developed as protease inhibitors to combat numerous diseases and illnesses, and can be used with the nanoparticles of the present disclosure.

The nanoparticle also includes a target molecule that is reversibly coupled to the affinity ligand. As used herein, "reversibly coupled" refers to the capability of the target molecule to bind and unbind from the affinity ligand. For example, the target molecule and the affinity ligand can be reversibly coupled by electrostatic attraction, hydrogen bonding, hydrophobic effects and Van der Waals forces. For example, plasmin can bind via its active site to benzamidine and also have the capability to be released from benzamidine when its kringle moieties contact lysine residues on fibrin. Thus, in the absence of fibrin, plasmin remains bound to benzamidine.

In one embodiment, the target molecule is a protein designed to digest blood clots. Suitable target molecules can be proteases, for example. Particularly suitable proteases are natural and synthetic proteases that contain a catalytic triad domain. As known to those skilled in the art, a catalytic triad refers to the three amino acid residues that function together at the center of the active site in enzymes such as, proteases, amidases, esterases, acylases, lipases and β-lactamases. Suitable proteases can be serine proteases, for example. As known by those skilled in the art, serine proteases are enzymes that cleave peptide bonds in proteins, in which a serine amino acid residue serves as the nucleophilic amino acid at the enzyme's active site. Particularly suitable serine proteases can be, for example, plasmin, urokinase, tissue plasminogen activator (plasminogen activator), trypsin, a trypsin like enzyme, batroboxin (reptilase) and combinations thereof. A particularly suitable serine protease is plasmin such as, for example, plasmin and delta plasmin Through recombinant manipulation, the plasmin variant, delta-plasmin (δ-plasmin), has been produced in which K2-K5 have been deleted from full-length plasmin, while retaining the moderate-affinity of K1 to bind fibrin. Elimination of K2-K5 enables the technical feasibility to synthesize, purify and refold active enzyme from an E. coli expression vector.

In one particular aspect of the present disclosure, it has been found that the target molecule plasmin is bind via its active site to the affinity ligand benzamidine and/or its derivatives. In this embodiment, the inhibition of plasmin has the potential application for the improved treatment of various thrombi.

In another embodiment, the target molecule is a protein that promotes blood clot formation. Suitable protein that promotes blood clot formation can be serine proteases that participate in the blood clotting cascade. Particularly suitable serine proteases can be, for example, polyphosphate, kallekreins, nucleic acids, reptilase, tissue factor, kallikrein, factor XII, factor XI, factor XIa, factor XII, factor XIIa, factor X, prothrombin, thrombin, a thrombin like enzyme, batroboxin (reptilase), tissue plasminogen activator, protein C, protein S, protein Z, trypsin, chymotrypsin, elastase, peptidase, subtilisin, and combinations thereof.

The target molecule surface coverage on the nanoparticle can be from 0% to 100% coverage. The surface coverage of the target molecule can be determined by comparing the known number of binding molecules present on the nanoparticle surface and the known amount of target molecules incubated with the nanoparticles. As long as the affinity ligand concentration exceeds the $K_d$ value of the affinity ligand for the target molecule, and there is sufficient space on the nanoparticle for the target molecule to bind, then the percent surface coverage of the nanoparticle can be calculated. The distance from target molecule to target molecule on the nanoparticle can be from about 0.1 nm to about 200 nm.

Suitable target molecules can further contain a second amino acid sequence, small molecule, protein and/or post translational modification that allows the target protein to bind to a component of a thrombus or to molecules associated with formation of a thrombus. The second amino acid sequence, small molecule, protein and/or post translational modification can, for example, bind to a platelet, fibronectin, laminin, vitronectin, Von Willebrand's factor, collagen, integrins and cadherins.

Particularly suitable target molecules contain an active site within a catalytic triad motif.

The nanoparticle can further include cholesterol.

The nanoparticle can further include a second molecule that binds to a component of a thrombus. The second molecule can be, for example, a kringle moiety of plasmin, fibronectin, laminin, vitronectin, an antibody to Von Willebrand's factor, collagen, integrin, cadherin, and combinations thereof.

The nanoparticle can further include a linker. The linker can be coupled to the lipid molecule and the affinity ligand can then be coupled to the linker. Alternatively, the affinity ligand can be coupled to the linker and then the linker can then be coupled to the lipid molecule. The orientation, distribution and density of the linker (and affinity ligand) are configured to optimize offloading (release) kinetics of the target molecule. The linker can also allow for additional tuning of the target molecule delivery by varying the linker composition, varying the rigidity, varying the length, and varying the valency of how many inhibitors can be bound to a single lipid. The linker can extend from 0 nm to about 100 nm, and including from 0 nm to about 30 nm, from the surface of the nanoparticle. Suitable linkers can also be "zero length" linkers and cross-linkers that couple molecules together without adding additional spacer arm atoms between the molecules. The linker can have a surface density on the nanoparticle of from about 100 per square nanometer to about 5000 per square nanometer. The concentration of the linker conjugated inhibitor molecule can be between 0 M and about 1 M. The linker includes a terminal moiety that allows conjugation of the affinity ligand to the linker. The moiety can be any reactive pair where the affinity ligand has a reactive group that can be covalently conjugated to the end of the linker. Suitable chemistries for covalently coupling the linker and the affinity ligand via the terminal moiety can be, for example, ester, amide, thiol, click, carboxyl, hydroxyl, or amine group. A particularly suitable linker can be, for example, a poly(ethylene glycol) linker. The poly(ethylene glycol) linker can have from 1 ethylene glycol unit to about 10,000 ethylene glycol units. The poly(ethylene glycol) linker can extend from about 1 nm to about 100 nm from the surface of the nanoparticle.

The nanoparticle can further include a X—OH ligand. The X—OH ligand functions to cap any amine groups on the lipid molecules that remain following conjugation of the affinity ligand. Suitable X—OH ligands can be any ligand, with or without a linker where the "X" is reactive to the terminal group on the lipid providing a method for capping any remaining reactive groups with an OH group. The hydroxyl group is known particularly for its limited interaction with non-target molecules providing way to prevent non-specific association of the nanoparticle with non-target molecules or molecules. Other functional groups with limited reactivity can also be used to serve this purpose in place of the hydroxyl group.

Lipid molecules having coupled affinity ligands can be dried and mixed in an organic solvent such as chloroform at specific mol ratios with other bulk lipid components such as, for example, HSPC, DPPC, cholesterol, and combinations thereof. The lipid molecules can be redried into a lipid film and used to prepare liposome nanoparticles. In liposome nanoparticles, approximately 50% of the lipid facing the aqueous interior of the liposome will include the affinity ligand.

The nanoparticles can have any desired hydrodynamic diameter. A suitable hydrodynamic diameter can be, for example, from about 1 nanometer (nm) to about 5000 nm. In micelle nanoparticle embodiments, the hydrodynamic diameter can be, for example, from about 1 nm to about 30 nm. In liposome nanoparticle embodiments, the hydrodynamic diameter can be, for example, from about 30 nm to about 1000 nm. Hydrodynamic diameter can be determined by any method known to those skilled in the art such as, for example, dynamic light scattering. The liposome nanoparticle embodiments can include the use of multilamellar, unilamellar or nested liposomes.

In a particularly preferred embodiment, the present disclosure is directed to a nanoparticle including a lipid molecule; an affinity ligand; and plasmin; wherein the affinity ligand is covalently coupled to the lipid molecule and wherein the plasmin is reversibly coupled to the affinity ligand at an active site of the plasmin. For example, plasmin can be bound via its active site to the affinity ligand benzamidine and/or its derivatives to provide the potential application for the improved treatment of various thrombi.

Suitable nanoparticles can be, for example, micelles, liposomes, dendrimers (i.e., any multivalent display of the affinity ligand >2), biodegradable polymer scaffolds and non-biodegradable polymer scaffolds. Suitable lipid molecules are described herein. A particularly suitable lipid molecule can be, for example, DSPE-PEG(2000)-amine.

In other embodiments, the nanoparticle can further comprise a second lipid molecule (referred to herein as a "bulk lipid"). The concentration of bulk lipid can be between 0 M and about 10 M. The bulk lipid can be a PEGylated lipid molecule. The density of the bulk lipid in the nanoparticle can be from about 100 molecules per square nanometer on the surface of the nanoparticle to about 1 molecule per 20000 square nanometers on the surface of the nanoparticle.

Suitable affinity ligand molecules are described herein. A particularly suitable embodiment, the affinity ligand is a benzamidine. The benzamidine affinity ligands are serine protease inhibitors that can specifically bind the active site of plasmin Binding affinity of the benzamidine affinity ligands can be tightly controlled by modifying benzamidine to obtain the benzamidine derivative molecules as depicted in Table 1.

TABLE 1

| Benzamidine Derivative Molecules | |
| --- | --- |
| Plasmin Inhibitor | Structure |
| Benzamidine | $NH_2$—C(=NH)—C$_6$H$_5$ |
| 4-Aminobenzamidine | $NH_2$—C(=NH)—C$_6$H$_4$—$NH_2$ |

TABLE 1-continued

Benzamidine Derivative Molecules

| Plasmin Inhibitor | Structure |
| --- | --- |
| 4-Carboxybenzamidine | [structure of 4-carboxybenzamidine] |
| 4-Aminomethyl Benzamidine | [structure of 4-aminomethyl benzamidine] |
| Pentamidine (Nebupent) | [structure of pentamidine] |

In another particularly suitable embodiment, the affinity ligand is a peptide or peptidomimetic that specifically binds the active site of plasmin Particularly suitable peptides can be for example antibody molecules that specifically bind to the active site of plasmin. Antibodies can be for example, polyclonal antibodies and monoclonal antibodies. Antibodies can also be chimeric antibodies, humanized antibodies, antigen binding fragments (Fab), antibody variable domains (Fv), single chain variable fragments (scFv), and complement determining regions (CDRs). Antibodies to the active site of plasmin can be generated using methods known to those skilled in the art.

Plasmin is a fibrinolytically/thrombolytically active serine protease. Formation of fibrinolytically/thrombolytically active plasmin occurs upon activation of plasminogen. Plasminogen is activated by proteolytic cleavage into a heavy chain comprising the 5 kringle domains and a light chain comprising the catalytic domain Both chains are held together by two disulfide bonds. After activation, an autolytic cleavage removes an N-terminal segment from the heavy chain (78 amino acids of human plasmin; 77 amino acids of bovine plasmin) that can be further autocatalytically cleaved between kringle domains 3 and 4, (see, Christensen et al. 1995, Biochem. J. 305, 97-102). Activation of plasminogen to plasmin, triggered by the cleavage of the R561-V562 peptide bond in human plasminogen, induces a large conformational change in the light chain resulting in the activation of the catalytic triad within the light chain.

Suitable plasmin can be, for example, plasmin, mini-plasmin, micro-plasmin and delta plasmin. Delta plasmin is a recombinant version of plasmin in which kringle domain 1 is linked directly with the catalytic domain. Plasmin and delta-plasmin are particularly suited proteins, as they contain kringle domains that bind specifically to fibrin, found extensively throughout blood clots. In this regard the plasmin decorated nanoparticle functions as a targeted nanoparticle delivery system to selectively bind and lyse blood clots.

The monovalent binding affinity of plasmin for 4-carboxybenzamdine, as determined by S2251 competitive binding inhibition assays, is 292.47±6.50 µM. The multivalent interaction promotes the plasmin to remain bound to the nanoparticle surface in the absence of a blood clot. Upon multivalent binding of the kringle domains to the clot surface, plasmin releases from the nanoparticle surface as the multivalent expression of fibrin on the clot surface greatly exceeds that of the multivalent presentation of the conjugated affinity ligand on the nanoparticle surface. Because the inhibitory binding affinity of the affinity ligand is comparable to the monovalent affinity of the plasmin kringle domain for fibrin, the local overexpression of fibrin drives the kinetics resulting in offloading (release) of the plasmin to the clot surface allowing for site-specific clot (thrombus) dissolution.

The nanoparticles can further include cholesterol.

The nanoparticles can further include a second molecule that binds to a component of a thrombus. The second molecule can be, for example, a kringle moiety of plasmin, fibronectin, laminin, vitronectin, an antibody to Von Willebrand's factor, collagen, integrin, cadherin, and combinations thereof.

The nanoparticles can further include a linker as described herein. A particularly suitable linker can be, for example, a poly(ethylene glycol) linker.

The nanoparticles can further include an X—OH ligand as described herein.

The nanoparticles have any desired hydrodynamic diameter as described herein.

In another particularly suitable embodiment, the present disclosure is directed to a nanoparticle including a lipid molecule; an affinity ligand; and thrombin; wherein the affinity ligand is covalently coupled to the lipid molecule and wherein the thrombin is reversibly coupled to the affinity ligand at an active site of the thrombin.

Thrombin is a serine protease that converts soluble fibrinogen into insoluble strands of fibrin, as well as catalyzing many other coagulation-related reactions. The thrombin is reversibly coupled to the affinity ligand meaning it is capable of being bound by its active site to the affinity ligand and capable of unbinding when its exosite binding to GPIb on platelets.

In other embodiments, the nanoparticle can further comprise a second lipid molecule (referred to herein as a "bulk lipid"). The concentration of bulk lipid can be between 0 M and about 10 M. The bulk lipid can be a PEGylated lipid molecule. The density of the bulk lipid in the nanoparticle can be from about 100 molecules per square nanometer on the surface of the nanoparticle to about 1 molecule per 20000 square nanometers on the surface of the nanoparticle.

Suitable affinity ligands are described herein. A particularly suitable embodiment, the affinity ligand is a benzamidine inhibitor molecule. The benzamidine affinity ligands are serine protease inhibitors that can specifically bind the active site of thrombin. Binding affinity of the benzamidine affinity ligand can be tightly controlled by modifying benzamidine to obtain the benzamidine derivative molecules as depicted in Table 1.

In another particularly suitable embodiment, the affinity ligand is a peptide or peptidomimetic that specifically binds the active site of thrombin. Particularly suitable peptides can be for example antibody molecules that specifically bind to the active site of plasmin Antibodies can be for example, polyclonal antibodies and monoclonal antibodies. Antibodies can also be chimeric antibodies, humanized antibodies, antigen binding fragments (Fab), antibody variable domains (Fv), single chain variable fragments (scFv), and complement determining regions (CDRs). Antibodies to the active site of plasmin can be generated using methods known to those skilled in the art.

The nanoparticles can further include cholesterol.

The nanoparticles can further include a second molecule that binds to a component of a thrombus. The second molecule can be, for example, a kringle moiety of plasmin, fibronectin, laminin, vitronectin, an antibody to Von Willebrand's factor, collagen, integrin, cadherin, and combinations thereof.

The nanoparticles can further include a linker as described herein. A particularly suitable linker can be, for example, a poly(ethylene glycol) linker.

The nanoparticles can further include an X—OH ligand as described herein.

The nanoparticles have any desired hydrodynamic diameter as described herein.

Nanoparticle Preparation

In another aspect, the present disclosure is directed to a method of preparing a nanoparticle for delivery of a target molecule. The method includes functionalizing a nanoparticle selected from micelles, liposomes, dendrimers, and polymeric scaffolds by conjugating an affinity ligand to the nanoparticle to prepare a functionalized nanoparticle; and coupling a target molecule with the functionalized nanoparticle, wherein the target molecule associates with the affinity ligand by a binding site of the target molecule.

In one embodiment, the nanoparticle is a lipid micelle nanoparticle. The formation of lipid micelles typically includes the evaporation of the organic solvent in which the lipid is stored. The "dried" lipid film can then be rehydrated with an aqueous buffer or water. Micelles will form by self-assembly. Tip sonication can also be used to induce a more rapid micelle formation. Dynamic light scattering (DLS) can be performed to verify micelle formation and allow for accurate measurement of the nanoparticle hydrodynamic diameter in solution. An adsorption spectrum of the sample (200-350 nm) can be taken to document a baseline absorbance to allow for accurate quantification of affinity ligand conjugation yield. Coupling efficiency of the affinity ligand to the micelle nanoparticle can be determined by obtaining baseline measurements of the lipid concentration, the dilution factor, and the total volume of the sample prior to coupling the affinity ligand to the lipid molecule.

Following formation of nanoparticles with affinity ligands, the target molecule is added. The target molecule associates with the affinity ligand via the binding site of the target molecule. A multivalent interaction between the target molecule binding site and the affinity ligand promotes the target molecule to remain bound to the nanoparticle surface in the absence of the target molecule's substrate. Plasmin and delta-plasmin are uniquely suited proteins for use in this delivery technique as they contain kringle domains that bind specifically to fibrin, found extensively throughout blood clots. In this regard the plasmin decorated nanoparticle functions as a targeted nanoparticle delivery system to selectively bind and lyse blood clots. Upon multivalent binding of the kringle domains to the clot surface, plasmin will be released from the nanoparticle surface as the multivalent expression of fibrin on the clot surface will greatly exceed that of the multivalent presentation of affinity ligands on the nanoparticle surface. Since the inhibitory binding affinity of the affinity ligand such as, for example, 4-carboxybenzamdine, is comparable to the monovalent affinity of the plasmin kringle domain for fibrin, the local overexpression of fibrin drives the kinetics resulting in the offloading (release) of the plasmin to the clot surface allowing for site-specific clot dissolution. In a similar manner, a nanoparticle with thrombin reversibly attached via binding of its binding site to an affinity ligand is offloaded by the thrombin exocite binding to GPIb located on platelets. This delivery methodology differs greatly from other described nanoparticle driven protein delivery systems in that the target molecule is non-covalently associated with the nanoparticle surface allowing for fully active, unmodified, delivery to the target site that is not possible when using a delivery system that requires covalently conjugating a target molecule to the surface of the nanoparticle.

In another embodiment, the nanoparticles are liposome nanoparticles. Liposome nanoparticles can be formed from dried micelle nanoparticles conjugated with an inhibitor molecule. To form liposome nanoparticles, lipids are rehydrated and resolubilized following the procedure described below by mixing lipids conjugated with an affinity ligand in an organic solvent such as, for example, chloroform. Other bulk lipid components such as, for example, HSPC, DPPC, DSPE-PEG(2000), cholesterol, and combinations thereof can be mixed at specific mole ratios providing for a homogenous mixture of all components followed by evaporation of the organic solvent as described herein. The dried lipid is then rehydrated in a suitable buffer. Suitable hydration buffers can be, for example, distilled water, buffer solutions, saline, and nonelectrolytes such as sugar solutions. During rehydration, there is no hydration repulsion as lipid particles approach one another to repel the approaching particles and the two membranes fall into an energy well where they adhere and form aggregates. The aggregates settle out of solution as large flocculates which will disperse on agitation but reform upon sitting. The product of hydration is the formation of large, multilamellar vesicles with each lipid bilayer separated by a water layer. The large, multilamellar vesicles can be sized by a variety of techniques known to those skilled in the art such as, for example, sonication, extrusion and freeze/thaw cycles. Unilamellar liposome formation is performed using methods known to those skilled in the art such as, for example, lipid extrusion by forcing the rehydrated lipid sample through a filter (e.g., polycarbonate track etched membrane). Extrusion is generally performed at a temperature above the gel-liquid crystal transition temperature of the lipids being used to form the liposomes.

The conjugation method for coupling the affinity ligand to the lipid and purification technique as described in the micelle formation and conjugation protocol below can be followed. Liposomes do not have a critical micelle concentration, and therefore, remain intact regardless of total lipid concentration. Liposomes can also be formed with other functionalized lipids in the exact same manner taking care to calculate the appropriate mole ratios to attain the desired outward facing functionalized lipid concentrations.

In another embodiment, the functionalized affinity ligand-lipid conjugate can be synthesized prior to nanoparticle formation. The affinity ligand-conjugated, or functionalized, lipid can then be purified and utilized at the desired mole ratio in any micelle or liposome formulation. Methods for synthesis and purification can be, for example, solution phase coupling using various coupling agents in various organic and aqueous solvents, solid phase synthetic methods, precipitation and reverse phase chromatography purification procedures.

The method can further include adding a carboxylic acid activating agent such as, for example, 1-ethyl-3-(3-dimethylaminopropyl)carbodiimide (EDC), N-hydroxysuccinimide (NHS) and combinations thereof. The carboxylic acid activating agent functions as a leaving group for coupling the inhibitor molecule to the lipid molecule.

The method can further include purification of the nanoparticles, following conjugation to the preformed nanoparticle, using methods known to those skilled in the art. Suitable purification methods of intact nanoparticles include, for example, chromatography, centrifugation, tangential flow filtration, and dialysis. As understood by those skilled in the art, the selection of the purification technique depends upon many factors including: nanoparticle composition, size, critical micelle concentration, the synthetic chemistry used, and the conjugated functional group employed.

The method can further include capping unconjugated amine groups on the lipid particle by reacting the functionalized lipid particle with an X—OH ligand as described herein.

To verify formation of the lipid nanoparticle, dynamic light scattering can be performed. Dynamic light scattering allows for determining the hydrodynamic diameter of the lipid particle in solution. An adsorption spectrum (200-350 nm) can also be obtained to determine a baseline absorbance to allow for quantifying conjugation yield as well as determining lipid/nanoparticle concentration.

After the affinity ligand is coupled to the lipid nanoparticle, the functionalized lipid nanoparticle can be purified using methods known to those skilled in the art. For example, the functionalized lipid nanoparticle can be purified using liquid chromatography.

The method can further include the addition of cholesterol.

The method can further include the addition of a second molecule that binds to a component of a thrombus. The second molecule can be, for example, a kringle moiety of plasmin, fibronectin, laminin, vitronectin, an antibody to Von Willebrand's factor, collagen, integrin, cadherin, and combinations thereof.

The method can further include the addition of a linker as described herein. The linker can be conjugated to the lipid molecule and the affinity ligand can then be conjugated to the linker. A particularly suitable linker can be, for example, a poly(ethylene glycol) linker.

Once the affinity ligand-lipid nanoparticles are formed, a target molecule can be added. The addition of the target molecule to the functionalized nanoparticles will facilitate association of the target molecule to the outer surface of the nanoparticle through binding of the affinity ligand.

As understood by those skilled in the art, salt concentration and pH should be monitored when reversibly coupling the target molecule with the affinity ligand. For example, a high salt concentration or a pH far outside of the neutral range may result in unfavorable binding conditions and prevent the target molecule from associating with the affinity ligand of the nanoparticle.

The nanoparticle delivery system and methodology differs greatly from other described nanoparticle driven protein delivery systems in that the target molecule is non-covalently associated to the nanoparticle surface allowing for fully active, unmodified, delivery to a target site that is not possible when using a delivery system that requires covalently conjugating a molecule to the surface of the nanoparticle or a delivery system that encapsulates a molecule within a nanoparticle.

Methods of Using Nanoparticles

In another aspect, the present disclosure is directed to a method for thrombus dissolution. The method includes administering a nanoparticle to an individual in need, wherein the nanoparticle comprises a lipid molecule; an affinity ligand; and a target molecule; wherein the affinity ligand is covalently coupled to the lipid molecule and wherein the target molecule is reversibly coupled to the affinity ligand by a binding site of the target molecule.

The target molecule is a molecule that can digest a blood clot. Suitable molecules that can digest a blood clot can be, for example, plasmin, tissue plasminogen activator, urokinase, factor XIa, factor XIIa, and combinations thereof. In one particularly, suitable embodiment, the target molecule is plasmin or δ-plasmin and the affinity ligand is benzamidine and/or benzamidine derivatives.

The nanoparticle is administered to an individual in need. As used herein, "individual in need" refers to a subset of individuals in need of treatment/protection from thrombosis. Some individuals that are in specific need of treatment may include subjects who are susceptible to, or at elevated risk of, experiencing heart attack, stroke, deep vein thrombosis, and pulmonary embolism. Individuals can be susceptible to, or at elevated risk of, experiencing symptoms of heart attack, stroke, deep vein thrombosis, and pulmonary embolism due to family history, age, environment, and/or lifestyle. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein for certain diseases, disorders or conditions.

The term "administering" as used herein includes all means of introducing the nanoparticles described herein to the individual. A particularly suitable administration route is intravenous (IV). The nanoparticles described herein may be administered in unit dosage forms and/or formulations containing conventional nontoxic pharmaceutically-acceptable carriers, adjuvants, and vehicles.

The method can further include co-administration of the nanoparticle with an alpha 2 antiplasmin inhibitor. Suitable alpha 2 antiplasmin inhibitors can be, for example, peptides. Co-administration with alpha 2 antiplasmin can transiently improve plasmin serum half-life to further increase treatment efficiency. The alpha 2 antiplasmin peptides can be mixed into the delivery vehicle and coinfused with the nanoparticles. Clot dissolution potential of plasmin can be augmented by co-infusion of heparin, low molecular weight heparins, fondaparinux, inhibitors of thrombin (e.g., dabigatran etixilate), inhibitors of factors Xa (e.g., rivaroxaban, apixaban, edoxaban), inhibitors of cyclooxygenase I and II (including acetyl salicylic acid and ketorolac), thrombin receptor antagonists (e.g., vorpaxar, atopaxar), inhibitors of adenosine diphosphate receptors (e.g. $P2Y_{12}$ antagonists prasugrel, clopidigrel, ticagrelor, cangrelor), phosphodiesterase inhibitors (e.g., dypyridamole, cilostazol) GIIbIna antagonists (e.g., abciximab, eptifibatide and tirofiban) and various monoclonal antibodies targeted against von Willebrand's factor, and glycoproteins involved in platelet adhesion.

In another aspect, the present disclosure is directed to a method for inducing blood coagulation. The method includes administering a nanoparticle to an individual in need, wherein the nanoparticle comprises a lipid molecule; an affinity ligand; and a target molecule; wherein the affinity ligand is covalently coupled to the lipid molecule and wherein the target the target molecule is reversibly coupled to the affinity ligand at a binding site of the target molecule.

The target molecule is a molecule that can induce blood clot formation. Suitable target molecules for inducing blood clot formation can be, for example, polyphosphate, kallekreins, nucleic acids, reptilase, tissue factor, kallikrein, factor XII, factor XI, factor XIa, factor XII, factor XIIa, factor X, prothrombin, thrombin, a thrombin like enzyme, batroboxin (reptilase), tissue plasminogen activator, protein C, protein S, protein Z, trypsin, chymotrypsin, elastase, peptidase, subtilisin and combinations thereof.

The nanoparticle is administered to an individual in need thereof. As used herein, "individual in need" refers to a subset of individuals in need of treatment/protection from excessive bleeding. Some individuals that are in specific need of treatment may include subjects who are susceptible to, or at elevated risk of, experiencing excessive bleeding such as, for example, individuals with hemophilia, individuals with Von Willebrand disease and trauma patients. Individuals can be susceptible to, or at elevated risk of, experiencing symptoms of excessive bleeding due to family history, age, environment, and/or lifestyle. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein for certain diseases, disorders or conditions.

The term "administering" as used herein includes all means of introducing the nanoparticles described herein to the individual. A particularly suitable administration route is intravenous (IV). The nanoparticles described herein may be administered in unit dosage forms and/or formulations containing conventional nontoxic pharmaceutically-acceptable carriers, adjuvants, and vehicles.

Nanoparticles for Sequestering a Target Molecule

In another aspect, the present disclosure is directed to a method for sequestering a target molecule. The method includes covalently coupling an affinity ligand that specifically binds a target molecule to a lipid molecule to form a lipid molecule-affinity ligand conjugate; preparing a nanoparticle comprising the lipid molecule-affinity ligand conjugate; and attaching the target molecule to the affinity ligand, wherein the target molecule is reversibly coupled to the affinity ligand by a binding site of the target molecule.

The nanoparticle can be a micelle, a liposome, a dendrimer, a biodegradable polymeric scaffold and a non-biodegradable polymeric scaffold as described herein.

Suitable lipid molecules, affinity ligands and target molecules are described herein.

The affinity ligand is designed to specifically bind to a binding site of the target molecule as described herein. Specific binding of the affinity ligand to the binding site of the target molecule advantageously sequesters the activity of the target molecule while the target molecule is bound to the nanoparticle. Specific binding of the affinity ligand to the target molecule also advantageously orients other domains of the target molecule to be accessible for interacting with the target molecule's substrate. For target molecules having autolysis activities, specific binding of the affinity ligand to the target molecule can inhibit autolysis activities that lead to self-inactivation and clearance of the target molecule allowing for improved half-life of the target molecule. Administering the affinity ligand conjugated nanoparticle without a target molecule bound can allow the nanoparticle to advantageously sequester a target molecule in vivo to minimize fibrinolysis such as demonstrated in Example 11.

Delivery Systems Using the Nanoparticles

The present disclosure is further directed to delivery systems for delivering plasmin that shield the plasmin from alpha 2 antiplasmin (α2-antiplasmin) between the point of injection and a blood clot. Antiplasmin binds to plasmin or delta plasmin in a rapid two-step process, first at the enzyme's lysine binding site, followed by covalent binding to the serine in the active site. This avid binding essentially destroys all plasmin in human blood, thus preventing the ability to deliver the enzyme from a peripheral vein, such as the brachial vein, for the purpose of dissolution of blood clots in the lung or arterial circulation. To overcome this inhibition, plasmin must either be delivered by a catheter placed in or near the clot, or the plasmin must be carried or shielded from antiplasmin and other neutralizing proteins while in transit in the blood. Particularly, the delivery system of the present disclosure includes a recombinantly produced plasmin bound to a competitive inhibitor molecule, such as benzamidine and its derivatives (see Table 1), conjugated to a micelle (or liposome). Particularly, it has been found that plasmin, and in particular delta plasmin, can be bound to a competitive inhibitor molecule, conjugated to a micelle, and can be delivered through moving human plasma to cause clot lysis in an in-vitro model of pulmonary embolism (PE).

The disclosure will be more fully understood upon consideration of the following non-limiting Examples.

EXAMPLES

Materials

Plasmin from human plasma, benzamidine, 4-aminobenzamidine dihydrochloride, 4-carboxybenzamidine hydrochloride, 4-aminomethyl benzamidine dihydrochloride, and pentamidine isethionate as well as all other organic solvents, small molecules and buffer producing salts were purchased from Sigma-Aldrich (St. Louis, Mo.). Low binding UV 96-well plates in which the binding titrations and enzymatic assays were performed in were purchased from Thermo Scientific (Rockford, Ill.). Lysine Sepharose and Benzamidine Sepharose were purchased from GE Healthcare (Pittsburgh, Pa.). Chromogenic substrate for plasmin activity tests and determination of kinetic characteristics, S-2251, was purchased from Chromogenix (Orangeburg, N.Y.). All lipids, the extrusion apparatus and polycarbonate track etched membranes were purchased from Avanti Polar Lipids (Alabaster, Ala.). Absorbance and fluorescent emission measurements were made using a SpectraMax Plus 96 well plate reader from Molecular Devices (Sunnydale, Calif.). All measurements were carried out in triplicate and data represents means±standard deviations.

δ-Plasmin Production. δ-Plasmin was produced using a modification of the method by Hunt et al., Simplified recombinant plasmin: Production and functional comparison of a novel thrombolytic molecule with plasma-derived plasmin, Thromb. Haemost. 100 (2008) 413-419. Briefly, δ-plasminogen zymogen was expressed from a T7 E. coli expression system containing the K2-K5 deleted human plasminogen sequence inserted into a pET 24b(+) vector (Novagen; San Diego, Calif.) between the NdeI and BamHI sites. The δ-plasminogen gene, under lac operon control, was expressed with Isopropyl δ-D-thiogalactopyranoside (IPTG). Expressed zymogen was purified with Lysine Sepharose, refolded and activated with streptokinase, and purified by affinity chromatography using Benzamidine Sepharose.

General Methods

Extinction Coefficient Determination.

The small molecule inhibitors were precisely weighed out and absorbance spectrums from 200-350 nm were taken on a Molecular Devices SpectraMax Plus 96 well plate reader. Absorbance maxima and extinction coefficients were calculated in PBS pH 7.4 at 25° C. and used in subsequent binding and inhibition assays. These extinction coefficients can then also be used to determine the concentration of conjugated inhibitor the nanoparticles as well as to determine percent conjugation yield comparing inhibitor concentration to the known lipid concentrations.

Enzyme Kinetic and Inhibition Assays.

All enzymatic assays were conducted in phosphate buffered saline (PBS, pH 7.4) at 25° C. on a Molecular Devices SpectraMax Plus 96 well plate reader. The S-2251 assay took advantage of a shift in absorbance of the substrate upon cleaving that could be monitored at a wavelength of 405 nm to determine enzyme kinetics as well as competitive inhibition Ki values for plasmin and its derivatives. $K_M$, $V_{max}$ and $K_{cat}$ were determined using a Lineweaver-Burke plot in which the concentration of plasmin (1.0 µg/mL) was held constant across a range of S-2251 substrate concentrations (0-750 µM) where the y-intercept=$1/V_{max}$ and slope=$K_M/V_{max}$. Initial velocities were determined by the slope of the first 60 seconds of reaction with the S-2251 substrate. All experiments were carried out in triplicate and data represents means plus or minus standard deviations.

Inhibition Assays:

Inhibition assays were carried out at a fixed plasmin concentration in the presence of a range of small molecule inhibitor concentrations from (0-1500 µM) and at least three different S-2251 substrate concentrations ranging from (0-750 µM). Ki values for both full length/native plasmin (sigma plasmin) and delta-plasmin for the small molecule inhibitors and nanoparticles were calculated based on the x-axis value at the negative intersection point of the inhibition curves at the different S-2251 substrate concentrations at a constant plasmin concentration. All experiments were carried out in triplicate and data represents means plus or minus standard deviations.

Fluorescence Titration Dissociation Constant ($K_d$) Assay.

Plasmin was titrated with increasing concentrations of 4-aminobenzamidine from 0-1000 µM in PBS buffer at pH 7.4. By monitoring the increase in fluorescence emission (excitation 280 nm, emission at 370 nm) from 4-aminobenzamdine associated plasmin, a direct determination of its dissociation constant ($K_d$) can be made. Fitting the data to a sigmoid the $K_d$ value for 4-aminobenzamidine to sigma plasmin is the concentration of inhibitor at which 50% (or 0.5 or half maximum fluorescent emission is reached) intersects with the fit.

Example 1

In this Example, the predicted kinetic characteristics of plasmin and delta-plasmin were compared. $K_M$, $V_{max}$ and $K_{cat}$ were determined for both full length plasmin and delta plasmin using a Lineweaver-Burke plot in which the concentration of plasmin was held constant across a range of S-2251 substrate concentrations (0-750 µM). Initial velocities for each data point were determined by the slope of the first 60 seconds of reaction with the S-2251 substrate following absorbance at 405 nm. When plotted in the form 1/substrate concentration vs $1/V_0$ the y-intercept=$1/V_{max}$ and slope=$K_M/V_{max}$.

Figure 4A:
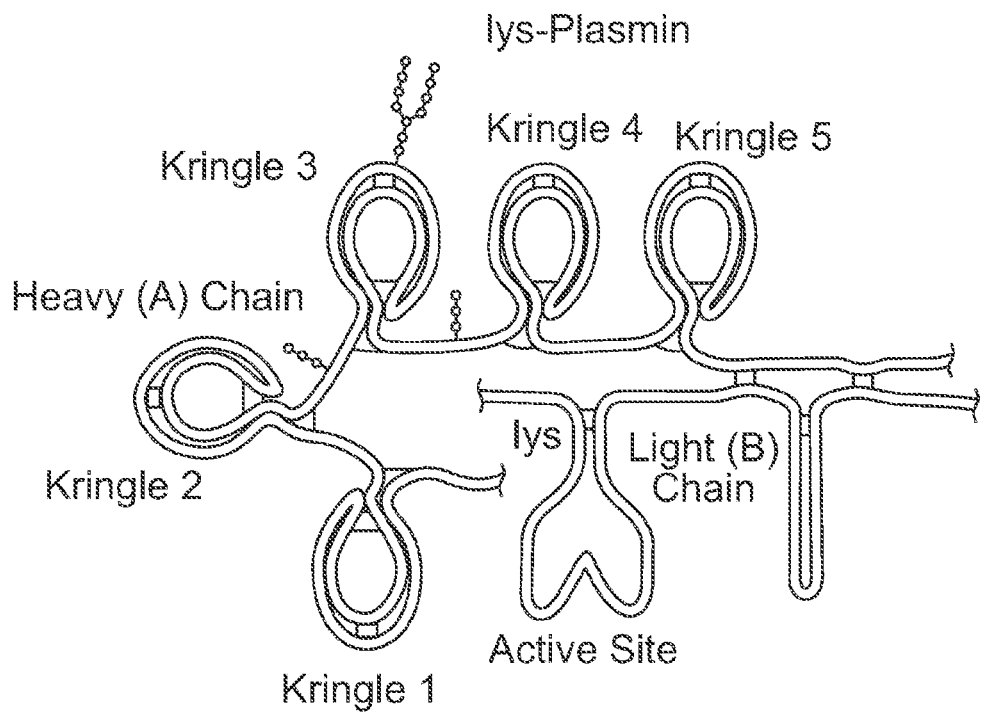
FIG. 4A is a schematic illustration of plasmin.
Figure 4B:
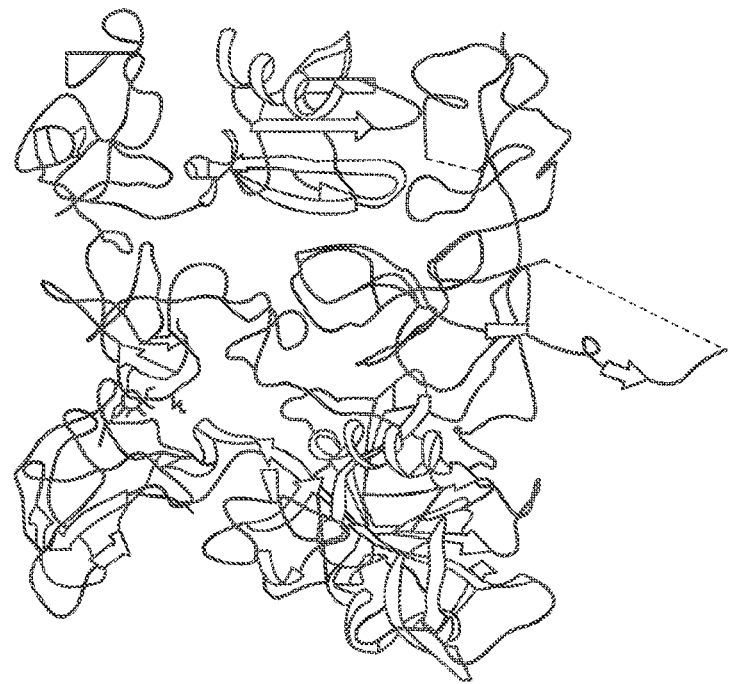
FIG. 4B is an illustration of the molecular structure of plasmin.
Figure 5A:
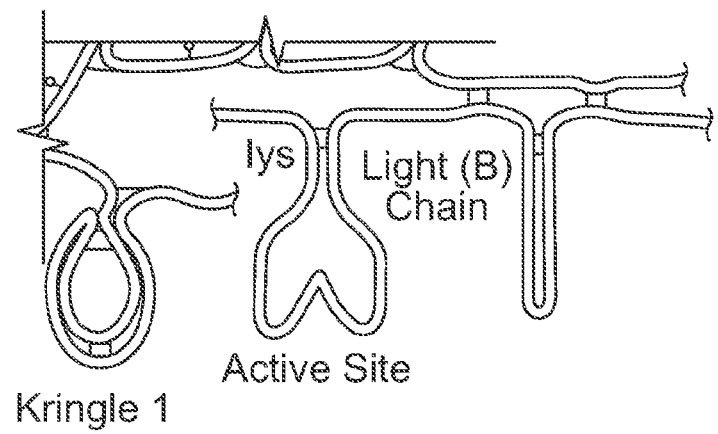
FIG. 5A is a schematic illustration of delta plasmin.
Figure 5B:
FIG. 5B is an illustration of the molecular structure of delta plasmin.

As illustrated in FIGS. 4A and 5A, native plasmin has five kringle domains whereas delta-plasmin is a mutant form containing only one kringle domain. The $K_m$ and $K_{cat}$ for the two forms of plasmin were determined utilizing an S2251 chromogenic substrate.

Figure 6A:
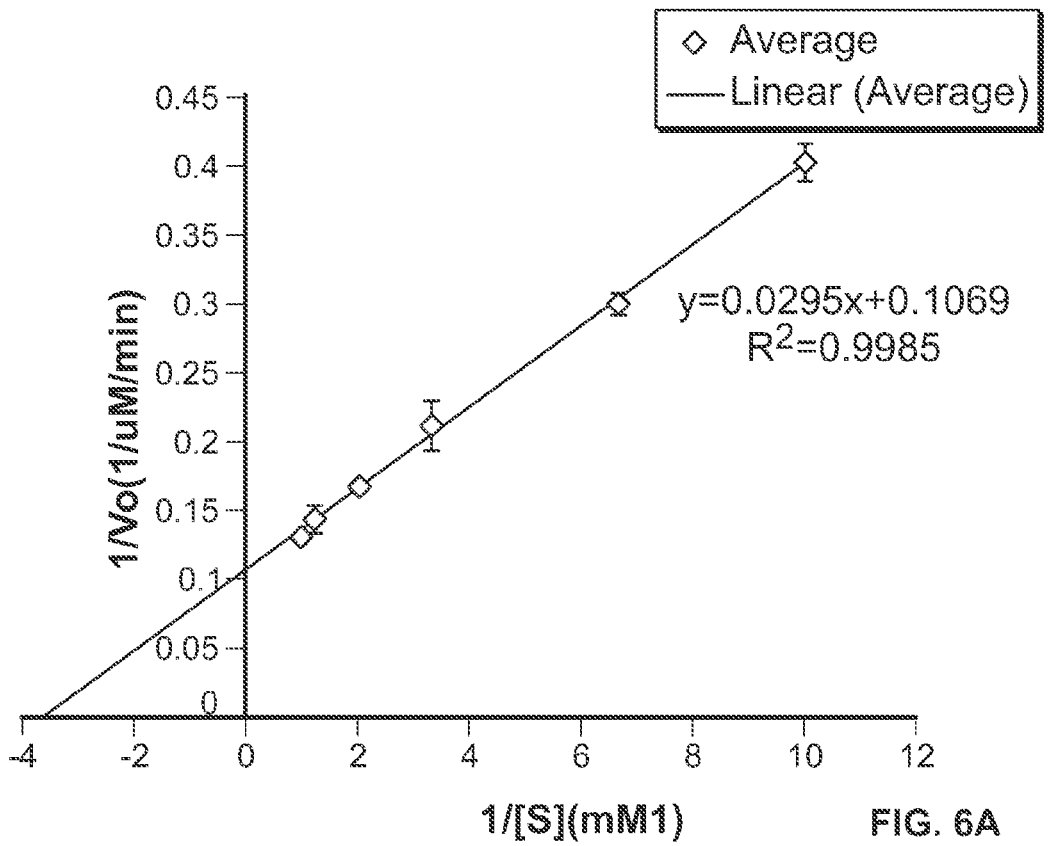
FIG. 6A is a graph depicting the $K_M$ and $K_{cat}$ determination of wild-type plasmin, as described in Example 1. $K_M$=268.78±19.12 μM, $K_{cat}$=770.48±41.73 l/min
Figure 6B:
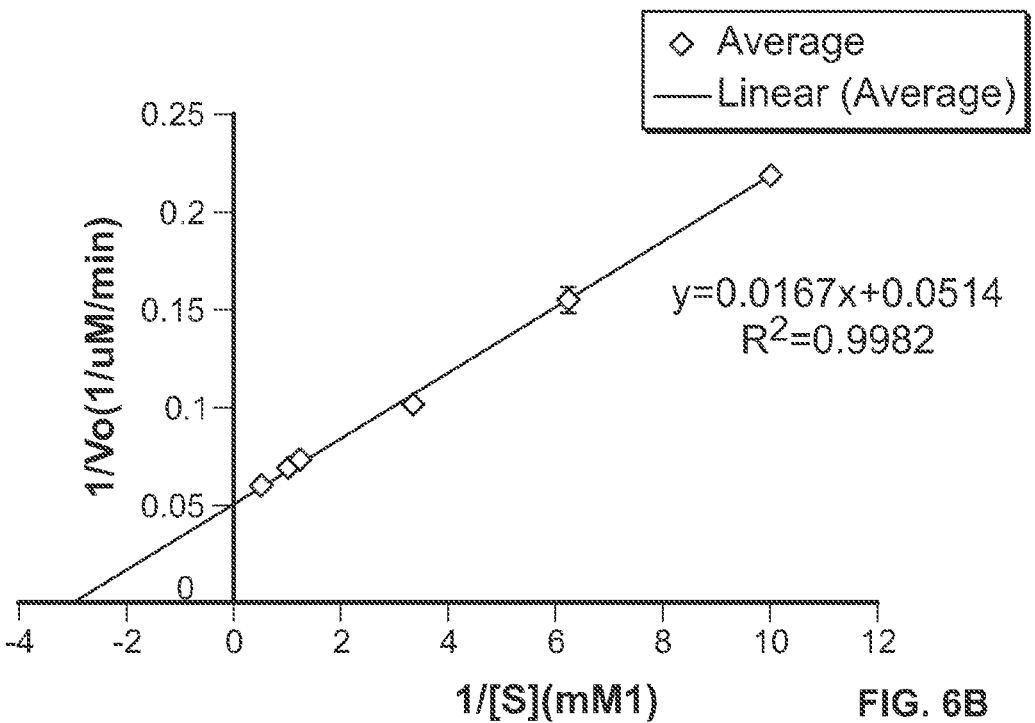
FIG. 6B is a graph depicting the $K_M$ and $K_{cat}$ determination of delta plasmin, as described in Example 1. δ-plasmin: $K_M$=324.90±8.43 μM, $K_{cat}$=778.21±1.51 l/min

As depicted in FIGS. 6A and 6B, the relative affinity of the active site for the substrate as well as the enzymatic turnover rate remains comparable between the two forms of plasmin. These results demonstrate that delta plasmin functions similarly to native plasmin even after removal of four of the five kringle domains

Example 2

In this Example, small molecule plasmin inhibitors were analyzed.

In particular, the plasmin inhibitors benzamidine, 4-aminobenzamidine, 4-carboxybenzamidine, 4-aminomethyl benzamidine, and pentamidine were analyzed (see, Table 1). The small molecule inhibitors were precisely weighed out and absorbance spectrums from 200-350 nm were taken on a SPECTRAMAX PLUS 96 well plate reader (Molecular Devices, Sunnyvale, Calif.). Absorbance maxima and extinction coefficients were calculated based on absorbance maxima and the known amount of moles of inhibitor based on weight and the known molecular weight of each inhibitor in PBS pH 7.4 at 25° C. These extinction coefficients were then used in the subsequent binding, inhibition and nanoparticle assays (Table 2).

Figure 7A:
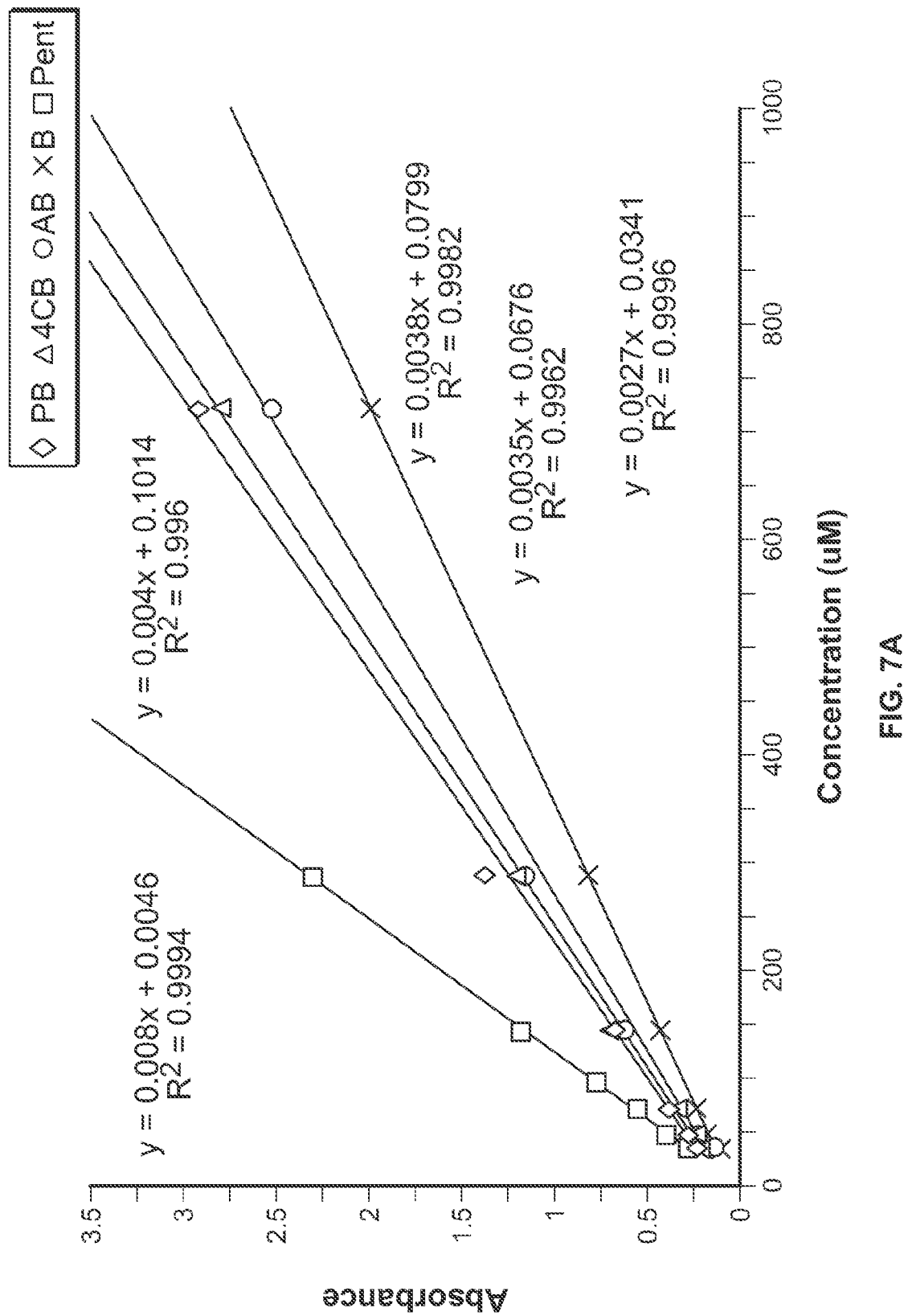
FIG. 7A is a graph depicting the determination of extinction coefficients of 4-aminobenzamidine (PB), 4-carboxybenzamidine (4CB), 4-aminomethyl benzamidine (AB), benzamidine (B) and pentamidine (Pent), as described in Example 2.
Figure 7B:
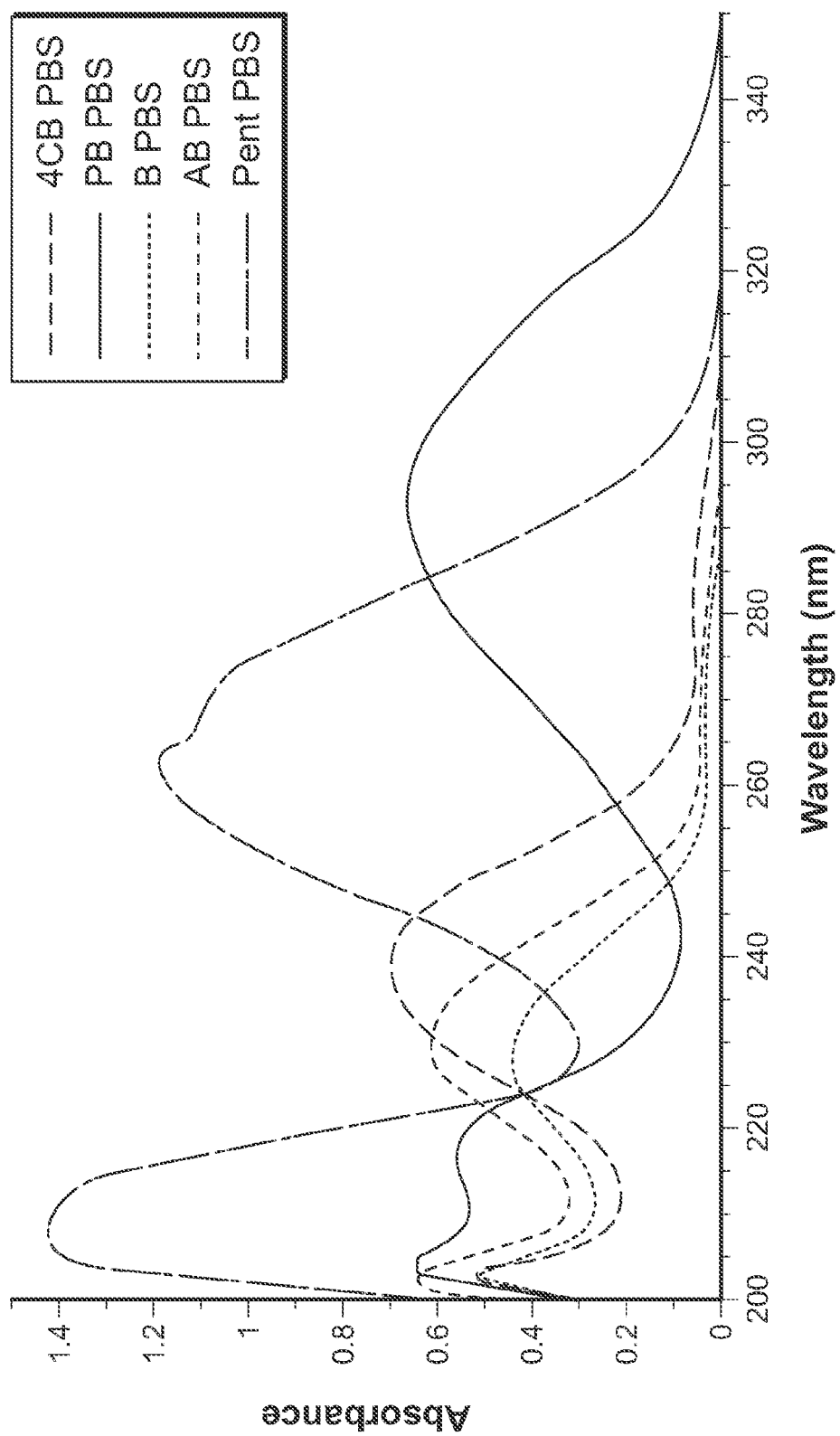
FIG. 7B is a graph depicting the extinction coefficients of 4-carboxybenzamidine (4CB PBS), 4-aminobenzamidine (PB PBS), 4-aminomethyl benzamidine (AB PBS), benzamidine (B PBS) and pentamidine (Pent PBS), as described in Example 2.
Figure 8A:
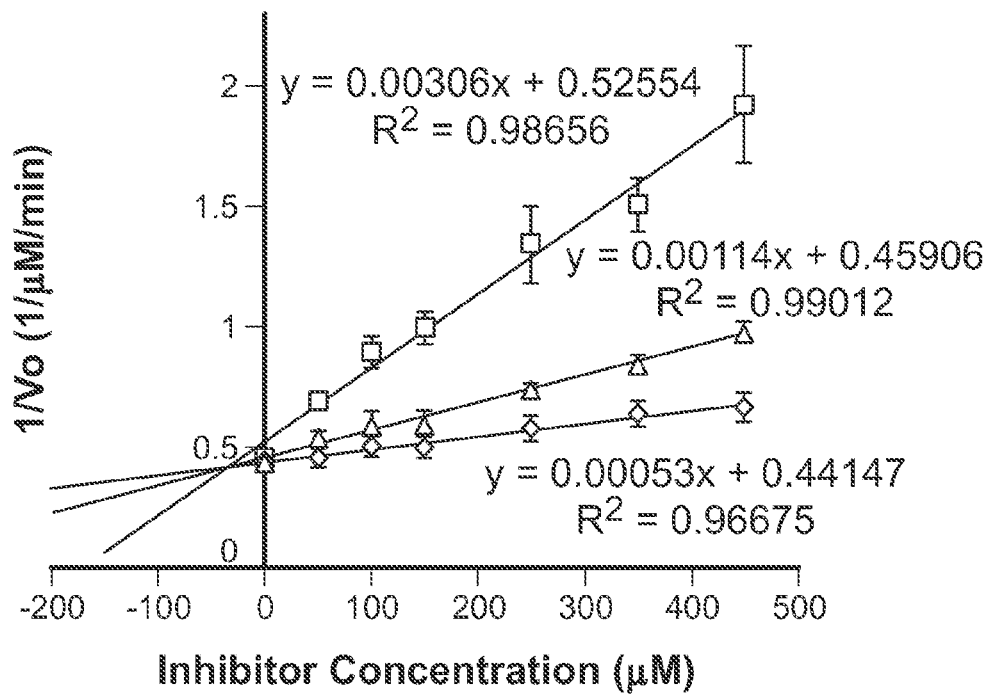
FIGS. 8A-8D are graphs depicting $K_i$ determination with benzamidine utilizing a Dixon Plot. Inhibition constant determination using S-2251 substrate. Benzamidine was incubated with plasmin (FIG. 8A) and δ-plasmin (FIG. 8B) from 0-450 μM of inhibitor at a fixed enzyme concentration of (1.0 μg/mL) with three different S-2251 concentration of 100 (squares), 350 (triangles), and 750 μM (diamonds) in PBS pH 7.4. The $K_i$ was determined by the negative intersection of the curves demonstrating uncharacteristically different inhibition constants of 32.2±3.0 and 160.8±11.7 μM for plasmin and δ-plasmin, respectively. The data were reanalyzed and plotted as $S/V_o$ vs I to graphically demonstrate that the mode of inhibition observed is purely competitive as there is no intersection of the S-2251 curves when plotted in this manner. Taking the Dixon plot and the $S/V_o$ vs I plot together the mode of inhibition observed is purely competitive in both the plasmin (FIG. 8C) and δ-plasmin (FIG. 8D) cases. All data represents means (±SD) of triplicate experiments.
Figure 8B:
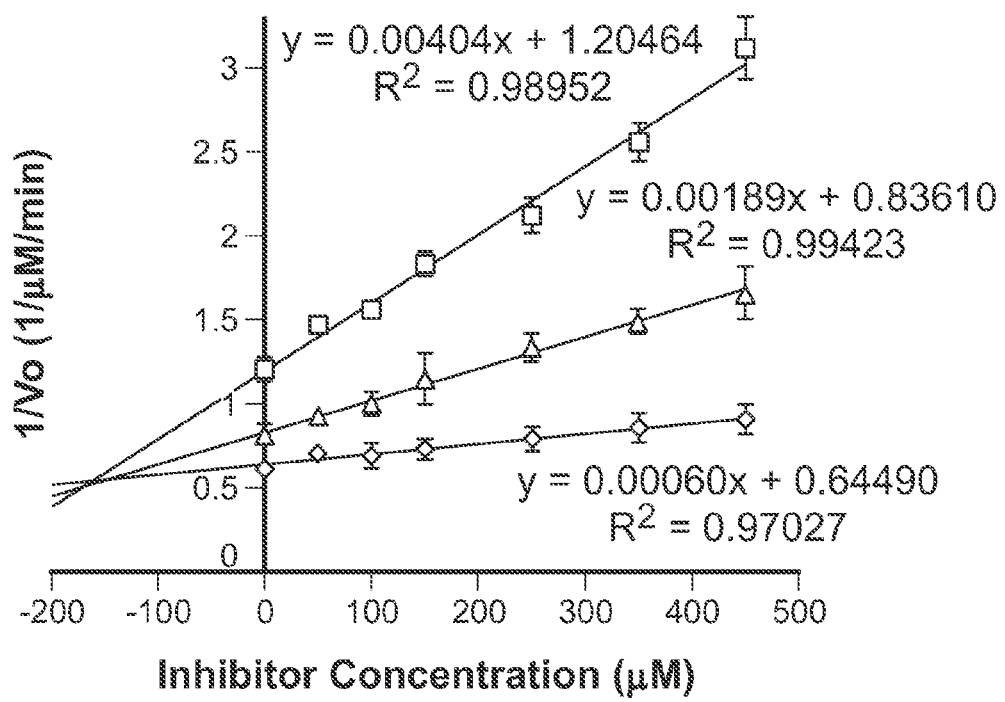
Figure 8C:
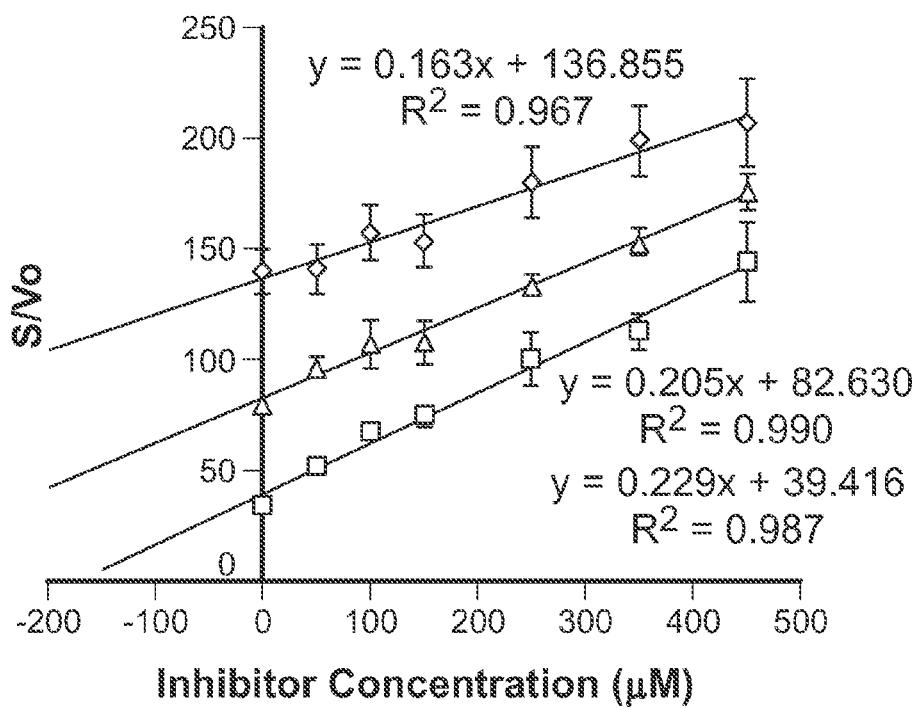
Figure 8D:
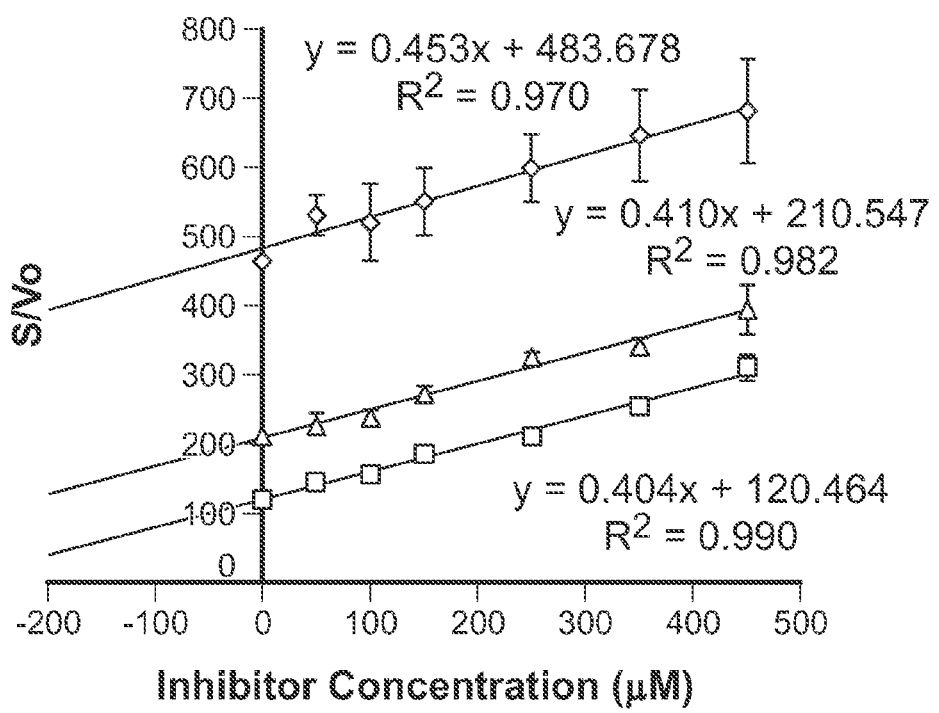

FIG. 7A depicts the extinction coefficients of benzamidine, 4-carboxybenzamidine, 4-aminobenzamidine, 4-aminomethyl benzamidine, benzamidine and pentamidine. FIG. 7B depicts the absorbance spectra of benzamidine (B), 4-carboxybenzamidine (4CB), 4-aminobenzamidine (PB), 4-aminomethyl benzamidine (AB), and pentamidine (Pent).

TABLE 2

Maximum absorbance wavelengths and calculated molar extinction coefficients for each of the inhibitor molecules in PBS pH 7.4. All data represents means (+SD) of triplicate experiments.

| Inhibitor Molecules | $ABS_{max}$ (nm) | Molar Extinction Coef. (ε) |
|---|---|---|
| Benzamidine | 228 | 10,581 + 1,113 |
| p-Aminobenzamidine | 294 | 17,010 + 1,025 |
| Carboxybenzamidine | 239 | 16,294 + 1,208 |
| Aminomethyl benzamidine | 230 | 14,247 + 943 |
| Pentamidine | 262 | 27,837 + 797 |

Each of the plasmin inhibitors were conjugated to nanoparticles and link plasmin to the nanoparticles via its active site as further demonstrated below.

Example 3

In this Example, the inhibition of plasmin and delta plasmin by benzamidine was analyzed. Inhibition assays were carried out as described above for determining the Ki of each of the benzamidine derivatives to both plasmin and delta plasmin utilizing the S-2251 substrate.

In particular, 0 μm to 750 μm of benzamidine was incubated with plasmin and delta plasmin.

FIGS. 8A-8D depict the inhibition of plasmin and delta plasmin by benzamidine. Delta-plasmin, exhibiting a higher inhibition constant than native plasmin (indicating weaker inhibition), was likely a result of some small loss of rigidity of the globular protein caused by removal of many of the kringle domains opening the active site slightly and is not a significant variation between the two derivatives. This variation was only observed in the case of benzamidine and was likely due to the smaller size of benzamidine compared to the other small molecule inhibitor molecules allowing for more degrees of freedom for binding within the active site of plasmin.

Example 4

Figure 9A:
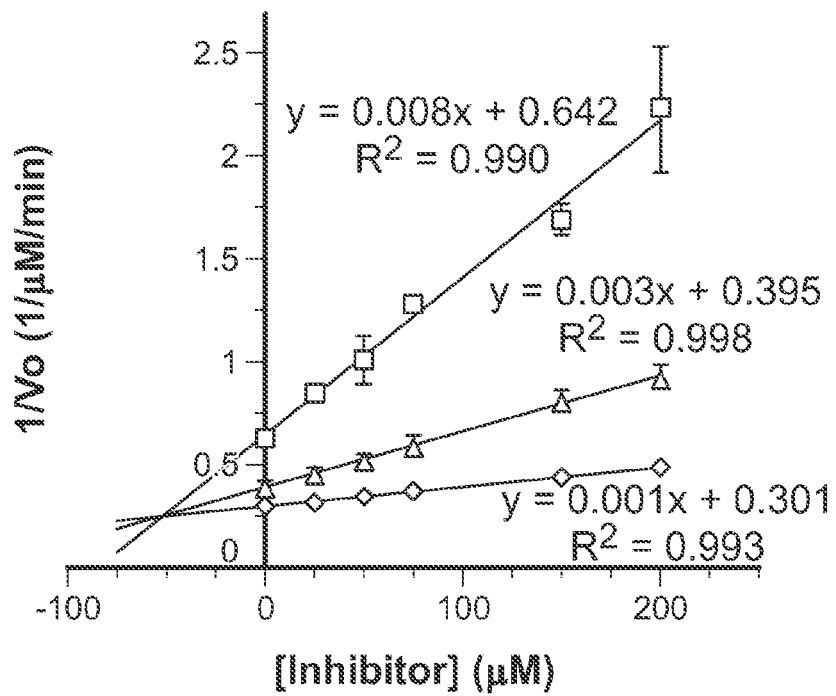
FIGS. 9A-9D depict p-Aminobenzamidine inhibition constant determination, as described in Example 4: A Dixon Plot analysis was carried out utilizing the S-2251 substrate. p-Aminobenzamidine was incubated with plasmin (FIG. 9A) and δ-plasmin (FIG. 9C) from 0-225 μM of inhibitor at a fixed enzyme concentration of 1.0 μg/mL with three different S-2251 concentration of 100 (squares), 350 (triangles), and 750 μM (diamonds) in PBS pH 7.4. The $K_i$ was determined by the negative intersection of the curves demonstrating very similar inhibition constants of 51.9±2.38 and 60.6±6.72 μM for plasmin and δ-plasmin, respectively. S/Vo vs I plots are also shown demonstrating no intersection of the S-2251 curves for plasmin (FIG. 9B) or δ-plasmin (FIG. 9D) indicative of purely competitive inhibition by p-aminobenzamidine. All data represents means (±SD) of triplicate experiments.
Figure 9B:
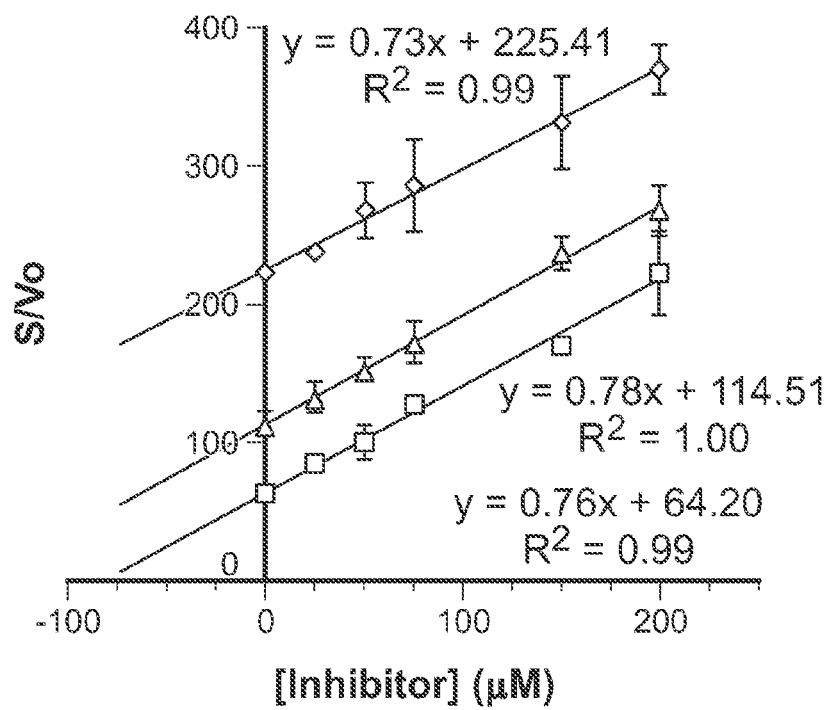
Figure 9C:
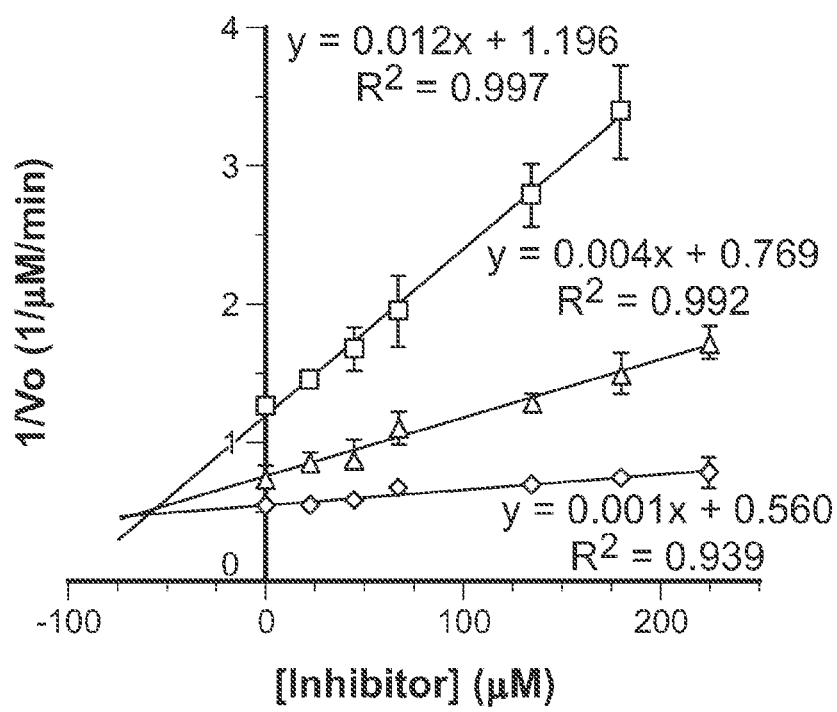

In this Example, the inhibition of sigma plasmin and delta plasmin by 4-aminobenzamidine was analyzed. Inhibition assays were carried out as described above for determining the $K_i$ of each of the benzamidine derivatives to both plasmin and delta plasmin utilizing the S-2251 substrate. In particular, 0 μm to 2250 μm of 4-aminobenzamidine was incubated with sigma plasmin and delta plasmin at S-2251 substrate concentrations of 100, 300, and 750 μM. Utilizing a Dixon Plot analysis, the $K_i$ values for both plasmin and δ-plasmin were very similar at 51.9±2.38 and 60.6±6.72 μM, respectively (FIGS. 9A and 9C). In all cases, except for the unmodified benzamidine, there was a comparable inhibition constant between both plasmin and delta plasmin derivatives.

Figure 9D:
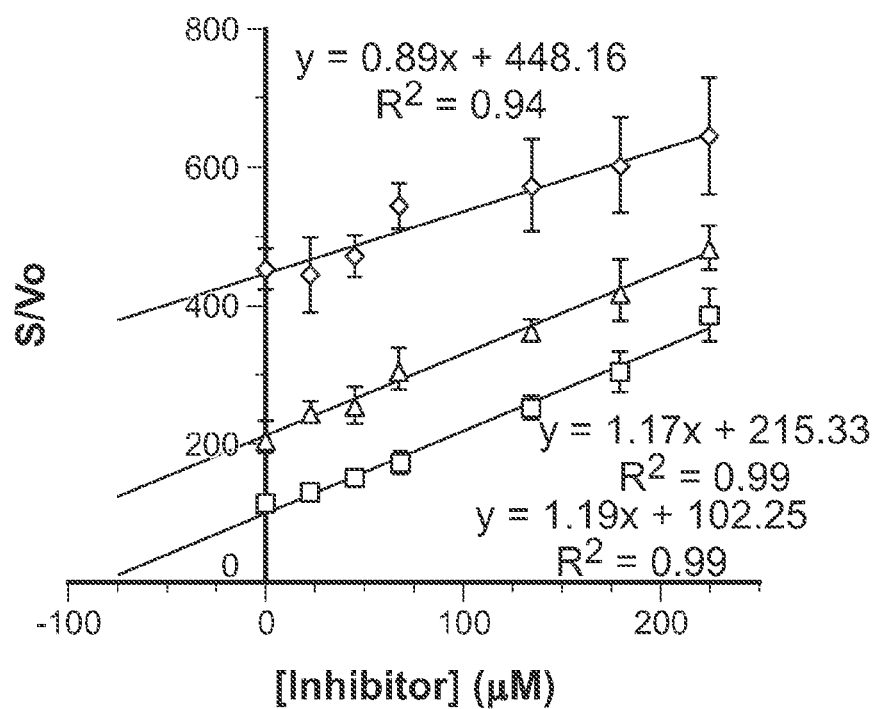

The Dixon Plot analysis on its own is not sufficient to accurately differentiate between competitive, uncompetitive, non-competitive or mixed modes of inhibition. For this reason an additional analysis of the data plotted as $S/V_o$ vs inhibitor concentration was carried out. Taken together, the intersection of the S-2251 assay curves on the Dixon Plot above the x-axis in conjunction with the lack of an intersection of the S-2251 curves on the $S/V_o$ vs I plot indicates that inhibition of both plasmin and δ-plasmin by p-aminobenzamidine is purely competitive inhibition (FIGS. 9B and 9D). The very similar $K_i$ values demonstrate the conserved nature of the active site accessibility by benzamidine congeners to both the native and truncated forms of plasmin.

Example 5

Figure 10A:
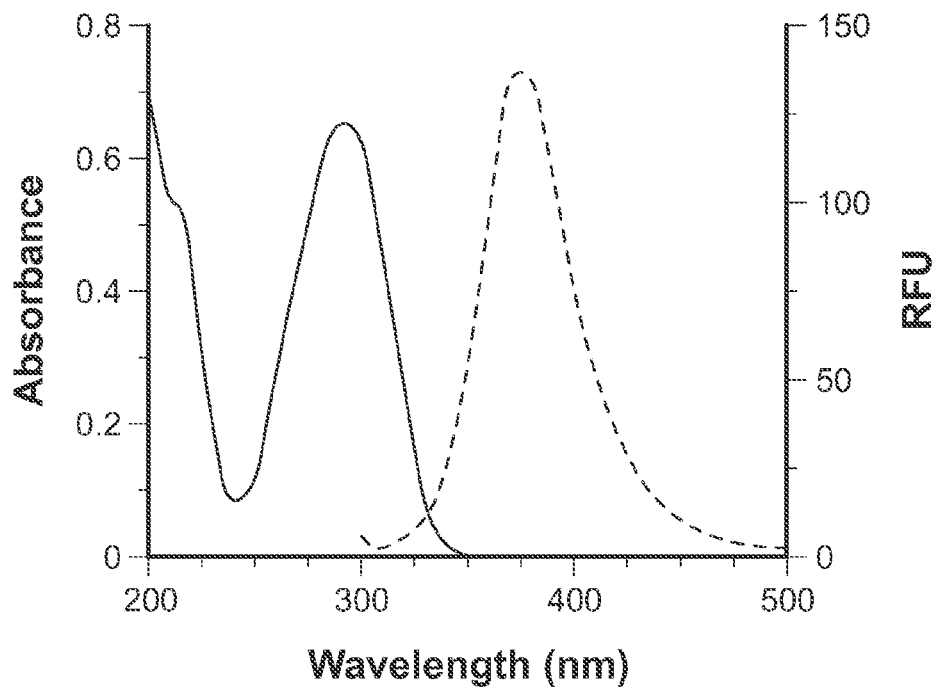
FIGS. 10A and 10B depict the binding affinity of p-aminobenzamidine to plasmin as described in Example 5. FIG.
Figure 10B:
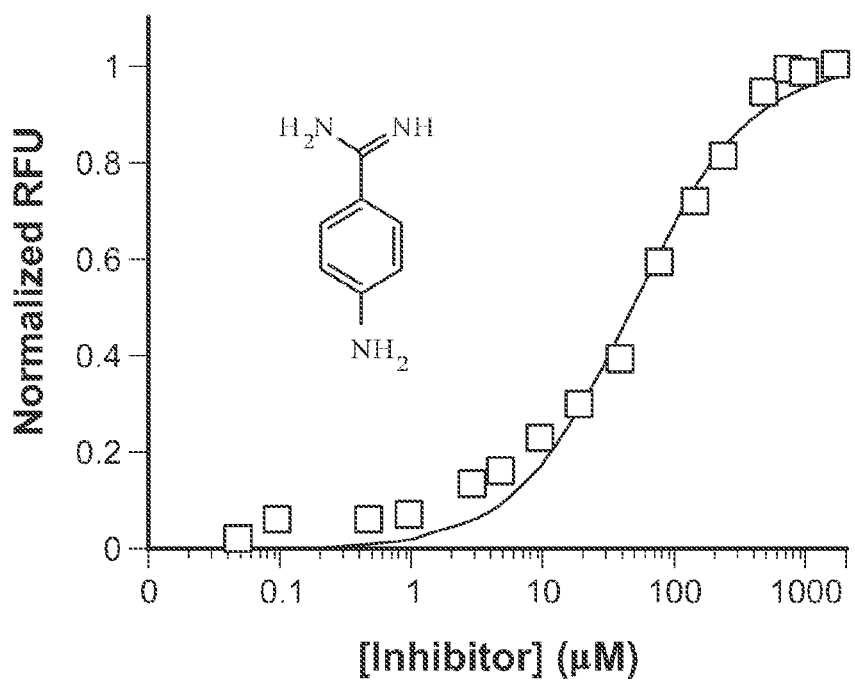
Figure 11A:
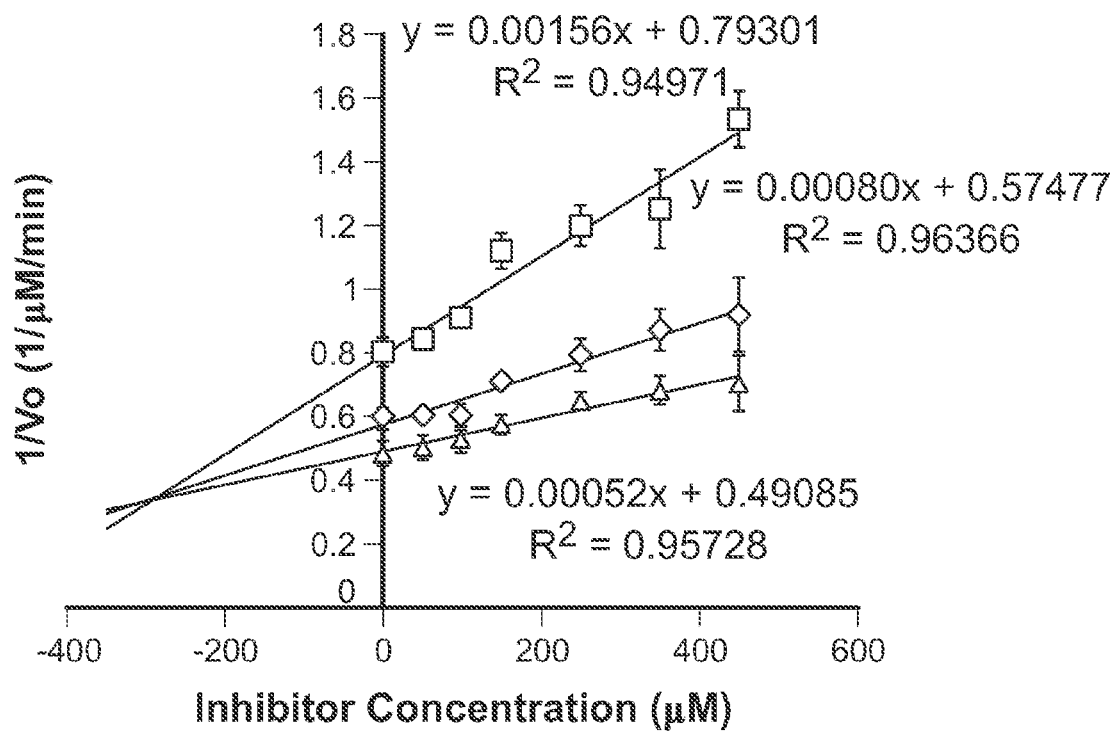
FIGS. 11A-11D are graphs depicting $K_i$ determination with carboxybenzamidine utilizing a Dixon Plot. Inhibition constant determination using S-2251 substrate. Carboxybenzamidine was incubated with plasmin (FIG. 11A) and δ-plasmin (FIG. 11B) from 0-450 μM of inhibitor at a fixed enzyme concentration of (1.0 μg/mL) with three different S-2251 concentration of 100 (squares), 350 (triangles), and 750 μM (diamonds) in PBS pH 7.4. The $K_i$ was determined by the negative intersection of the curves demonstrating very similar inhibition constants of 292.5±6.5 and 301.6±19.2 μM for plasmin and δ-plasmin, respectively. The data were reanalyzed and plotted as $S/V_o$ vs I to graphically demonstrate that the mode of inhibition observed is purely competitive as there is no intersection of the S-2251 curves when plotted in this manner Taking the Dixon plot and the $S/V_o$ vs I plot together the mode of inhibition observed is purely competitive in both the plasmin (FIG. 11C) and δ-plasmin (FIG. 11D) cases. All data represents means (±SD) of triplicate experiments.
Figure 11B:
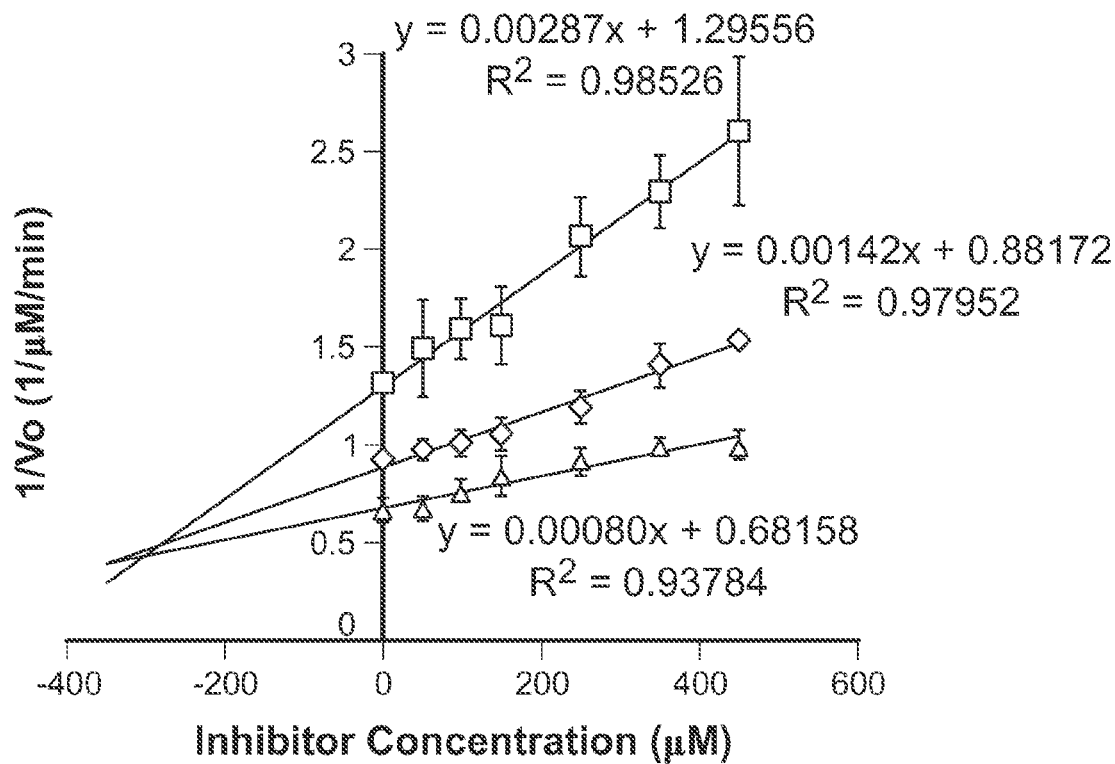
Figure 11C:
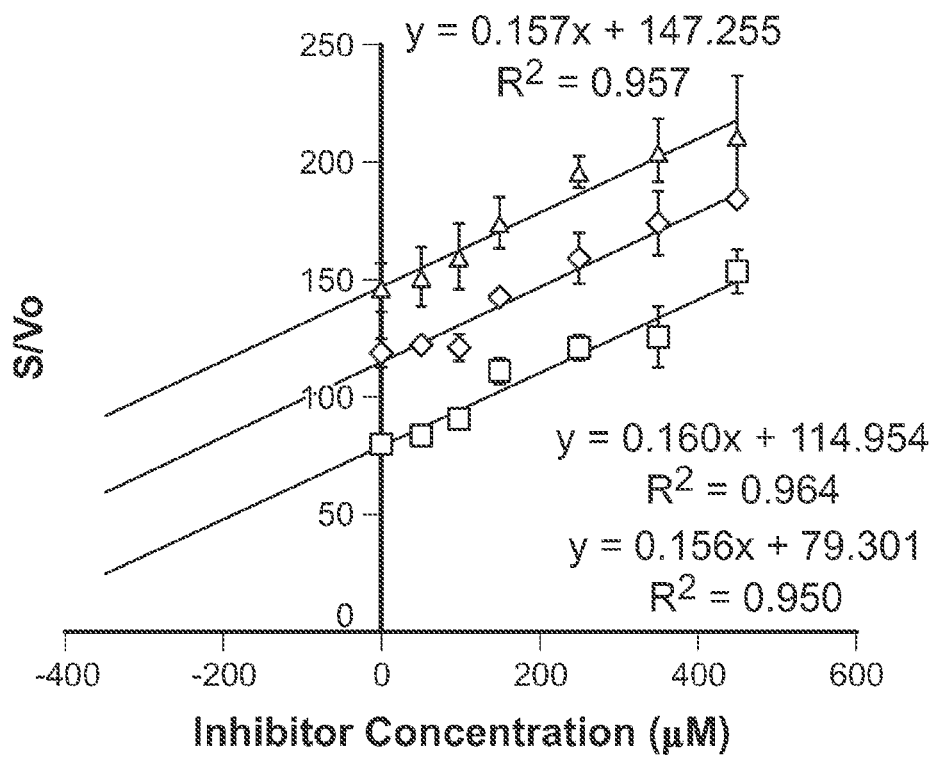
Figure 11D:
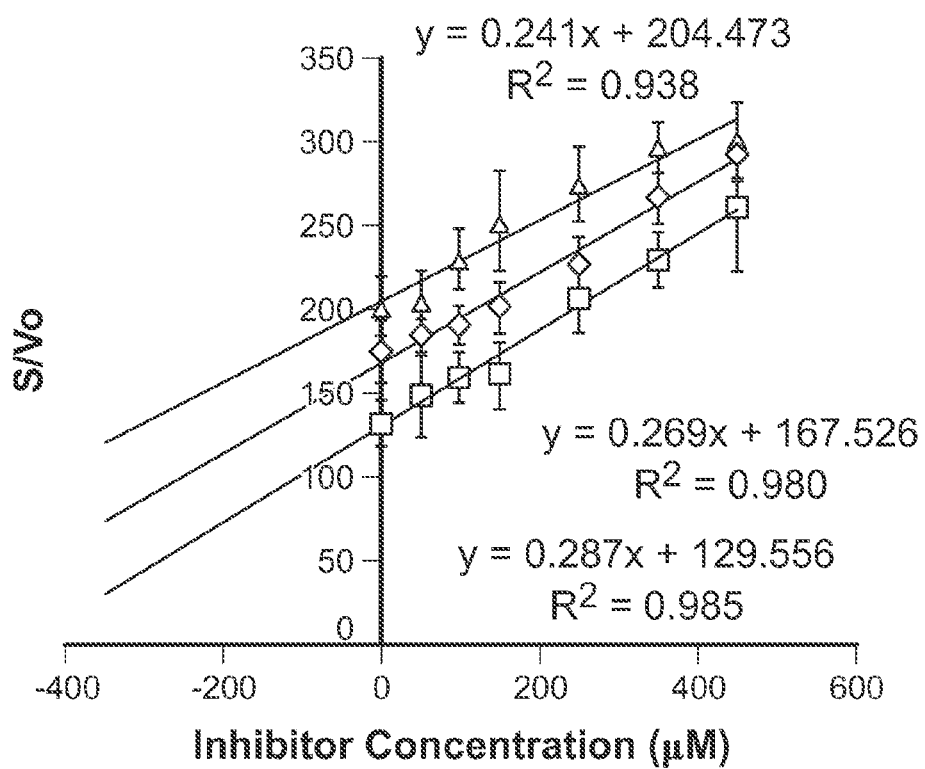
Figure 12A:
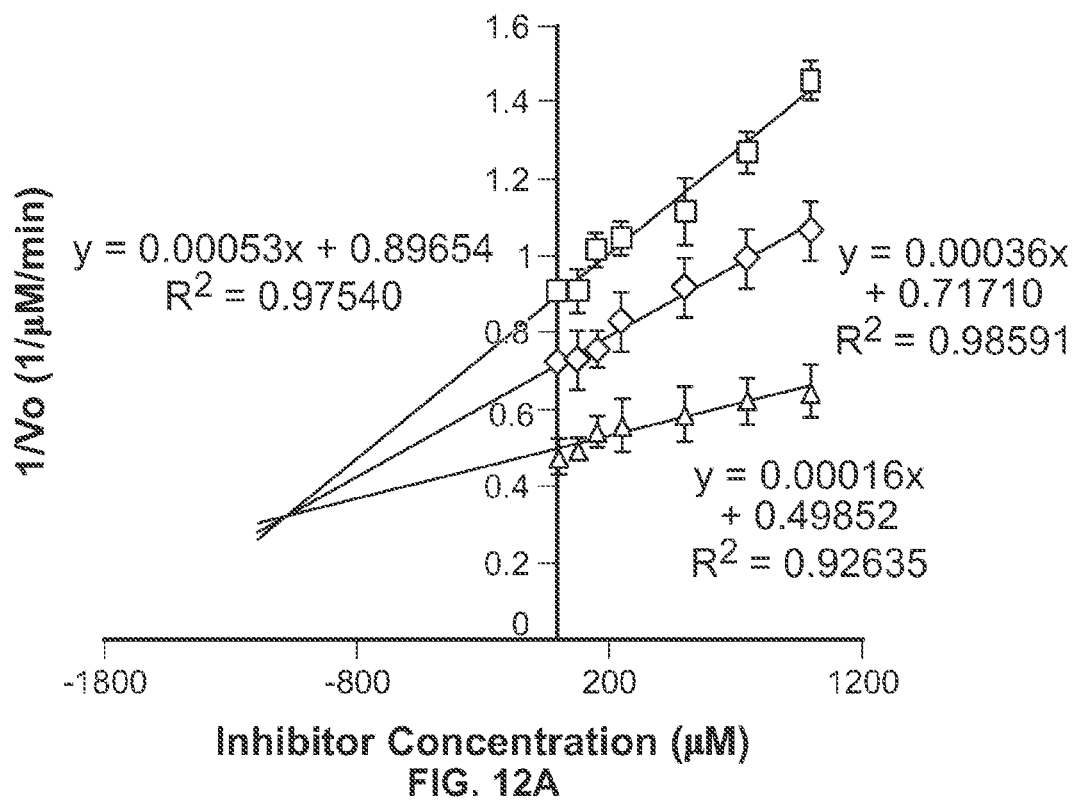
FIGS. 12A-12D are graphs depicting $K_i$ determination with aminomethyl benzamidine utilizing a Dixon Plot. Inhibition constant determination using S-2251 substrate. Aminomethyl benzamidine was incubated with plasmin (FIG. 12A) and δ-plasmin (FIG. 12B) from 0-1100 μM of inhibitor at a fixed enzyme concentration of (1.0 μg/mL) with three different S-2251 concentration of 100 (squares), 350 (triangles), and 750 μM (diamonds) in PBS pH 7.4. The $K_i$ was determined by the negative intersection of the curves demonstrating very similar, weak inhibition constants of 1074.7±18.7 and 1408.0±67.2 μM for plasmin and δ-plasmin, respectively. The data were reanalyzed and plotted as $S/V_o$ vs I to graphically demonstrate that the mode of inhibition observed is purely competitive as there is no intersection of the S-2251 curves when plotted in this manner Taking the Dixon plot and the $S/V_o$ vs I plot together the mode of inhibition observed is purely competitive in both the plasmin (FIG. 12C) and δ-plasmin (FIG. 12D) cases. All data represents means (±SD) of triplicate experiments.
Figure 12B:
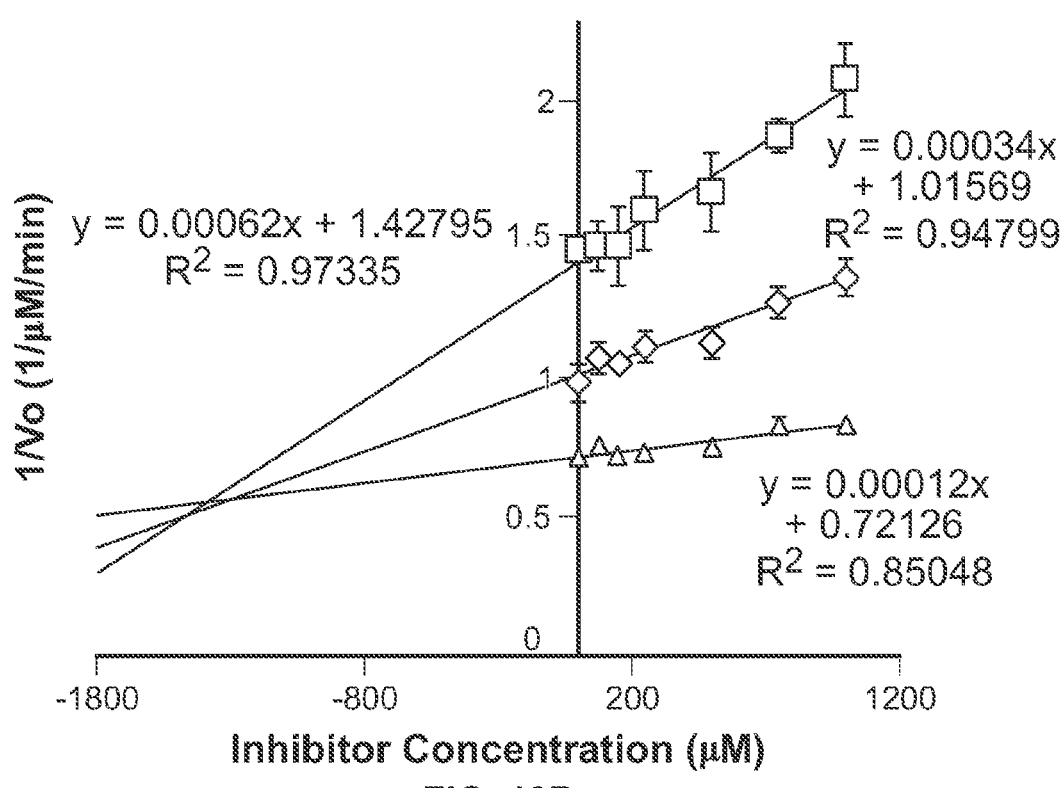
Figure 12C:
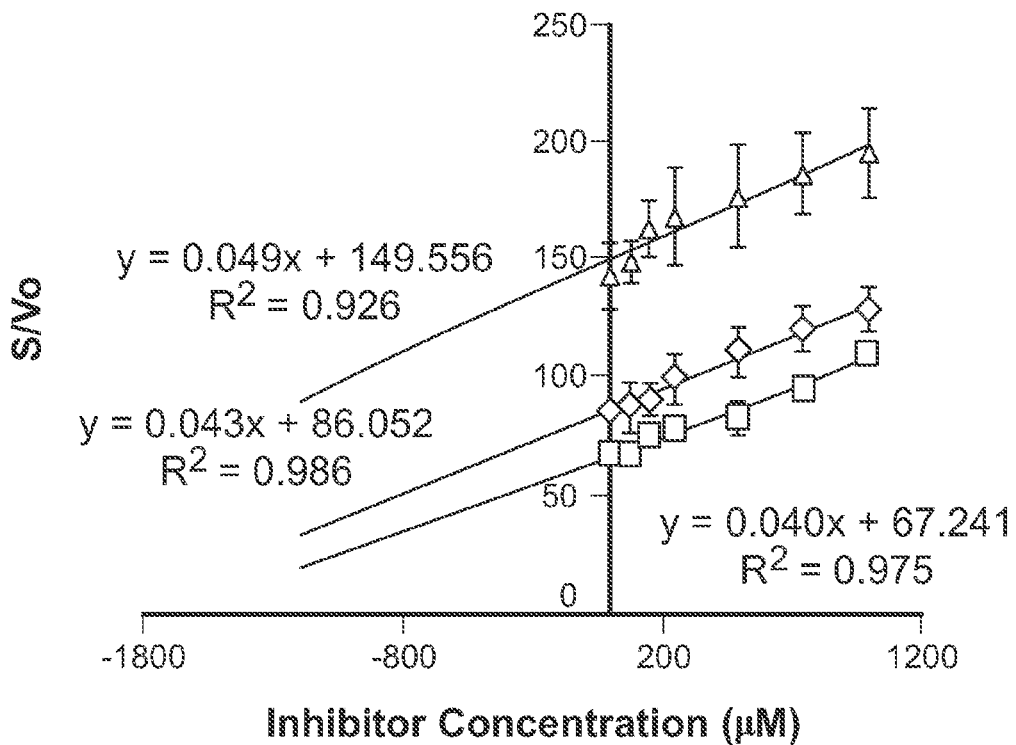
Figure 12D:
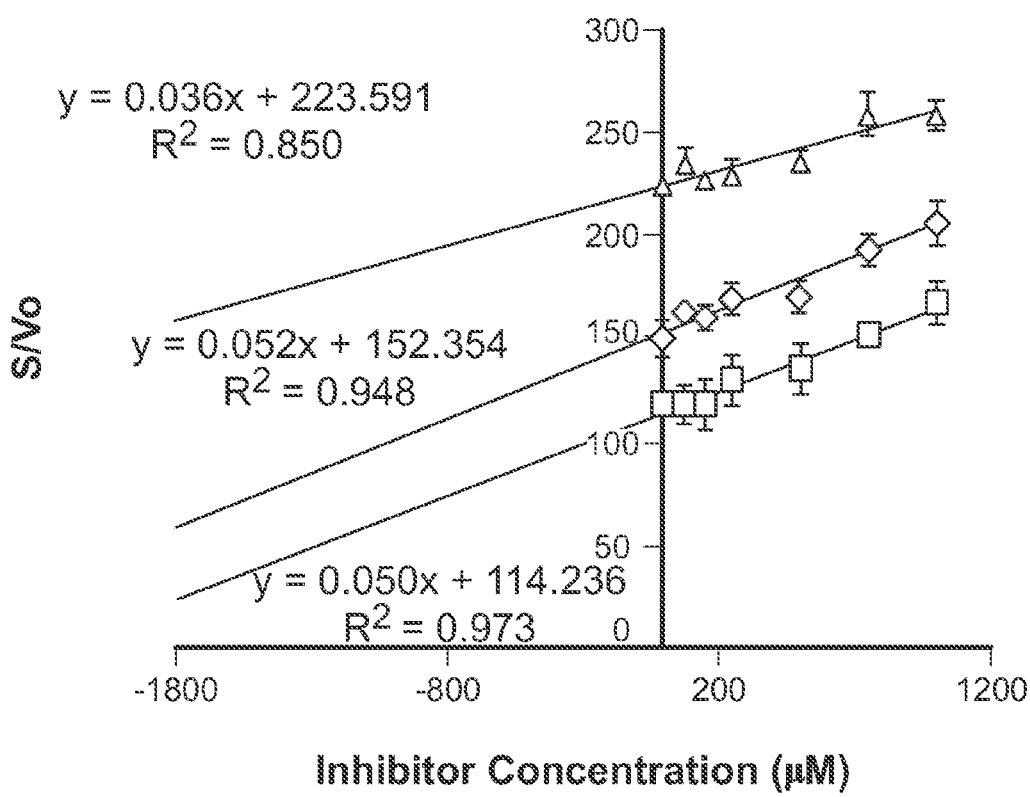
Figure 13A:
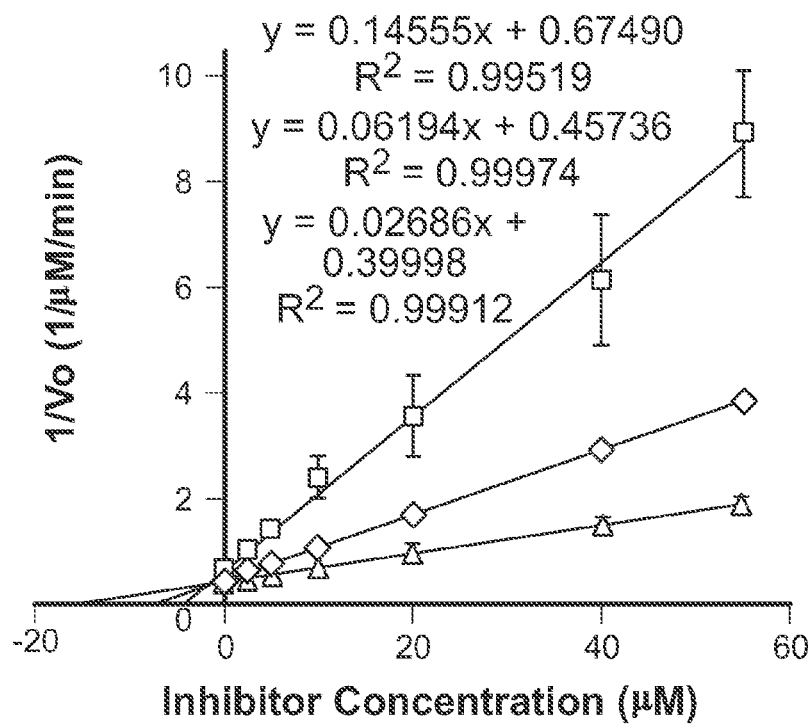
FIGS. 13A-13D are graphs depicting $K_i$ determination with pentamidine utilizing a Dixon Plot. Inhibition constant determination using S-2251 substrate. Pentamidine was incubated with plasmin (FIG. 13A) and δ-plasmin (FIG. 13B) from 0-55 μM of inhibitor at a fixed enzyme concentration of (1.0 μg/mL) with three different S-2251 concentration of 100 (squares), 350 (triangles), and 750 μM (diamonds) in PBS pH 7.4. The $K_i$ was determined by the negative intersection of the curves demonstrating very similar inhibition constants of 2.2±0.5 and 4.0±1.0 μM for plasmin and δ-plasmin, respectively. The data were reanalyzed and plotted as $S/V_o$ vs I to graphically demonstrate that the mode of inhibition observed is primarily competitive as the intersection of the S-2251 curves when plotted in this manner would intersect at a negative value >>$K_i$. Taking the Dixon plot and the $S/V_o$ vs I plot together the mode of inhibition observed is primarily competitive in both the plasmin (FIG. 13C) and δ-plasmin (FIG. 13D) cases. All data represents means (±SD) of triplicate experiments.
Figure 13B:
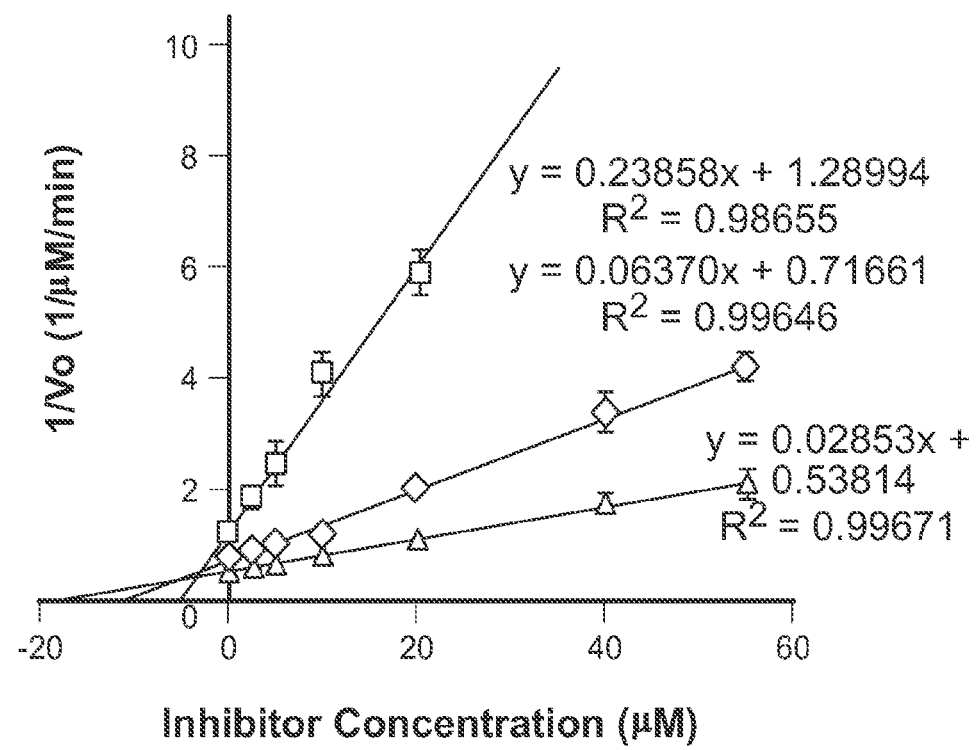
Figure 13C:
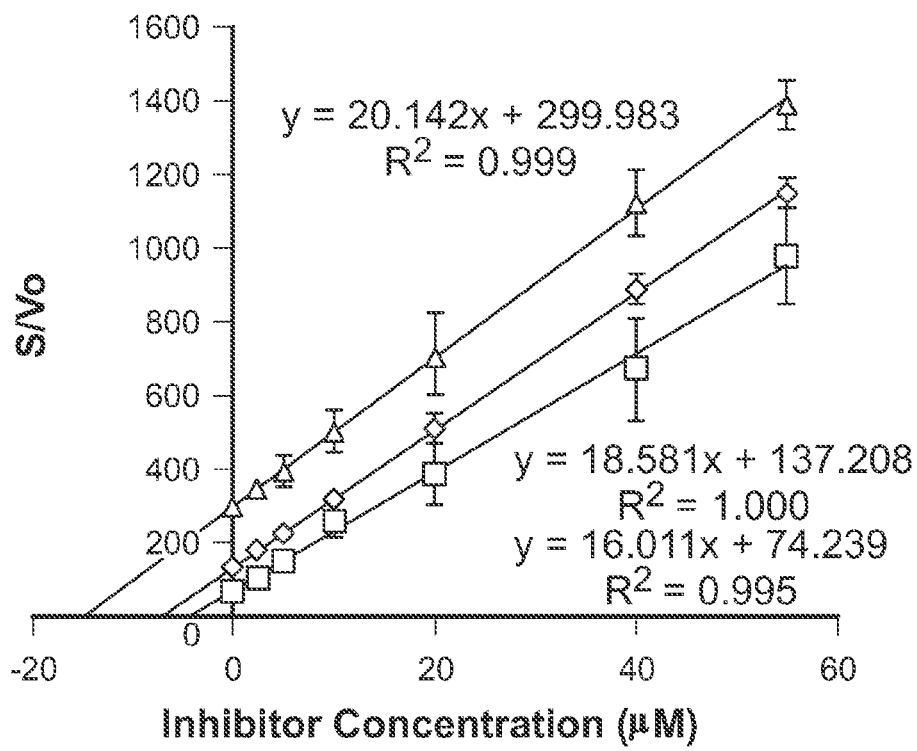
Figure 13D:
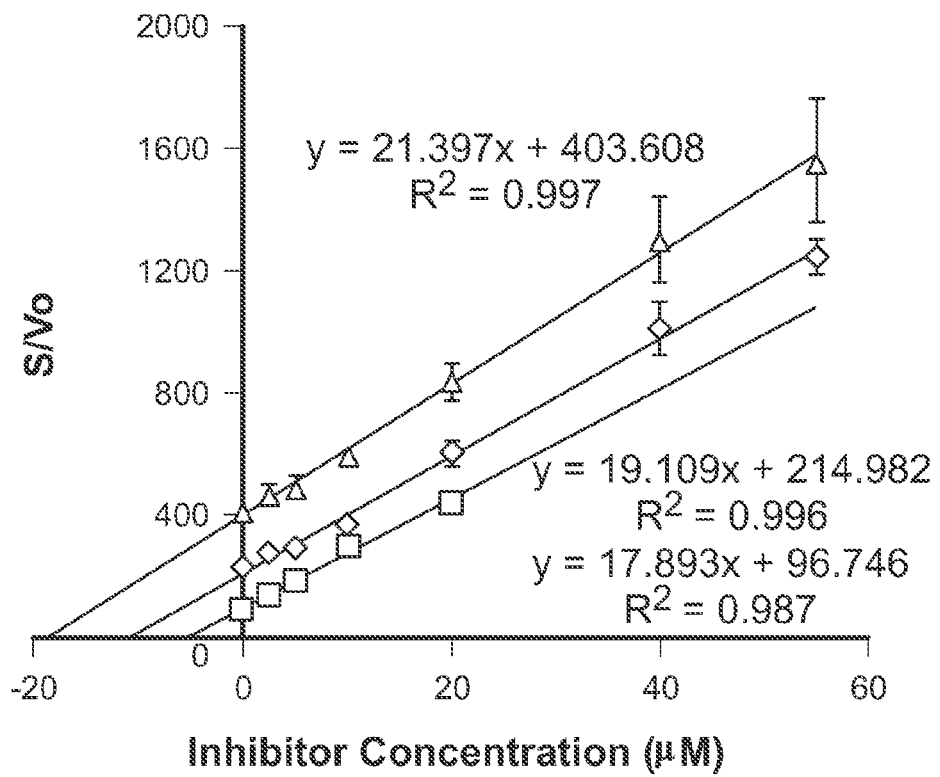

In this Example, the affinity of 4-aminobenzamidine for sigma plasmin and delta plasmin was analyzed. Fluorescent titration assay was carried out as described above for determining the $K_d$, which is the same as the Ki in the case of competitive inhibition, for the 4-aminobenzamidine derivative to plasmin in the absence of the S-2251 substrate.

p-Aminobenzamidine's fluorescent properties enable the implementation of a fluorescent titration assay to directly determine its binding affinity to plasmin Upon binding to plasmin, the p-aminobenzamidine exhibited a unique change in fluorescence that can be used to determine its dissociation constant ($K_d$). At a constant plasmin concentration, increasing amounts of p-aminobenzamidine were titrated into the sample monitoring the fluorescence emission at 370 nm (FIG. 10A). The $K_d$ of p-aminobenzamidine for plasmin, based on the fluorescent titration assay, was 53.5±4.42 μM (FIG. 10B) compared to the $K_i$ value of 51.9±2.38 μM determined via the S-2251 inhibition assay. This orthogonal method of determining affinity of p-aminobenzamidine for the plasmin's active site in the absence of the S-2251 substrate functions to validate the $K_i$ values determined via the Dixon Plot analysis as $K_i$ and $K_d$ are equal in the case of purely competitive enzymatic inhibition. None of the other benzamidine-based inhibitors as discussed below exhibited this characteristic and were therefore not amenable to a similar fluorescent titration assay.

Example 6

In this Example, the inhibition of plasmin and delta plasmin by 4-carboxybenzamidine was analyzed.

Inhibition assays were carried out as described above for determining the Ki of each of the 4-carboxybenzamidine derivatives to both plasmin and delta plasmin utilizing the S-2251 substrate.

FIGS. 11A-11D depict the inhibition of plasmin and delta plasmin by 4-carboxybenzamidine. In all cases, except for the unmodified benzamidine, there is a comparable inhibition constant between both plasmin and delta plasmin derivatives.

Example 7

In this Example, the inhibition of plasmin and delta plasmin by 4-aminomethyl benzamidine was analyzed.

Inhibition assays were carried out as described above for determining the Ki of each of the 4-aminomethyl benzamidine derivatives to both plasmin and delta plasmin utilizing the S-2251 substrate.

FIGS. 12A-12D depict the inhibition of plasmin and delta plasmin by 4-aminomethyl benzamidine. This molecule demonstrated the weakest inhibition constant for plasmin and delta plasmin with Ki values >1000 μM.

Example 8

In this Example, the inhibition of sigma plasmin and delta plasmin by pentamidine was analyzed.

Inhibition assays were carried out as described above for determining the Ki of each of the pentamidine derivatives to both plasmin and delta plasmin utilizing the S-2251 substrate.

FIGS. 13A-13D depict the inhibition of plasmin and delta plasmin by pentamidine. The pentamidine small molecule exhibited the strongest inhibition of plasmin and delta plasmin with Ki values <4 µM. These Ki values represent a >15-fold stronger inhibition than the next best inhibitor for both plasmin and delta plasmin. The 13-fold discrepancy demonstrates that inhibition is more than simply the arithmetic sum of the number of benzamidine moieties on the molecule and rather there is also a strong avidity effect present resulting in a much stronger inhibition of plasmin due to the multivalent presentation of benzamidine. The close proximity of the two benzamidine moieties allows for an increased probability of plasmin rebinding resulting in an apparent increase in the strength of inhibition. This avidity phenomena can be exploited to improve inhibition constants for other inhibitors by simply increasing their valency and may provide a means of tuning inhibition for the therapeutic delivery of delta plasmin Table 3 summarizes the data obtained in Examples 3-7.

TABLE 3

Ki and Enzyme Summary.

|  | Plasmin | StDev | Pen X-Fold inhibition | Delta Plasmin | StDev | Pen X-Fold inhibition |
|---|---|---|---|---|---|---|
| Km | 268.8 | 19.1 |  | 324.9 | 8.4 |  |
| Vmax | 9.2 | 0.5 |  | 19.5 | 0.0 |  |
| [Protein] | 12.0 | nM |  | 25.0 | nM |  |
| Kcat | 770.5 | 41.7 |  | 778.2 | 1.5 |  |
| B Ki | 32.2 | 3.0 | 14.8 | 160.8 | 11.7 | 40.4 |
| PB Ki | 51.9 | 2.4 | 23.8 | 60.6 | 6.7 | 15.2 |
| 4CB Ki | 292.5 | 6.5 | 134.2 | 301.6 | 19.2 | 75.8 |
| AB Ki | 1074.7 | 18.7 | 493.0 | 1408.0 | 67.2 | 353.8 |
| Pentamidine Ki | 2.2 | 0.5 |  | 4.0 | 1.0 |  |
| PB Fl Ki | 53.5 | 4.4 |  |  |  |  |

Example 9

In this Example, micelle and liposome nanoparticles were prepared.

Figure 14A:
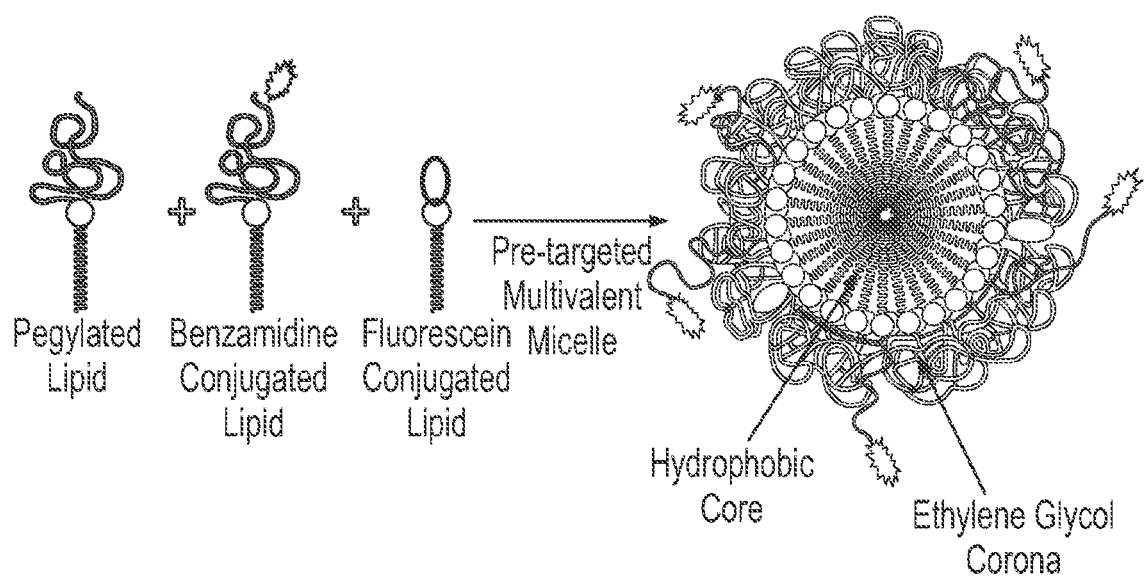
FIG. 14A is a schematic illustrating the components and preparation of an example micelle embodiment of the nanoparticle of the present disclosure, as described in Example 9.
Figure 15A:
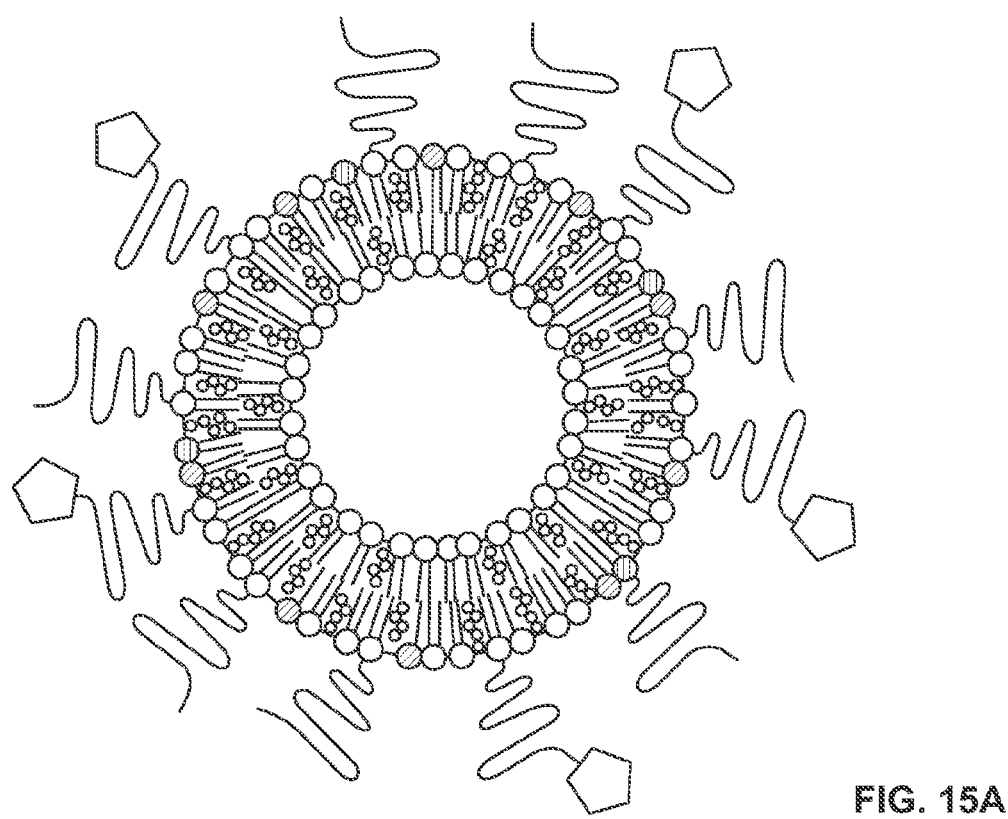
FIG. 15A is a schematic illustrating the components and preparation of an example liposome embodiment of the nanoparticle of the present disclosure, as described in Example 9.

Specifically, micelle nanoparticles were prepared by conjugating 4-carboxybenzamdine to DSPE-PEG2000-amine using EDC coupling in MES buffer (see, FIGS. 14A and 15A). DSPE-PEG2000-amine in chloroform was obtained from Avanti Polar Lipids (Alabaster, Ala.). A lipid film of DSPE-PEG2000-amine was prepared by pipetting 10 mg of DSPE-PEG2000-amine into a scintillation vial and evaporating the chloroform under gentle flowing dry nitrogen while rotating the vial. The dried lipid film was then placed in a desiccator under vacuum for at least 2 hours to further remove any residual organic solvent. After at least 2 hours, the lipid film was rehydrated by adding 1 mL of water to the film and agitated until all lipid was removed from the vial wall and a milky solution was produced. The milky solution was then left without disruption to allow the formation of micelles by self-assembly. Optionally, more rapid micelle formation with a less polydisperse final product was induced using tip sonication (Model 550 Sonic Dismembrator commercially available from Fisher Scientific). For tip sonication, the tip of the instrument was submerged just below the surface of the lipid solution and sonicated under continuous sonication mode supplying 10-15% power for 3 minutes, followed by a 3 minute pause, and followed by a second 3 minute sonication using care to avoid excessive heating of the solution or formation of bubbles in the solution. The solution clarified as micelles formed. The process could be repeated if necessary to ensure all lipids were incorporated into micelles. Dynamic light scattering (DLS) was performed to verify micelle formation to allow for accurate measurement of the nanoparticle diameter in solution. A pre-conjugation adsorption spectrum of the sample (200-350 nm) was taken to document a baseline absorbance and to allow for accurate quantification of conjugation yield. Careful documentation of the lipid concentration, the dilution factor, and the total volume of the sample was taken for later quantification of the coupling efficiency of 4-carboxybenzamidine to the micelle nanoparticles.

To solubilize 4-carboxybenzamidine in preparation for the conjugation reaction, 20 mg of 4-carboxybenzamidine was added to 1 mL of MES buffer (0.1 mM MES, 0.5 mM NaCl, pH 6.0) and was slightly heated at 50° C. for 2-5 minutes and bath sonicated for 1-2 minutes to improve solubility. The 4-carboxybenzamidine was then added drop-wise to the micelle solution. EDC was solubilized by adding 100 mg to 500 µL of water and added drop-wise to the micelle/4-carboxybenzamidine mixture while mixing. The reaction mixture was protected from light and mixed on a rocker table for 4-12 hours.

The 4-carboxybenzamidine conjugated micelles were then purified via dialysis using 10-12 kDa cutoff dialysis membrane in water with at least 4 cycles of buffer exchange. Following dialysis, the volume of the micelle solution was obtained and another adsorption spectrum was conducted. Using the molar extinction coefficient of 16,294 for 4-carboxybenzamidine (239 nm), the pre-conjugated micelle spectrum was subtracted from the post-conjugation spectrum, and the concentration of 4-carboxybenzamidine, as well as the coupling efficiency, was determined. An optional reaction step was used to cap any remaining amine groups on the micelle nanoparticle by following the procedure to couple the 4-carboxybenzamidine to lipid but substituting the 4-carboxybenzamidine with a COOH—C—C—OH ligand. Micelle nanoparticles conjugated with 4-carboxybenzamidine and dialyzed against water were dried by lyophilization and stored at −20° C. or −80° C. until use. To rehydrate and resolubilize the lyophilized micelle nanoparticles conjugated with 4-carboxybenzamidine, the protocol described above through the tip sonication step was followed.

Dried conjugated lipids were also mixed in chloroform at specific mole ratios with other bulk lipid components such as HSPC or DPPC and cholesterol until a homogenous mixture was obtained and lipids were again dried to form a lipid film and were used in liposome formation. To prepare liposome nanoparticles, lipid components (DPPC or HSPC) and cholesterol were added to a scintillation vial to contain typically 90% bulk lipid, 10% conjugated lipid of DSPE-PEG(2000) lipid and a 1:10 ratio of cholesterol to total lipid. Nitrogen gas was flowed over the solution while rotating the vial until all of the solvent was evaporated. The vial was then placed in a vacuum desiccator or lyophilized for at least 2 hours to remove any residual solvent. After at least 2 hours, the lipid film was rehydrated by adding 1 mL of water to the film and agitated at 5-10° C. over the lipid glass transition temperature (Tg; 43° C. for DPPC and 55° C. for HSPC) for 1 hour, or until all lipid was removed from the vial wall and a milky solution was produced. To form liposomes, extrusion was performed using a 1 mL blunt-tip syringe and an extrusion apparatus (commercially available from Avanti Polar Lipid). Alternatively, liposome formation was performed using freeze/thaw cycles or sonication. For extrusion, the lipid solution was drawn into the syringe with care taken to avoid formation of air bubbles. An empty syringe was then placed into the opposite side of the extrusion holder and the syringes were then locked into the base heating block which was also maintained at a temperature about 5-10° C. above the lipid Tg. The lipid solution was then extruded using 15 passes through a pre-wet polycarbonate track etched membrane designed to produce 100 nm diameter liposomes. The pore size of the membranes directly correlates with the diameter of the extruded liposomes. Following extrusion, water or buffer was added to the extruded liposomes to increase the final volume. DLS was performed on the sample to ensure proper liposome size. Resultant liposomes have ~50% of the functionalized 4-carboxybenzamidine lipid facing the aqueous interior, which is factored in when determining the lipid mole ratios for any experimental purposes. Additionally, for liposome formation, the PEG2000 content cannot exceed 10% of the total lipid concentration to maintain a stable liposome product.

Figure 14B:
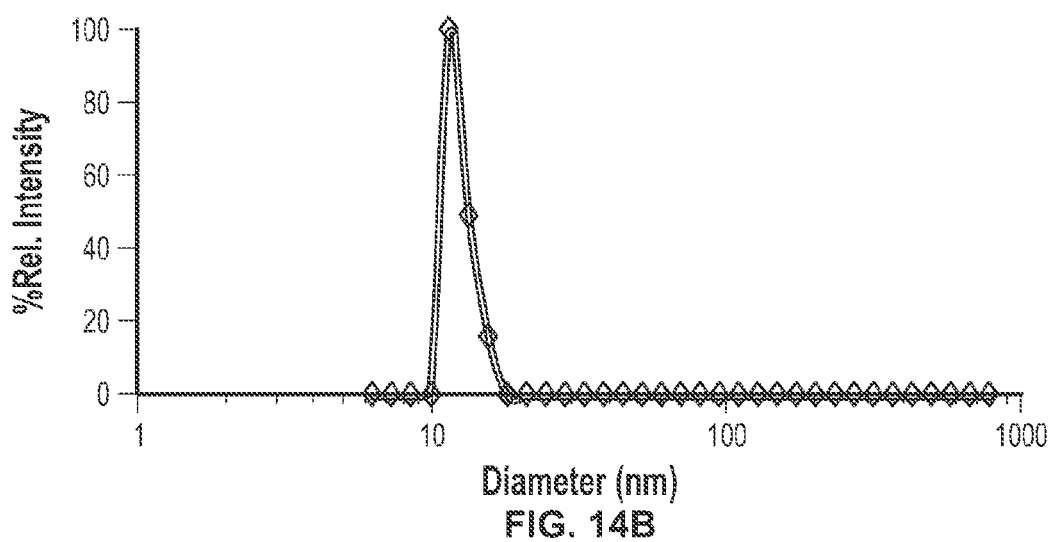
FIG. 14B is a graph depicting the hydrodynamic diameters of micelle embodiments of the nanoparticle of the present application, as described in Example 8.
Figure 15B:
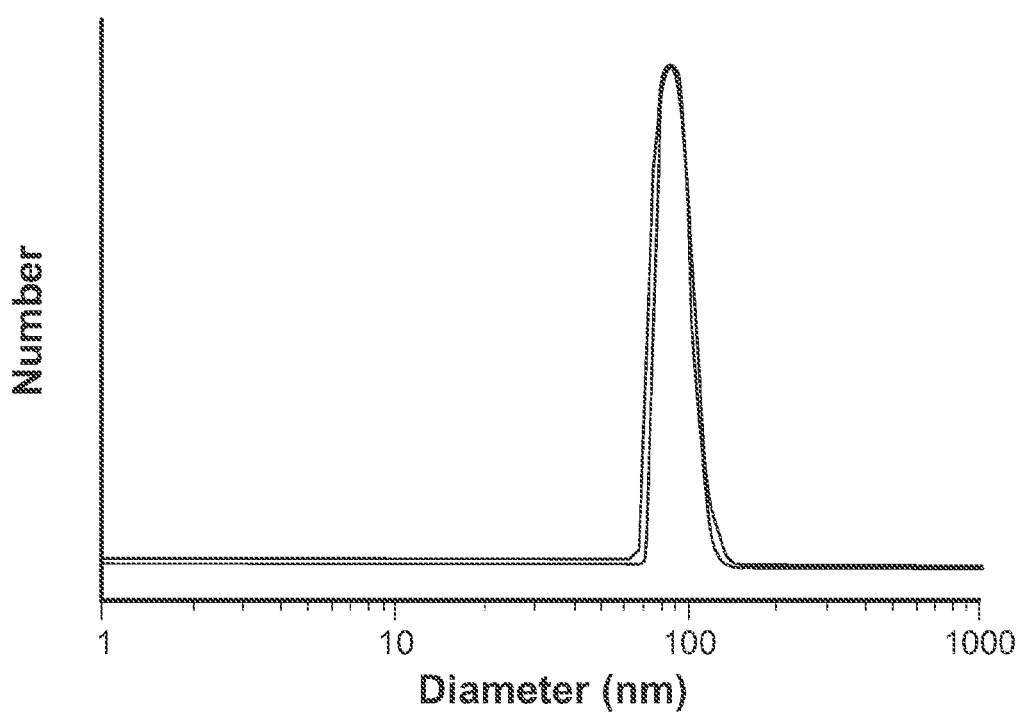
FIG. 15B is a graph depicting the hydrodynamic diameters of liposome embodiments of the nanoparticle of the instant application, as described in Example 9.

FIG. 14B depicts the diameters of micelle nanoparticles made according to the sonication protocol described above. FIG. 15B depicts the diameters of liposome nanoparticles extruded using a 100 nm diameter specific polycarbonate track etched membrane as described above. The chemical structures of the components used for conjugating benzamine derivatives to lipid molecules include:

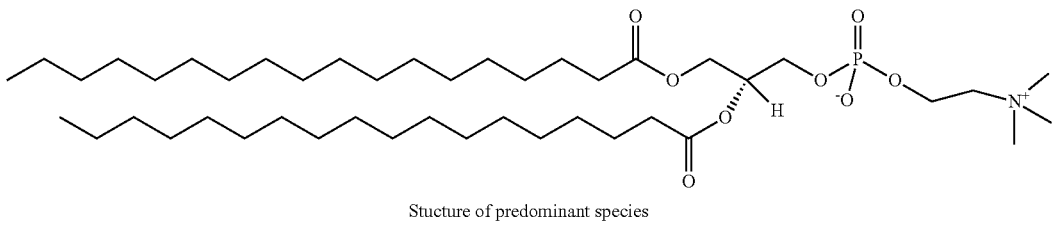

Stucture of predominant species
HSPC (Tg = 55 C.) a quaternary ammonium cation

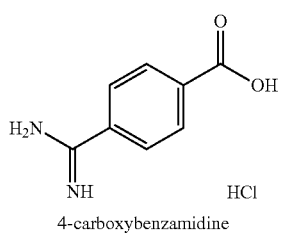

4-carboxybenzamidine

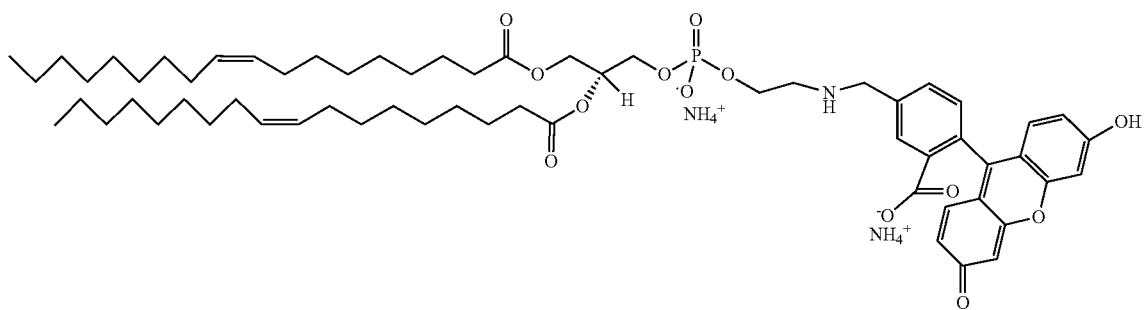

PE-CF

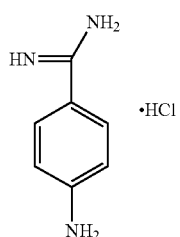

4-Aminobenzamidine

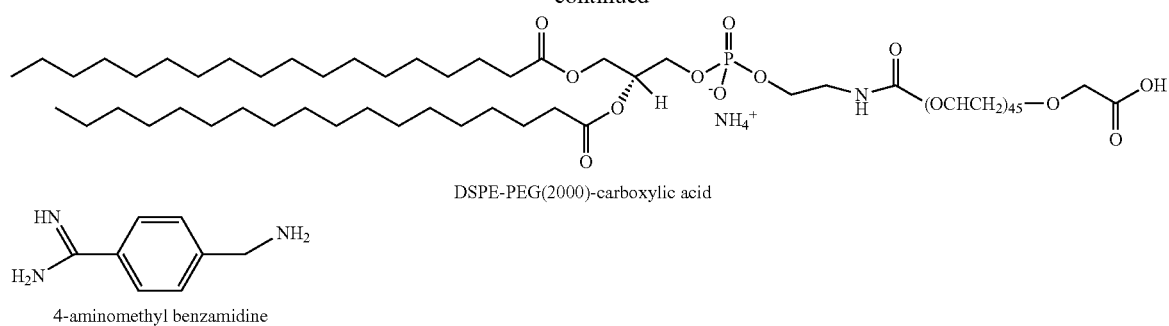

DSPE-PEG(2000)-carboxylic acid

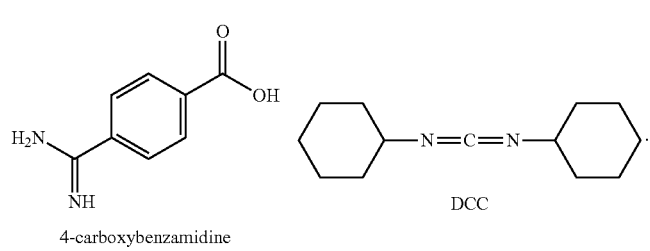

4-aminomethyl benzamidine

The steps for conjugating 4-carboxybenzamidine to DSPE-PEG(2000)-amine with DCC instead of EDC used as a cross-linking reagent are as follows:

1

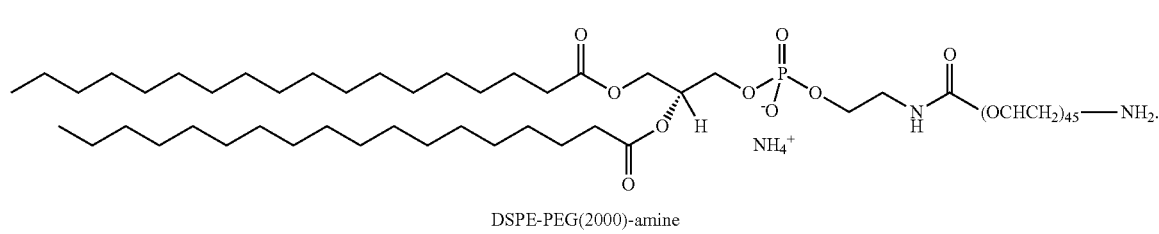

4-carboxybenzamidine     DCC

2

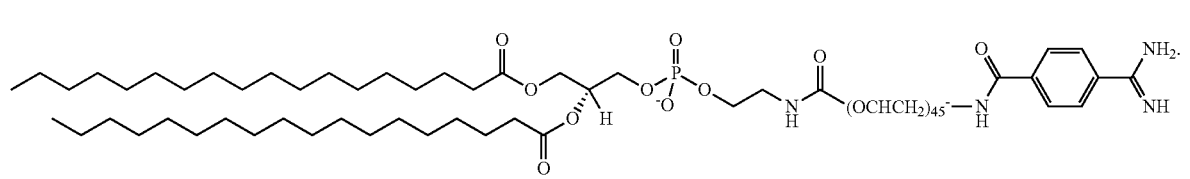

DSPE-PEG(2000)-amine

3

Figure 16A:
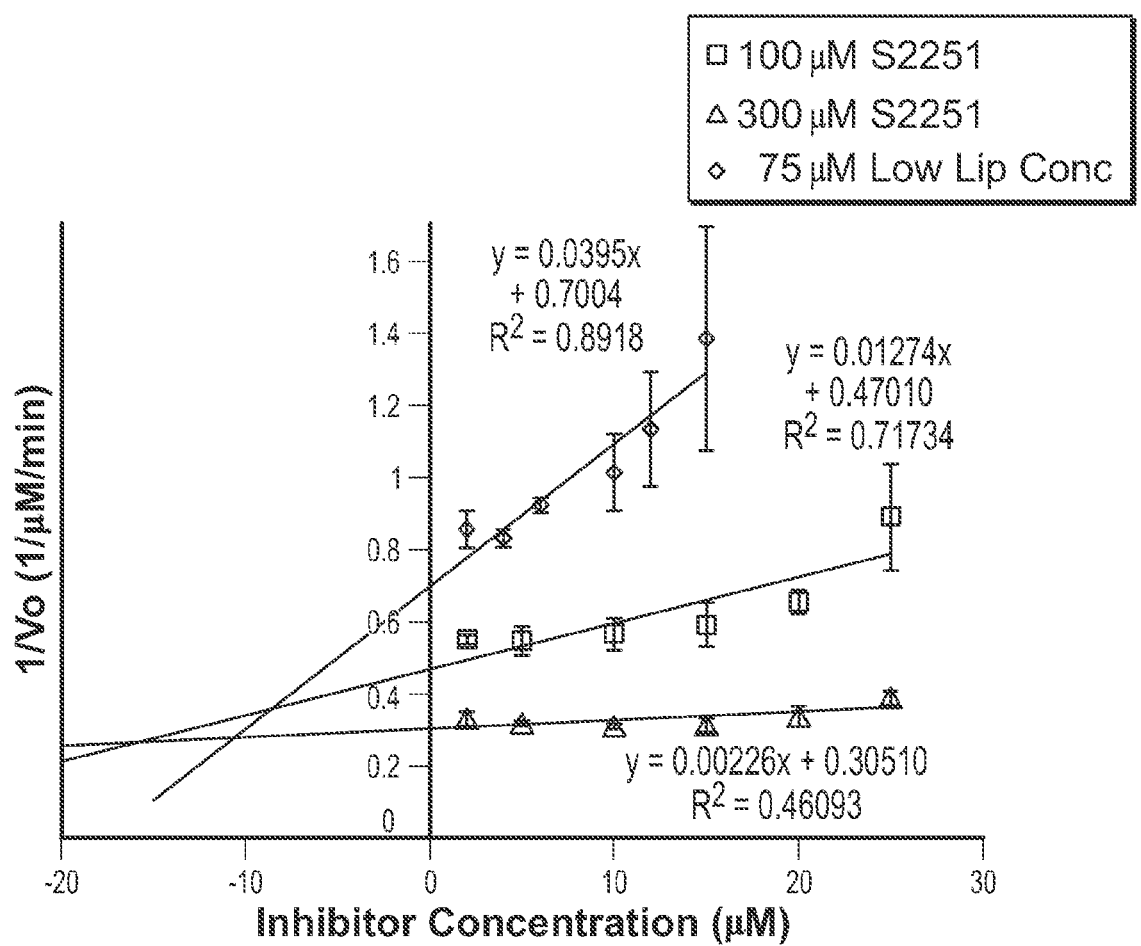
FIG. 16A is a graph depicting the multivalent effect of 4-carboxybenzamidine conjugated to liposome nanoparticles and the resultant reduction in inhibitory constant caused by the multivalent effect compared to free (unconjugated) 4-carboxybenzamidine, as described in Example 9.
Figure 16B:
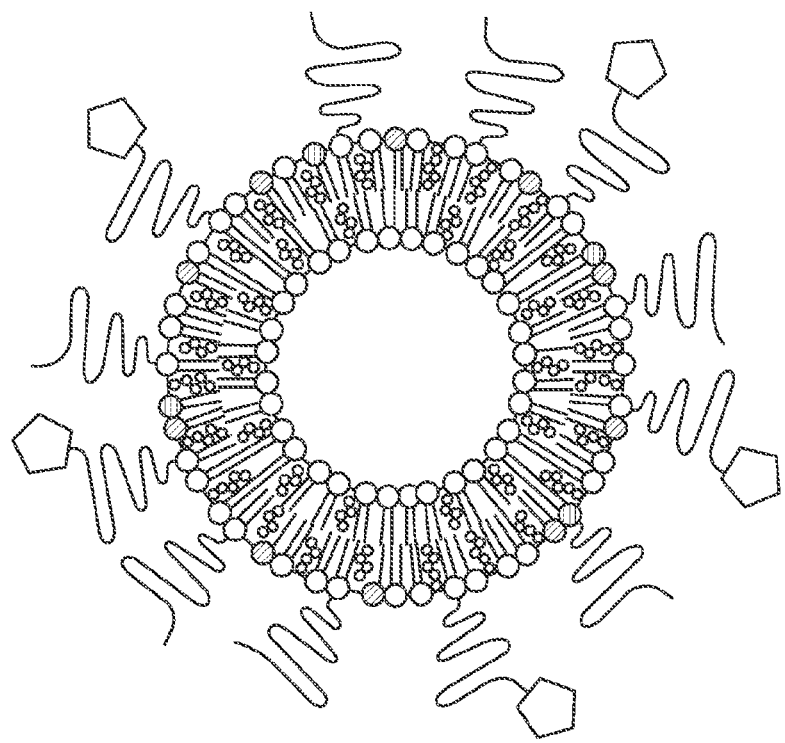
FIG. 16B is a schematic illustrating a lipid molecule conjugated to 4-carboxybenzamidine to DSPE-PEG(2000)-amine used to prepare liposome nanoparticles coupled with plasmin, as described in Example 9.

1. DCC activation of 4-carboxybenzamidine with DIEA in DCM
2. Incubate with DSPE-PEG(2000)-amine
3. Purify via RP-HPLC on C3 column FIG. 16A depicts the multivalent effect of 4-carboxybenzamidine conjugated to liposome nanoparticles and the resultant reduction in inhibitory constant caused by the multivalent effect (Liposomal 4CB: average 11.65 µM, stdev: 3.68; Free 4CB: average 292.47 µM, stdev: 6.50). FIG. 16B illustrates a liposome nanoparticle prepared by conjugating 4-carboxybenzamidine to DSPE-PEG(2000)-amine and linked to plasmin. The chemical structure of 4-carboxybenzamidine conjugated to DSPE-PEG(2000)-amine is shown below

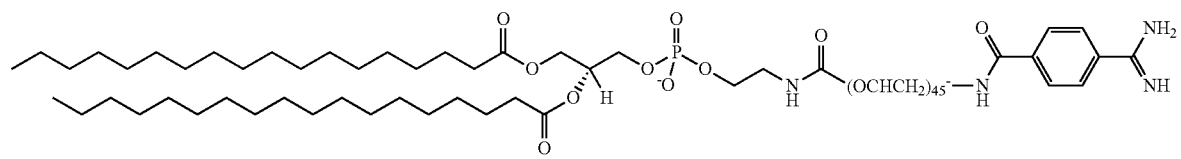

The monovalent binding affinity of plasmin for 4-carboxybenzamdine, as determined by S-2251 competitive binding inhibition assays, is 292.47±6.50 µM. When 4-carboxybenzamidine was coupled to the surface of a liposome the apparent multivalent inhibition constant in the same assay was 11.65±3.68 µM, a 26.5-fold increase in inhibition/binding. The multivalent interaction promotes the plasmin to remain bound to the nanoparticle surface in the absence of blood clot as demonstrated by the reduced inhibition constant, or reduced off rate of plasmin from the nanoparticle surface.

Example 10

In this Example, binding molecule conjugated lipids were prepared using a linker and solid phase peptide synthesis (SPPS) to conjugate 4-carboxybenzamidine to a synthetic lipid comprised of two palmitic acid molecules with a two lysine linker. 4CB-Lys-Lys-(Palmitic acid)$_2$ was synthesized using standard SPPS protocols on a Fmoc-Lys(ivDde) Wang resin using Fmoc chemistry. Fmoc was deprotected using 20% piperidine in DMF by incubating the resin 3 cycles for 3 minutes each. Carboxy-benzamidine was then coupled to the lysine following HBTU activation in DMF and DIEA at room temperature and was allowed to react to the lysine for 3.5 hours while agitating. The ivDde protecting group was then removed by incubating 3 cycles for 3 minutes of 2% hydrazine in DMF. Fmoc-Lys(Fmoc)-OH was then allowed to couple to the lysine residue following HBTU activation in DMF and DIEA at room temperature. Both Fmoc protecting groups were deprotected using 20% piperidine in DMF and palmitic acid was then allowed to conjugated to both lysine amines following HBTU activation in DMF and DIEA at room temperature. Kaiser tests were performed between coupling steps to monitor the synthesis progress. The lipid was cleaved from the resin in a solution of 4% triisopropylsilane, 4% D.I. water, and 92% TFA for 45 minutes at room temperature. The lipid was then purified via RP-HPLC on a Zorbax C3 column, and mass verified via mass spectrometry.

Figure 17:
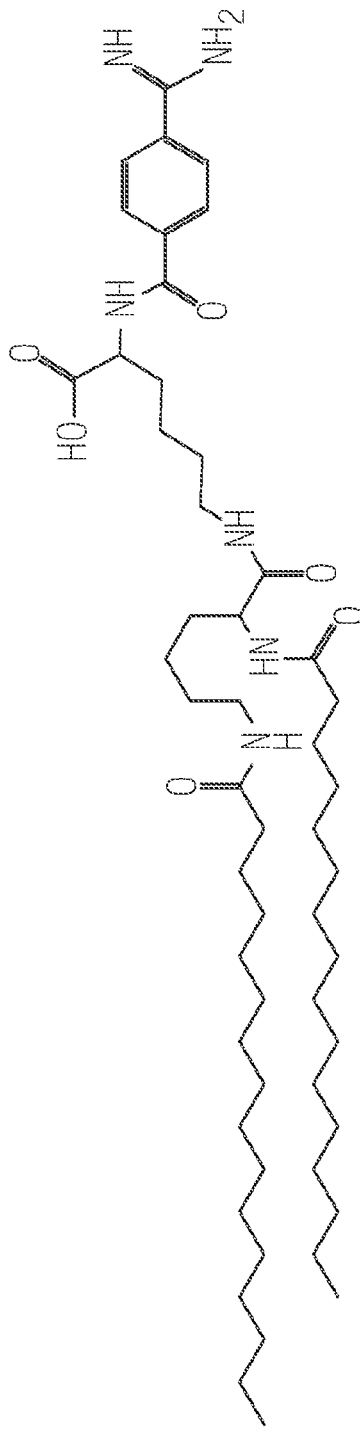
FIG. 17 illustrates the chemical structure of 4-carboxybenzamidine conjugated to with a synthetic two-tailed palmitic acid lipid via a lysine-lysine linker (4CB-Lys-Lys-(Palmitic acid)$_2$) as an alternate for making the benzamidine conjugated nanoparticle, as described in Example 10.

FIG. 17 illustrates the chemical structure of 4-carboxybenzamidine conjugated to a synthetic two tailed lipid via a lysine-lysine linker (4CB-Lys-Lys-(Palmitic acid)$_2$).

Example 11

In this Example, dynamic light scattering (DLS) was used to demonstrate the hydrodynamic diameter of delta-plasmin, micelle with and without the addition of delta-plasmin, and liposome with and without the addition of delta-plasmin.

Conjugation of 4-carboxybenzamidine to micelle and liposome nanoparticles was performed as described above to obtain functionalized nanoparticles having ~15 nm and ~100 nm hydrodynamic diameters, respectively. The functionalized liposome nanoparticles were incubated with delta plasmin in phosphate buffered saline (pH 7.4) and their hydrodynamic diameters were analyzed on a Malvern Zetasizer instrument. It is important to note that the hydrodynamic diameter of the 4CB functionalized nanoparticles increases by approximately the same size as free delta plasmin indicating that delta-plasmin is bound to the nanoparticle surface.

Figure 18A:
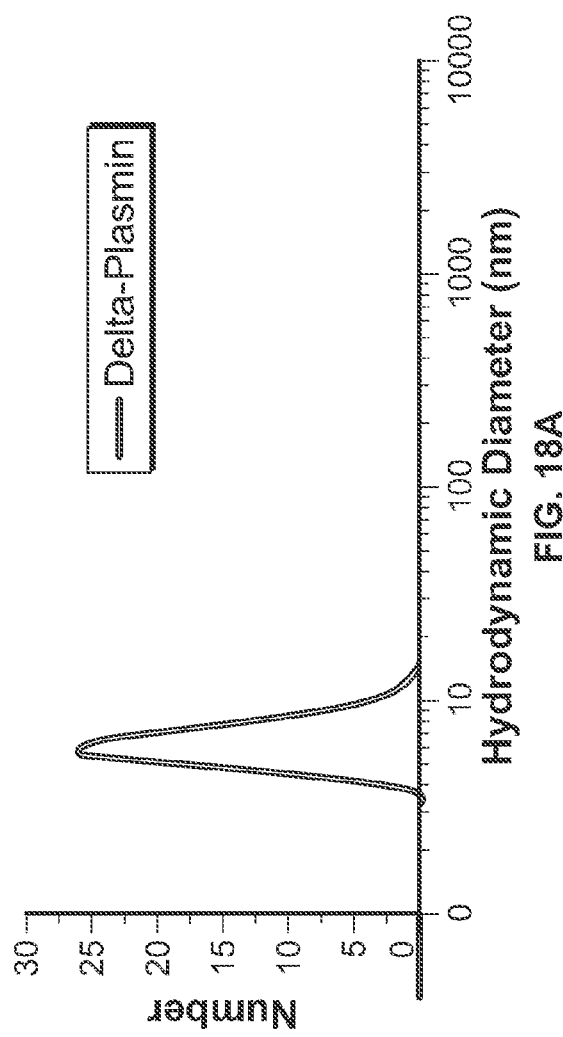
FIGS. 18A-18C are graphs depicting the hydrodynamic diameters of delta plasmin alone (FIG. 18A), delta plasmin associated with 4-carboxybenzamidine conjugated micelle nanoparticles (FIG. 18B), and delta plasmin associated with 4-carboxybenzamidine conjugated liposome nanoparticles (FIG. 18C), as described in Example 11.
Figure 18B:
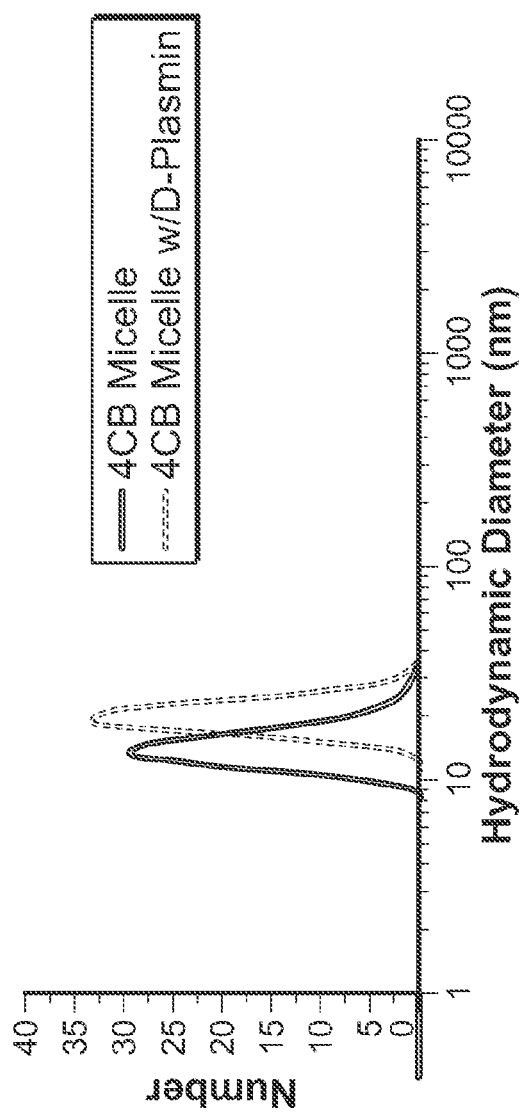
Figure 18C:
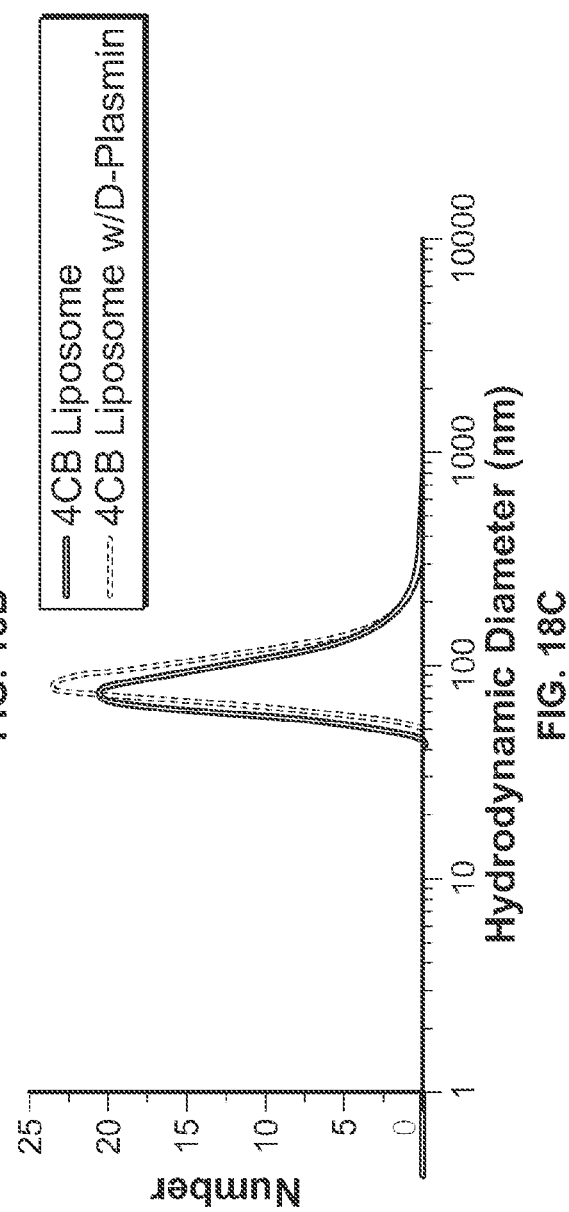

FIGS. 18A-18C depict the hydrodynamic diameters of delta plasmin alone, micelle nanoparticles with and without delta plasmin associated with their surface, and liposome nanoparticles with and without delta plasmin associated with their surface.

Example 12

In this Example, blood clot digestion by nanoparticles prepared using 4-carboxybenzamidine conjugated micelles and delta plasmin was analyzed in both PBS and serum.

Fresh blood was drawn and clotted in glass tubes at 37° C. for 1.5 hours. Clots were then cut, excess liquid was removed via light blotting, and weighed to produce clots of ~600 mg size. Clots were then transferred to phosphate buffered saline (PBS at pH 7.4) or serum. Delta plasmin, benzamidine conjugated micelle nanoparticles, and benzamidine conjugated micelle nanoparticles with delta plasmin associated with their surface were added to the blood clots and incubated for 2 hours at room temperature on a rocker protected from light. After incubation, the blood clots were again lightly blotted and weighed. Experimental parameters are summarized in Table 3 for the clot digestion assay performed in serum. The assay performed in PBS was nearly identical to the results presented in Table 4.

TABLE 4

| Clot Digestion Assay in Serum. | |
|---|---|
| Average clot size | 617.09 mg |
| Delta Plasmin stock concentration | 6.5 mg/mL |
| Delta Plasmin MW | 37000 kDa |
| Delta Plasmin stock concentration | 175.68 µM |
| Delta Plasmin/sample | 812.5 µg |
| Delta Plasmin/clot | 1.32 µg plasmin/mg clot |
| micelle/sample | 200 µL each |
| micelle concentration | 11.25 µM |
| micelle sample concentration | 3.46 µM |
| plasmins/micelle | 10 plasmins |
| 4CB stock micelle concentration | 203.9 µM |
| 4CB sample micelle concentration | 62.74 µM |
| 4CB/micelle | 18 4CB inhibitors |
| Delta Plasmin loading | 53.85% |
| serum per sample | 325 µL |
| percent serum | 50% |
| blood clot time | 1.5 hours |
| lysis time on rocker (room temp) | 2 hours |
| micelle surface area (14.78 nm Diameter) | 685.928 nm$^2$ |
| area/plasmin | 70.28124 nm$^2$ |
| plasmin surface area (6.48 nm Diameter) | 131.85 nm$^2$ |
| approximate plasmin footprint | 32.96 nm$^2$ |
| percent plasmin surface coverage | 46.90% |

Figure 19A:
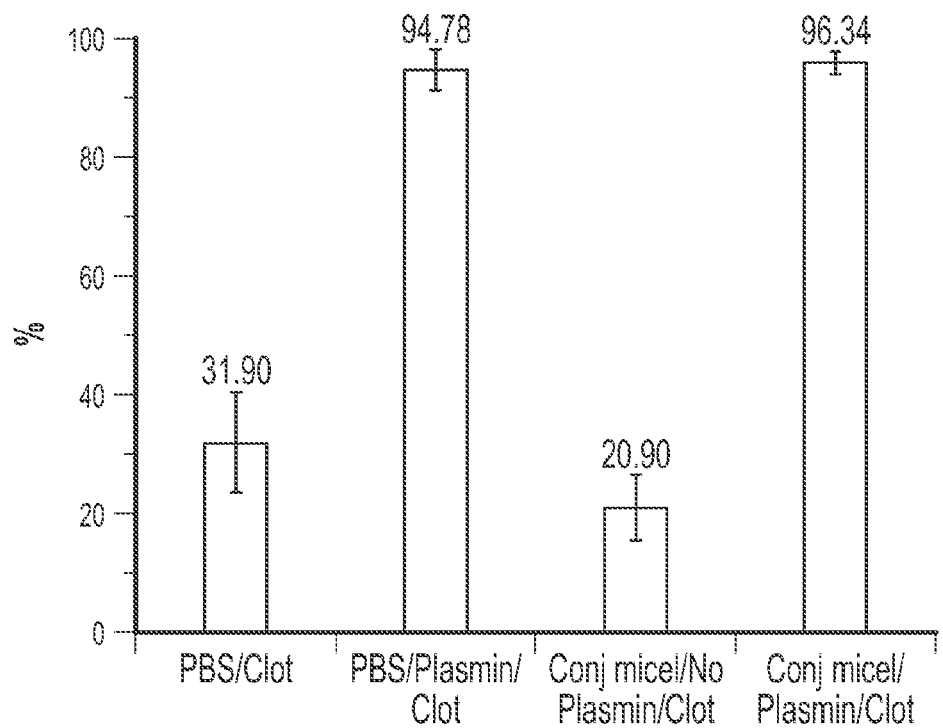
FIGS. 19A and 19B are graphs depicting the digestion of blood clots in PBS (FIG. 19A, raw data.
Figure 19B:
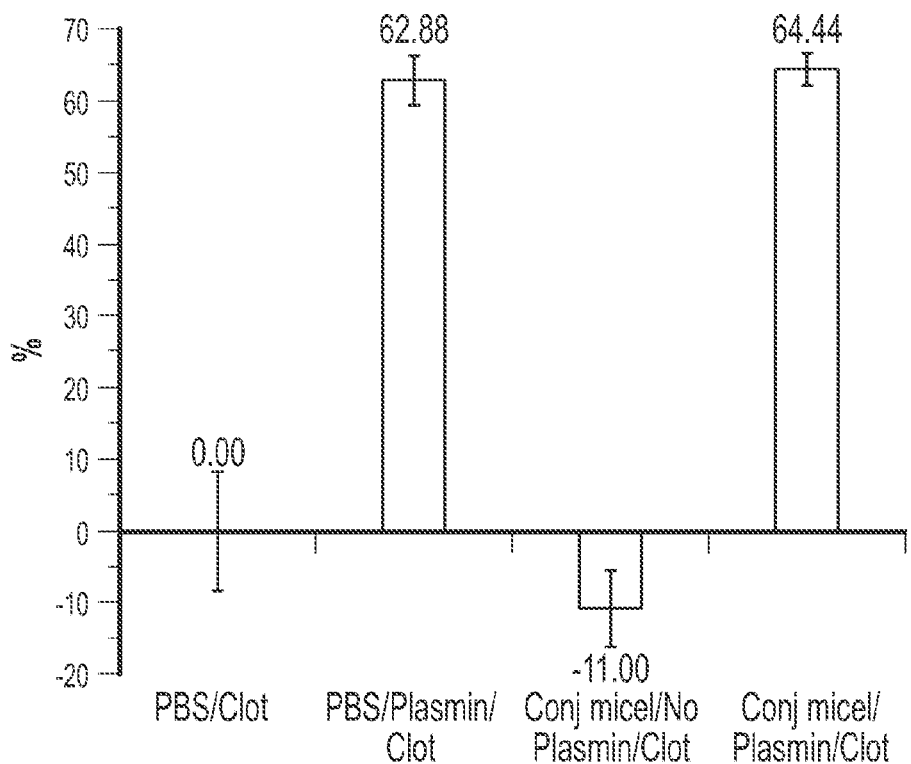
Figure 20:
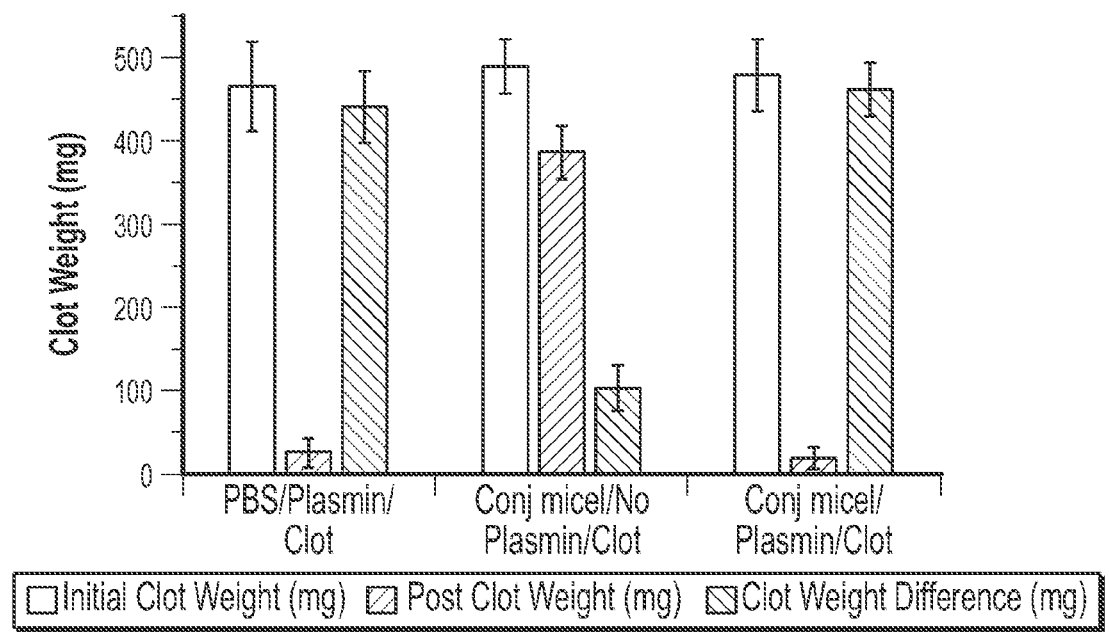
FIG. 20 is a graph depicting the change in clot weight for the experiments depicted in FIGS. 19A and 19B, as described in Example 12. Slide

FIGS. 19A and 19B depict the digestion of blood clots in PBS. FIG. 20 depicts the raw data of the change in clot weight from before and after clot digestion. This experiment demonstrates the ability of the 4CB inhibitor conjugated micelle bound delta-plasmin to be able to retain its ability to digest blood clots in an in vitro clot lysis assay in PBS at pH 7.4. Even though the 4CB conjugated micelle produced an inhibitory effect reducing the activity of plasmin when utilizing the S-2251 chromogenic substrate the multivalent expression of fibrin on the clot surface allows for favorable offloading kinetics allowing plasmin to function similarly in the presence and absence of the nanoparticle in regard to clot lysis efficacy as indicated by these results. To provide for favorable offloading kinetics the concentration of inhibitor in the incubated sample must be carefully selected to exceed the $K_d$ value of the inhibitor for the plasmin while not being so high as to prevent offloading upon kringle binding to fibrin. This allows for the tunable delivery described within this disclosure as variations to nanoparticle size, inhibitor binding affinity for the target molecule, surface density of the inhibitor molecule to the surface of the nanoparticle, administered concentration of the inhibitor molecule, and the target molecule affinity for the in vivo offloading site will all effect the therapeutic efficacy of the target molecule.

Figure 21A:
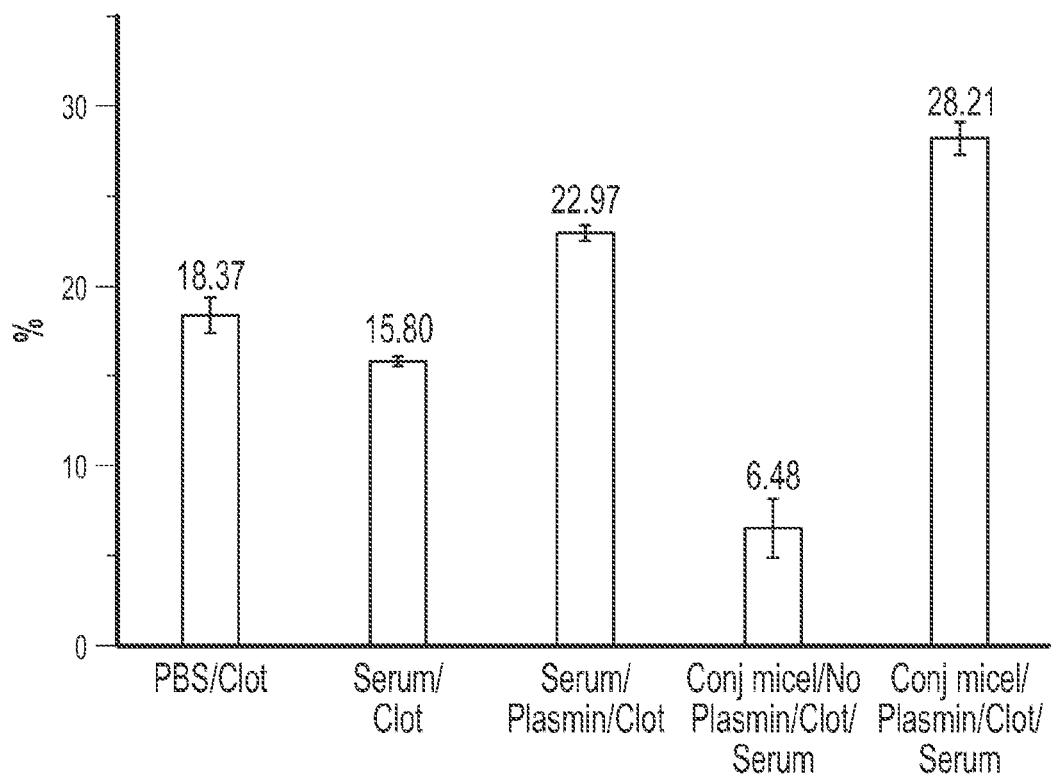
FIGS. 21A and 21B are graphs depicting the digestion of blood clots in serum (21A, raw data; 21B raw data with baseline blood clot digestion subtracted), as described in Example 12.
Figure 21B:
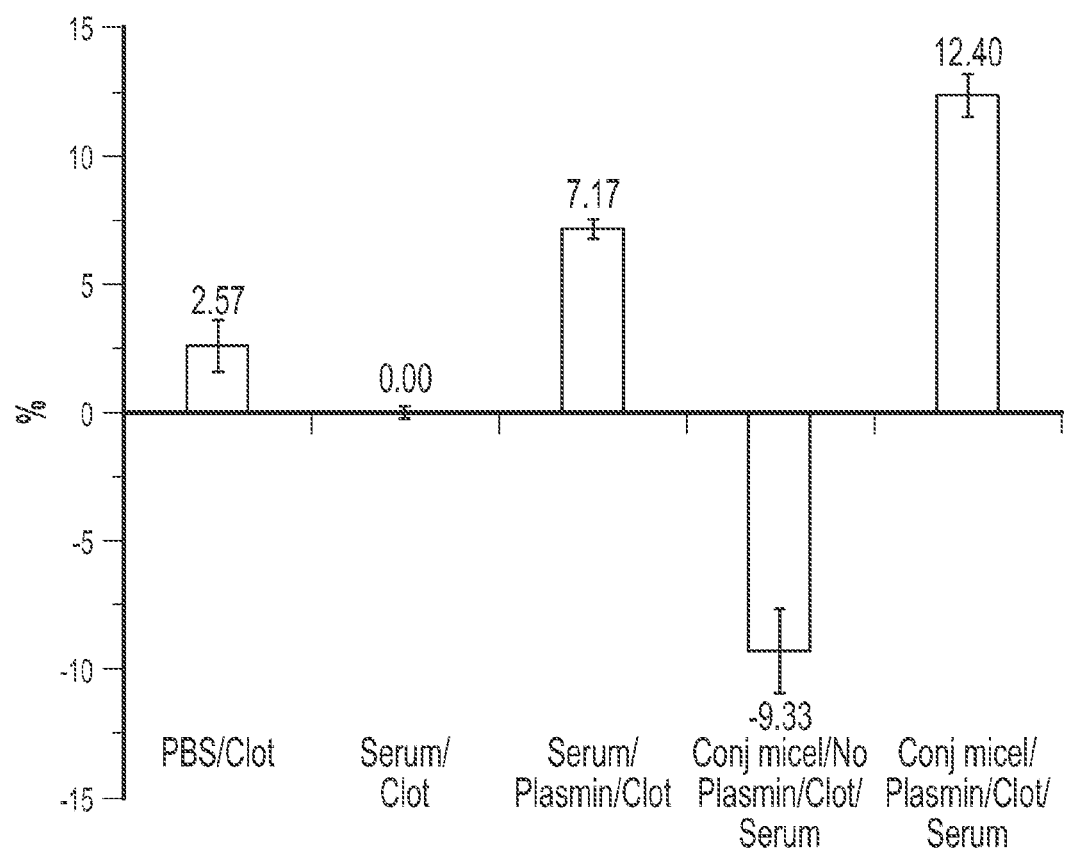

FIGS. 21A and 21B depict the digestion of blood clots in serum with the experimental parameters outlined in Table 3. FIG. 21B shows the background-corrected lysis rate for the micelle bound plasmin as compared with naked plasmin. The increase in clot digestion from 7.175 to 12.4% demonstrates a 73% relative increase in the digestion of clots using 4CB conjugated micelle nanoparticles delivering delta plasmin.

Plasmin and delta-plasmin are uniquely suited proteins for use in this delivery technique as they contain kringle domains that bind specifically to fibrin, found extensively throughout blood clots. In this regard the plasmin decorated nanoparticle functions as a targeted nanoparticle delivery system to selectively bind and lyse blood clots. Upon multivalent binding of the kringle domains to the clot surface, plasmin is released from the nanoparticle surface as the multivalent expression of fibrin on the clot surface greatly exceeds that of the multivalent presentation of inhibitor molecules on the nanoparticle surface. Since the inhibitory binding affinity of 4-carboxybenzamdine is comparable to the monovalent affinity of the plasmin kringle domain for fibrin, the local overexpression of fibrin drives kinetics resulting in the offloading of the plasmin to the clot surface allowing for site-specific clot dissolution.

These data, taken together, demonstrate the proof of concept validation for the use of functionalized nanoparticles to deliver active plasmin to blood clots and improve fibrinolysis. When naked plasmin is administered in the presence of serum, the anti-plasmin present in the serum rapidly inactivates the plasmin preventing it from digesting clot. When the plasmin is associated to the surface of a nanoparticle as described in the present disclosure, the plasmin is less susceptible to inactivation via endogenous blood proteins and therefore allows improved delivery of the plasmin to the surface of the blood clot and therefore an increased fibrinolytic effect. This increase in fibrinolysis present in the clot digestion assay in the presence of serum, but lack of improvement in the absence of serum as demonstrated in the PBS clot digestion assay, is likely due to the absence of anti-plasmin and other plasmin inactivating blood proteins.

Significantly, in both the PBS and serum clot lysis assays, when the functionalized micelle was incubated with the sample in the absence of added delta-plasmin the endogenous percent clot lysis was significantly reduced. This result was expected as the micelles can actively bind endogenous plasmin and reduce its lysis activity. This result was not observed when plasmin was coadministered with the micelles is due to the vastly different relative ratios of plasmin to inhibitor in the two different samples. As such, there also exists applications where the functionalized nanoparticle can be administered in the absence of plasmin to prevent/reduce endogenous clot lysis by binding endogenous plasmin.

Example 13

In this Example, an in-vitro lung model of pulmonary embolism was used to demonstrate the ability of the delivery system to deliver delta plasma.

Figure 22:
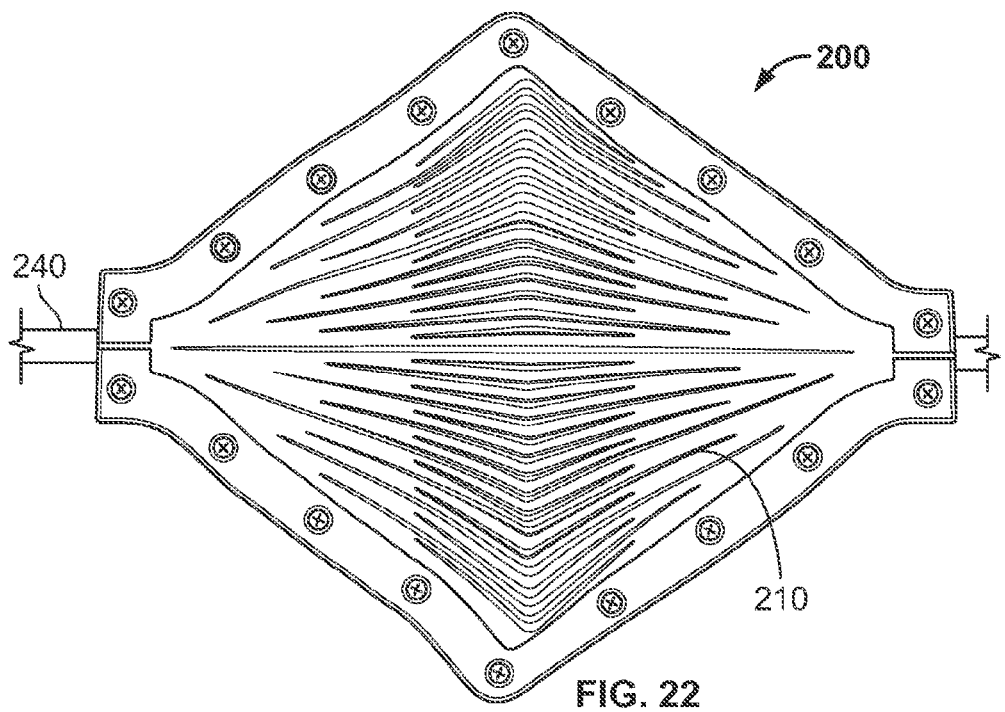
FIG. 22 depicts an in-vitro circulating plasma lung model as used in Examples 13 and 14.
Figure 23:
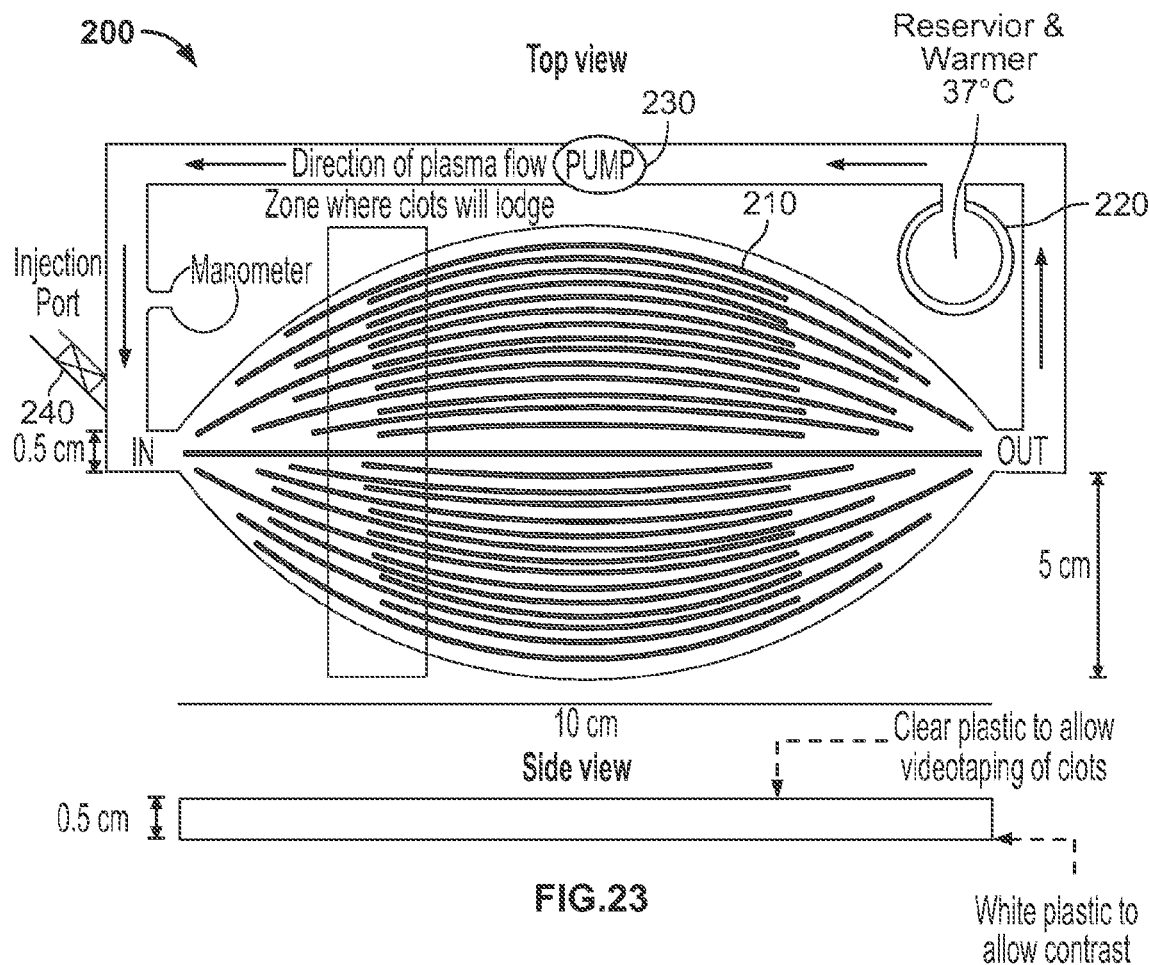
FIG. 23 depicts a schematic of an in-vitro circulating plasma lung model as used in Examples 13 and 14.

The in-vitro circulating plasma lung model 200 of pulmonary embolism (as shown in FIGS. 22 and 23), consists of a 3-D printed circuit 210, designed to mimic lung vasculature, and in which preformed blood clots of known mass are placed. This "lung" is in fluid connection with a reservoir 220 of approximately 200-250 mL of human plasma, type-matched to the clots, that is recirculated with a peristaltic pump 230, passed through a heating element (not shown), then pumped through the lung itself at a physiological constant pressure. An injection port 240 allows injection of reagents, enzymes or other molecules. After lysis is initiated, the "lung" is circulated for one hour. Clots are weighed before and after completion of the experiment reweighed, to provide for percentage of clot lysis information for each treatment regime.

Figure 24:
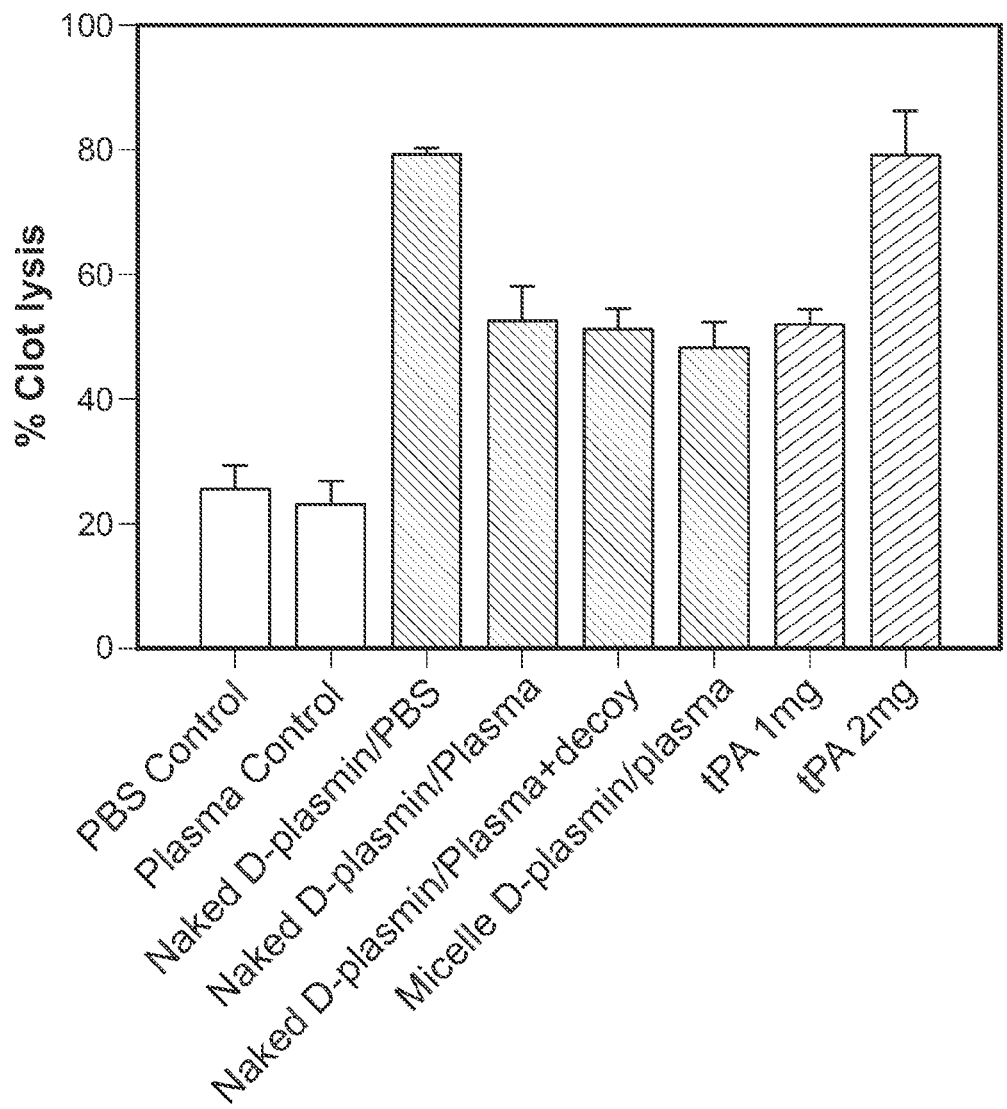
FIG. 24 is a graph illustrating percent clot lysis as analyzed in Example 13.
Figure 25:
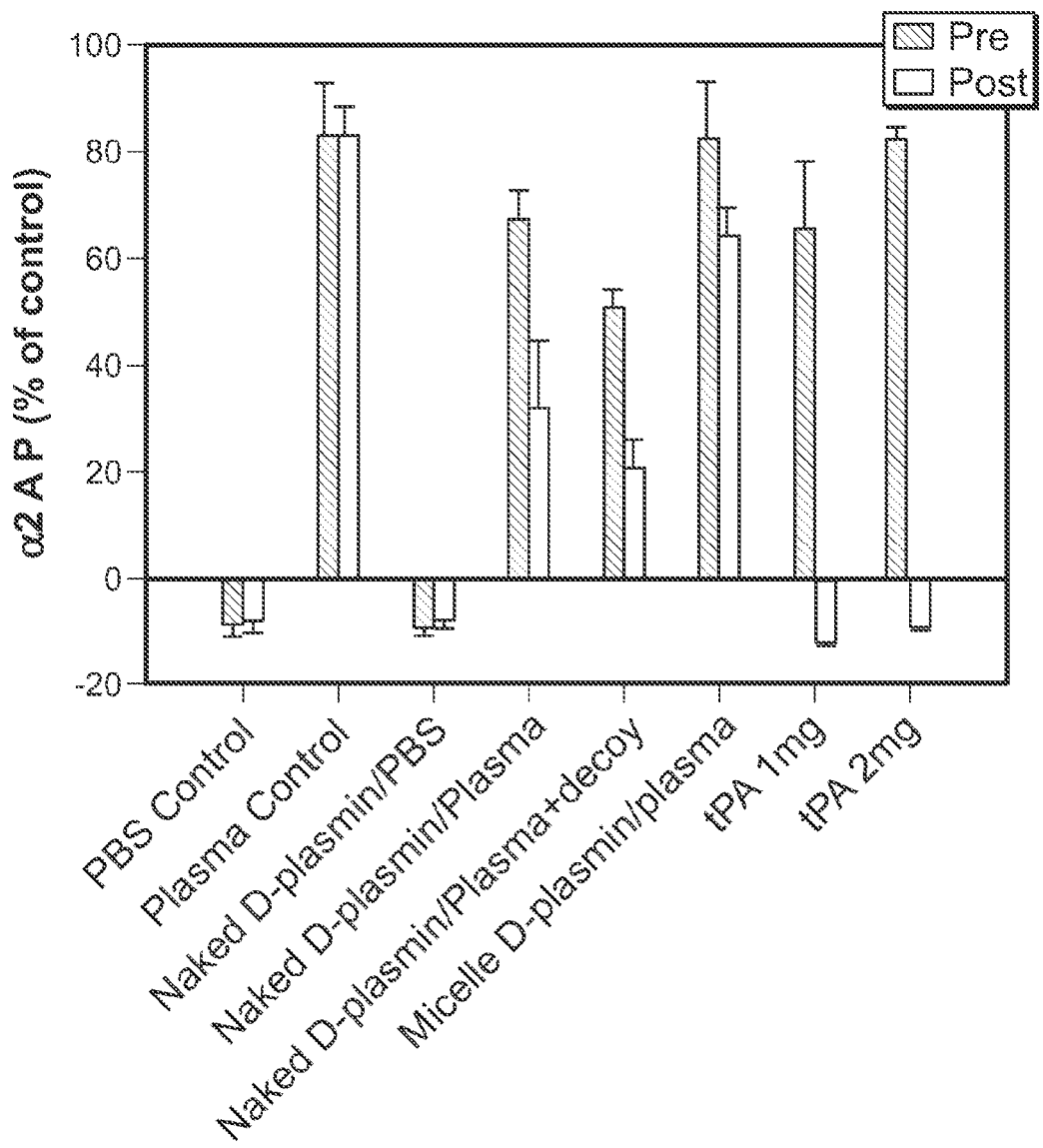
FIG. 25 is a graph illustrating percent antiplasmin as analyzed in Example 13.

As shown in FIG. 24, when delta plasmin was delivered via 4-carboxybenzamidine, conjugated via PEG to a micelle, in the circulating in-vitro lung model of pulmonary embolism (Micelle D-plasmin/plasma), the percentage lysis was not different than naked plasmin in plasma. However, as shown in FIG. 25, the reduction in antiplasmin (labeled on the Y axis as α2 AP) was significantly less, indicating less destruction of delta plasmin. It is also important to note that by using tPA for clot lysis that all of the antiplasmin is fully depleted from the plasma. This eliminates the ability of endogenous antiplasmin to keep any free plasmin in check and results in non-specific systemic clot lysis.

Example 14

In this Example, pulmonary embolism was simulated using the in-vitro lung model of Example 13 and the ability of the delivery system of the present disclosure was analyzed for its ability to remove clots.

Particularly, human plasma (200-250 mL), recirculated (37° C.) and loaded with approximately 4 grams typematched clots was injected into the delivery system. After 1 hour of circulation, the clots were removed and weighed.

Figure 26A:
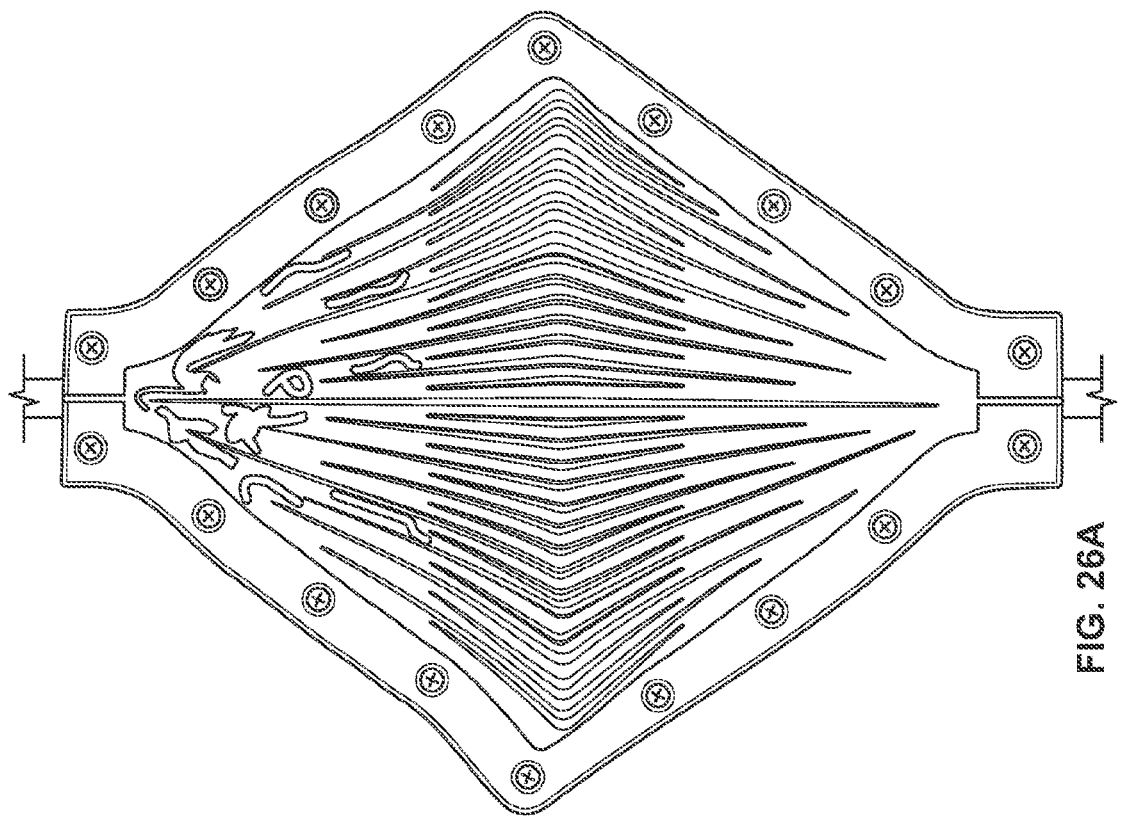
FIGS. 26A and 26B depict the in-vitro circulating plasma lung model in use.
Figure 26B:
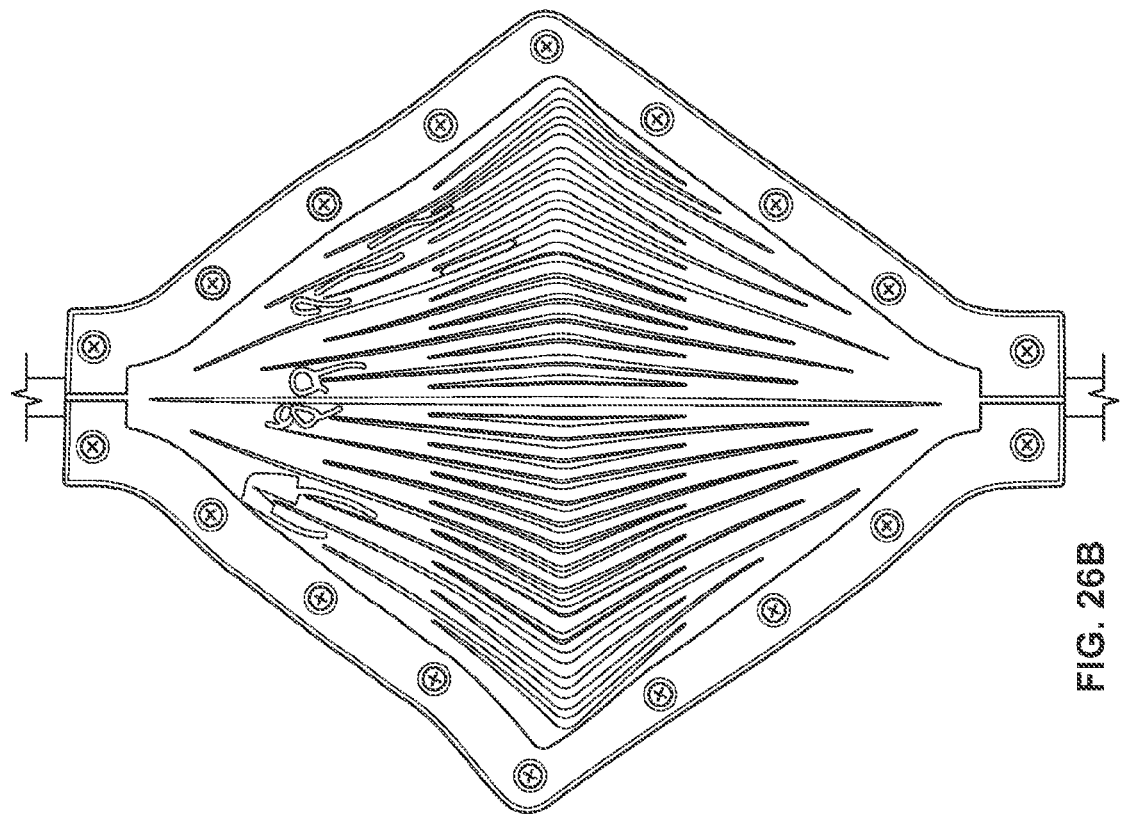

As shown in FIGS. 26A & 26B, the delivery systems of the present disclosure achieved clot lysis in vivo.

These results demonstrated that the nanoparticle delivery system can be utilized to deliver proteins to desired targets. In many iterations of this technique substitution of any or all of the components to facilitate use of a different nanoparticle, protein or target through modification of the composition of the system is also included such as modifications to: non-functionalized lipids, functionalized lipids, affinity ligands, proteins, nanoparticles, and targets.

The invention claimed is:

1. A method of encapsulating an enzyme, the method comprising:

covalently coupling an affinity ligand to a lipid molecule to form a lipid molecule-affinity ligand conjugate;

forming a mixture comprising the lipid molecule-affinity ligand conjugate and an enzyme, wherein the enzyme reversibly couples to the affinity ligand of the lipid molecule-affinity ligand conjugate; and preparing a liposome nanoparticle using the mixture of the lipid molecule-affinity ligand conjugate and the enzyme, wherein the resulting liposome nanoparticle comprises the affinity ligand covalently coupled to the lipid molecule, wherein the affinity ligand is reversibly coupled to the enzyme and wherein the affinity ligand and the enzyme are encapsulated within the interior of the liposome nanoparticle.

2. The method of claim 1, wherein the lipid molecule is selected from the group consisting phosphatidylcholine, phosphatidic acid, phosphatidylethanolamine, phosphatidylserine, a phosphoinositide, a phosphingolipid and combinations thereof.

3. The method of claim 1, wherein the liposome nanoparticle further comprises cholesterol.

4. The method of claim 1, wherein the affinity ligand is selected from the group consisting of a small molecule, a peptide, a peptidomimetic and combinations thereof.

5. The method of claim 4, wherein the affinity ligand is selected from the group consisting of benzamidine, 4-aminobenzamidine, 4-carboxybenzamidine, 4-aminomethyl benzamidine, pentamidine, bivalirudin, argatroban, melagatran, ximelagatran, dabigatran, amprenavir, atazanavir, darunavir, fosamprenavir, indinavir, lopinavir/ritonavir combination, nelfinavir, ritonavir, saquinavir, tipranavir, serpin, hirudin, bivalirudin, lepirudin, desirudin, and combinations thereof.

6. The method of claim 1, wherein the liposome nanoparticle further comprises a bulk lipid selected from the group consisting of HSPC, DPPC, cholesterol, a PEGylated lipid molecule, and combinations thereof.

7. The method of claim 1, wherein the enzyme is a protease.

8. The method of claim 7, wherein the enzyme is a serine protease.

9. The method of claim 1, wherein the enzyme is selected from the group consisting of plasmin, delta plasmin, tissue plasminogen activator, urokinase, protein S, trypsin, chymotrypsin, elastase, peptidase, subtilisin, and combinations thereof, and wherein the enzyme can digest a blood clot.

10. The method of claim 1, wherein the enzyme is plasmin or delta-plasmin, and wherein the affinity ligand is benzamidine or a benzamidine derivative.

11. The method of claim 1, wherein the enzyme is selected from the group consisting of kallekreins, reptilase, tissue factor, factor XII, factor XI, factor XIa, factor XIIa, factor X, prothrombin, thrombin, protein c, and protein Z, and wherein the enzyme can induce blood clot formation.

\* \* \* \* \*

SEQUENCE LISTING

<160> NUMBER OF SEQ ID NOS: 2

<210> SEQ ID NO 1
<211> LENGTH: 791
<212> TYPE: PRT
<213> ORGANISM: Homo sapiens

```
<400> SEQUENCE: 1

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415
```

Trp Cys Phe Thr Thr Asp Pro Ser Val Arg Trp Glu Tyr Cys Asn Leu
            420                 425                 430

Lys Lys Cys Ser Gly Thr Glu Ala Ser Val Ala Pro Pro Val
        435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
                500                 505                 510

Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
        530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
            690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
        770                 775                 780

Glu Gly Val Met Arg Asn Asn
785                 790

<210> SEQ ID NO 2
<211> LENGTH: 335
<212> TYPE: PRT
<213> ORGANISM: Artificial Sequence
<220> FEATURE:

<223> OTHER INFORMATION: Synthetic

<400> SEQUENCE: 2

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
            35                  40                  45

Glu Gly Leu Glu Glu Asn Tyr Cys Arg Asn Pro Asp Asn Asp Pro Gln
            50                  55                  60

Gly Pro Trp Cys Tyr Thr Thr Asp Pro Glu Lys Arg Tyr Asp Tyr Cys
65                  70                  75                  80

Asp Ile Leu Glu Cys Ala Ala Pro Ser Phe Asp Cys Gly Lys Pro Gln
                85                  90                  95

Val Glu Pro Lys Lys Cys Pro Gly Arg Val Val Gly Gly Cys Val Ala
                100                 105                 110

His Pro His Ser Trp Pro Trp Gln Val Ser Leu Arg Thr Arg Phe Gly
                115                 120                 125

Met His Phe Cys Gly Gly Thr Leu Ile Ser Pro Glu Trp Val Leu Thr
            130                 135                 140

Ala Ala His Cys Leu Glu Lys Ser Pro Arg Pro Ser Ser Tyr Lys Val
145                 150                 155                 160

Ile Leu Gly Ala His Gln Glu Val Asn Leu Glu Pro His Val Gln Glu
                165                 170                 175

Ile Glu Val Ser Arg Leu Phe Leu Glu Pro Thr Arg Lys Asp Ile Ala
                180                 185                 190

Leu Leu Lys Leu Ser Ser Pro Ala Val Ile Thr Asp Lys Val Ile Pro
                195                 200                 205

Ala Cys Leu Pro Ser Pro Asn Tyr Val Val Ala Asp Arg Thr Glu Cys
                210                 215                 220

Phe Ile Thr Gly Trp Gly Glu Thr Gln Gly Thr Phe Gly Ala Gly Leu
225                 230                 235                 240

Leu Lys Glu Ala Gln Leu Pro Val Ile Glu Asn Lys Val Cys Asn Arg
                245                 250                 255

Tyr Glu Phe Leu Asn Gly Arg Val Gln Ser Thr Glu Leu Cys Ala Gly
                260                 265                 270

His Leu Ala Gly Gly Thr Asp Ser Cys Gln Gly Asp Ser Gly Gly Pro
                275                 280                 285

Leu Val Cys Phe Glu Lys Asp Lys Tyr Ile Leu Gln Gly Val Thr Ser
                290                 295                 300

Trp Gly Leu Gly Cys Ala Arg Pro Asn Lys Pro Gly Val Tyr Val Arg
305                 310                 315                 320

Val Ser Arg Phe Val Thr Trp Ile Glu Gly Val Met Arg Asn Asn
                325                 330                 335
```